US011842488B2

(12) United States Patent
Tosun et al.

(10) Patent No.: US 11,842,488 B2
(45) Date of Patent: Dec. 12, 2023

(54) EXPLAINABLE AI (XAI) PLATFORM FOR COMPUTATIONAL PATHOLOGY

(71) Applicant: SpIntellx, Inc., Pittsburgh, PA (US)

(72) Inventors: Akif Burak Tosun, Pittsburgh, PA (US); Srinivas Chakra Chennubhotla, Pittsburgh, PA (US); Jeffrey Louis Fine, Pittsburgh, PA (US)

(73) Assignee: SpIntellx, Inc., Pittsburgh, PA (US)

( * ) Notice: Subject to any disclaimer, the term of this patent is extended or adjusted under 35 U.S.C. 154(b) by 0 days.

(21) Appl. No.: 17/843,309

(22) Filed: Jun. 17, 2022

(65) Prior Publication Data

US 2023/0142758 A1    May 11, 2023

Related U.S. Application Data

(63) Continuation of application No. 16/819,866, filed on Mar. 16, 2020, now Pat. No. 11,367,184.

(60) Provisional application No. 62/819,035, filed on Mar. 15, 2019.

(51) Int. Cl.
| | |
|---|---|
| *G16H 30/40* | (2018.01) |
| *G06T 7/00* | (2017.01) |
| *G06F 18/2431* | (2023.01) |
| *G06V 10/778* | (2022.01) |
| *G06V 20/69* | (2022.01) |

(52) U.S. Cl.
CPC ........ *G06T 7/0012* (2013.01); *G06F 18/2431* (2023.01); *G06V 10/7784* (2022.01); *G06V 20/69* (2022.01); *G06V 20/695* (2022.01); *G06V 20/698* (2022.01); *G16H 30/40* (2018.01); *G06T 2200/24* (2013.01); *G06T 2207/20081* (2013.01); *G06T 2207/30016* (2013.01); *G06T 2207/30024* (2013.01); *G06T 2207/30061* (2013.01); *G06T 2207/30068* (2013.01); *G06T 2207/30096* (2013.01); *G06T 2207/30242* (2013.01)

(58) Field of Classification Search
CPC .................................................... G06T 7/0012
See application file for complete search history.

(56) References Cited

U.S. PATENT DOCUMENTS

| | | | |
|---|---|---|---|
| 2012/0033861 A1* | 2/2012 | Dai .......................... | G06F 18/41 382/128 |
| 2019/0050999 A1* | 2/2019 | Piat .......................... | G06T 7/337 |
| 2019/0219579 A1* | 7/2019 | Khelifa ................. | G01N 33/574 |

* cited by examiner

*Primary Examiner* — Oneal R Mistry
(74) *Attorney, Agent, or Firm* — Goodwin Procter LLP

(57) ABSTRACT

Pathologists are adopting digital pathology for diagnosis, using whole slide images (WSIs). Explainable AI (xAI) is a new approach to AI that can reveal underlying reasons for its results. As such, xAI can promote safety, reliability, and accountability of machine learning for critical tasks such as pathology diagnosis. HistoMapr provides intelligent xAI guides for pathologists to improve the efficiency and accuracy of pathological diagnoses. HistoMapr can previews entire pathology cases' WSIs, identifies key diagnostic regions of interest (ROIs), determines one or more conditions associated with each ROI, provisionally labels each ROI with the identified conditions, and can triages them. The ROIs are presented to the pathologist in an interactive, explainable fashion for rapid interpretation. The pathologist can be in control and can access xAI analysis via a "why?" interface. HistoMapr can track the pathologist's decisions and assemble a pathology report using suggested, standardized terminology.

31 Claims, 34 Drawing Sheets

- Present manual approach is inefficient and is error prone
- High degree of discordance between pathologists
- Inefficient case triaging Table 1: Diagnostic Categories and Subcategories

| | |
|---|---|
| Invasive carcinoma | Invasive/infiltrating ductal carcinoma |
| | Invasive/infiltrating lobular carcinoma |
| | Invasive/infiltrating mammary carcinoma |
| DCIS | Ductal carcinoma in-situ (DCIS) |
| | Solid papillary carcinoma |
| | Encapsulated papillary carcinoma |
| High-risk | Atypical ductal hyperplasia (ADH) |
| | Atypical locular Hyperplasia (ALH) |
| | Lobular carcinoma in-situ (LCIS) |
| | Flat epithelial atypia (FEA) |
| | Atypical vascular lesion/proliferation |
| | Intraductal papilloma |
| | Radial scar |
| | Complex/radial sclerosing lesion |
| | Phyllodes |
| | Fibroepithelial |
| Low-risk/benign | Fibroadenoma |
| | Fibrocystic changes |
| | Ductal epithelial hyperplasia |
| | Columnar cell changes and hyperplasia |
| | Sclerosing adenosis |
| | Pseudo angiomatous stromal hyperplasia |
| | Apocrine metaplasia |
| | Benign/ unremarkable / normal |

FIG. 13

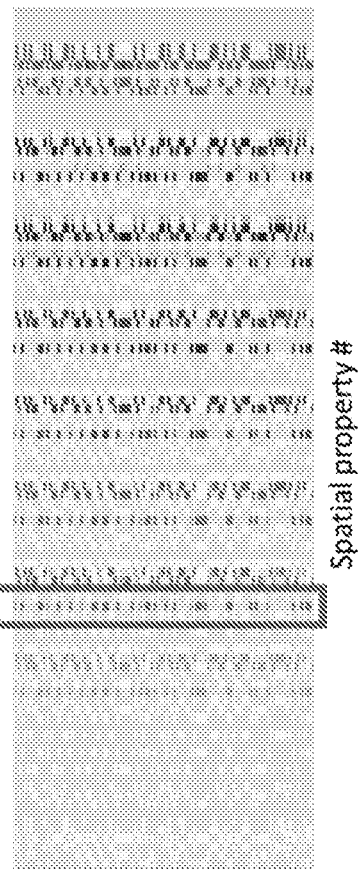
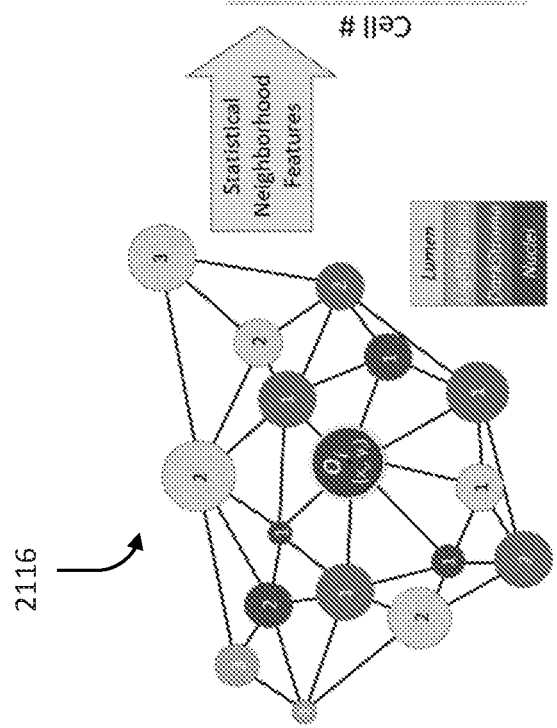
FIG. 21F
FIG. 21E

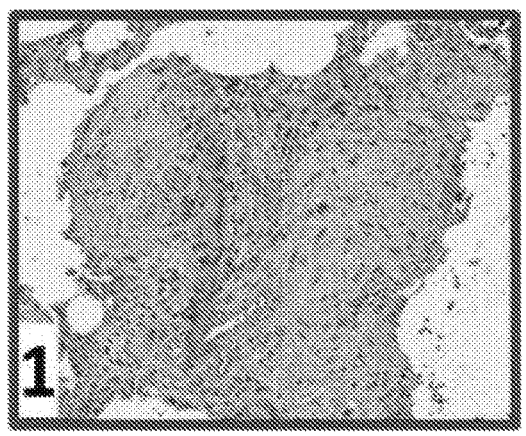
FIG. 22A1
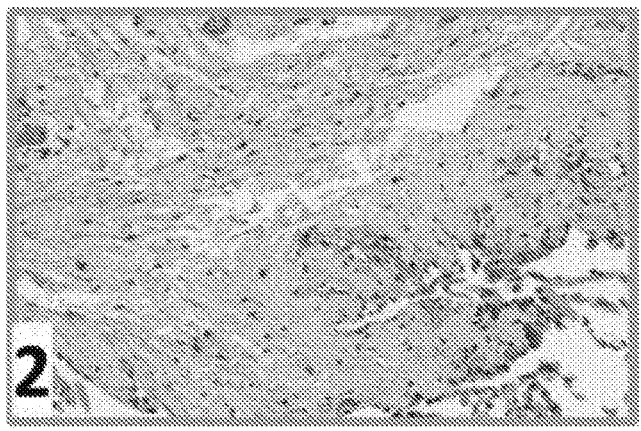
FIG. 22A2
2202
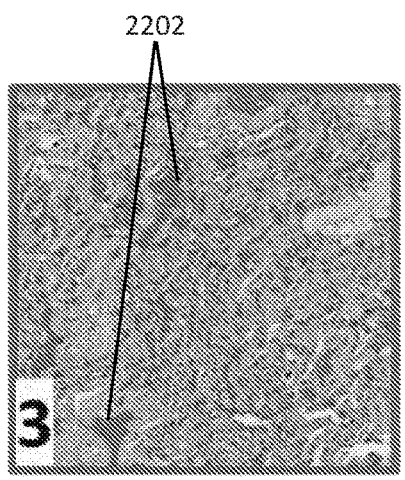
FIG. 22A3
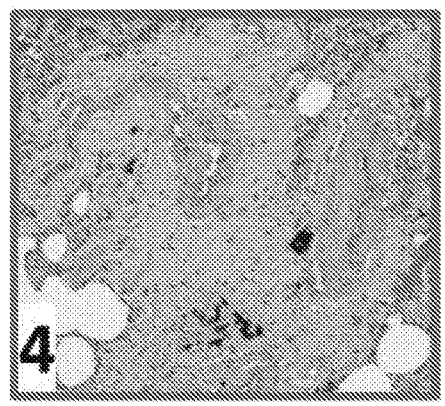
FIG. 22A4
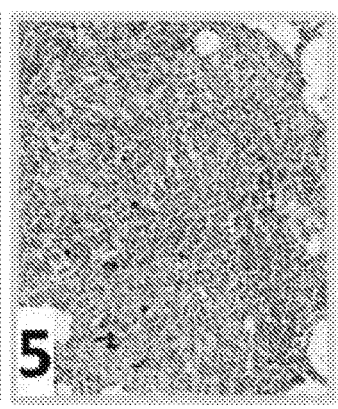
FIG. 22A5

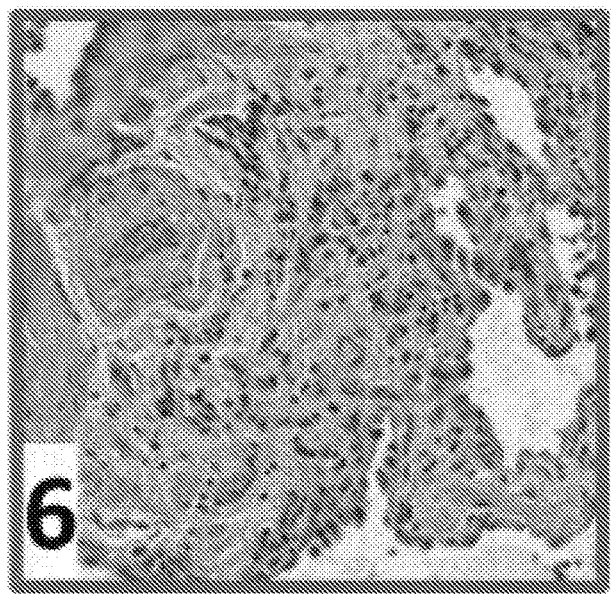
FIG. 22A6
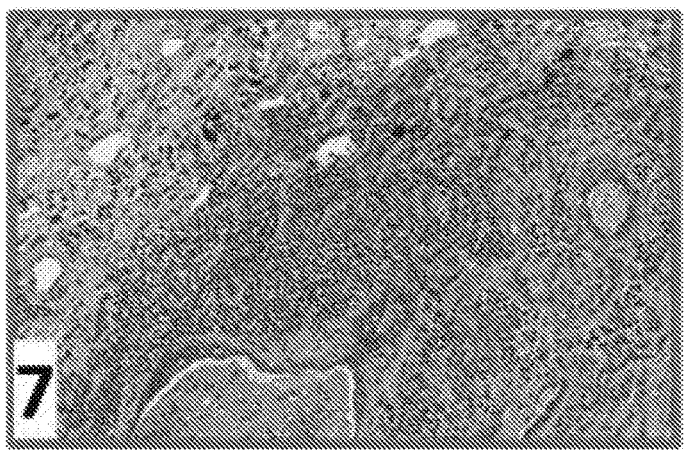 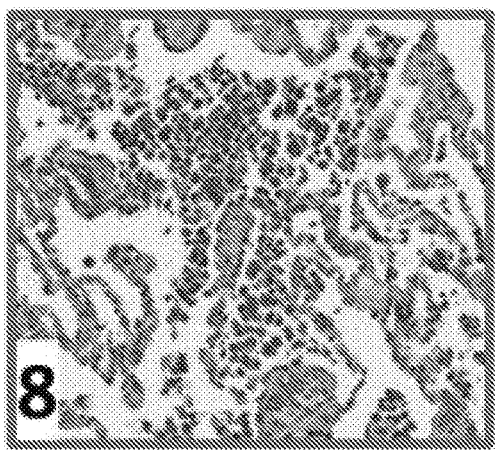
FIG. 22A7          FIG. 22A8

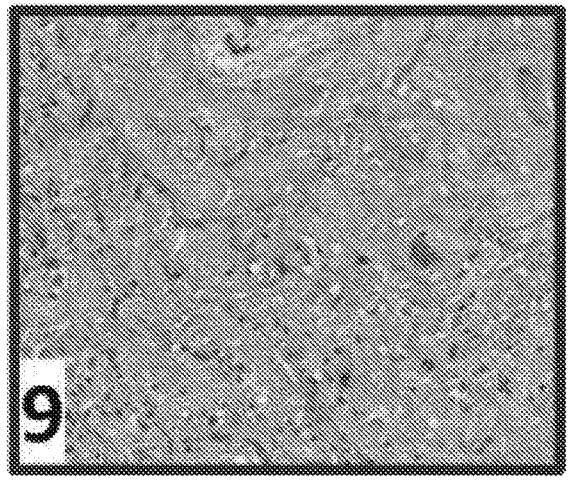
FIG. 22A9
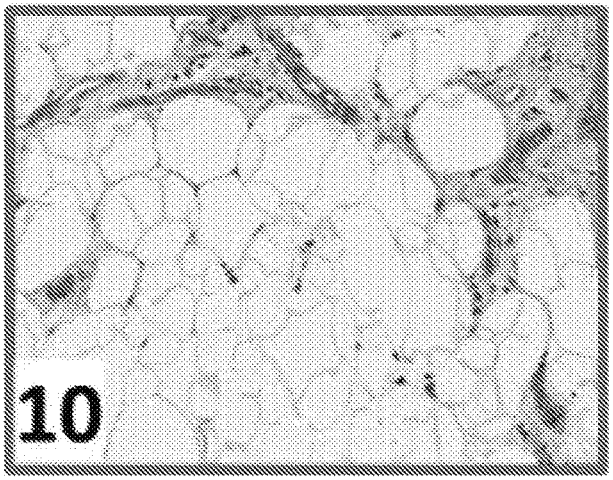
FIG. 22A10
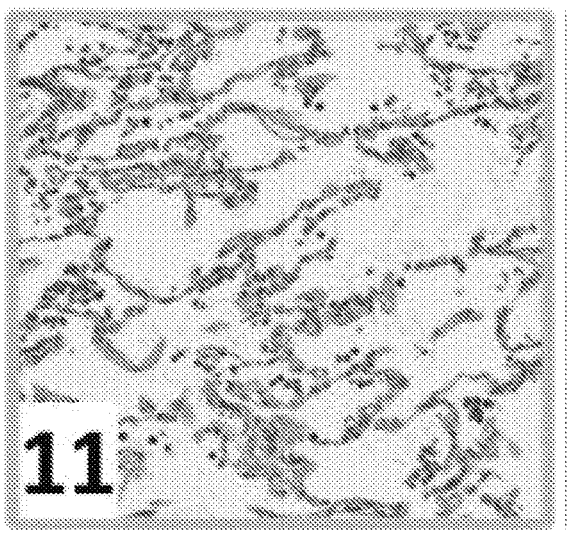
FIG. 22A11
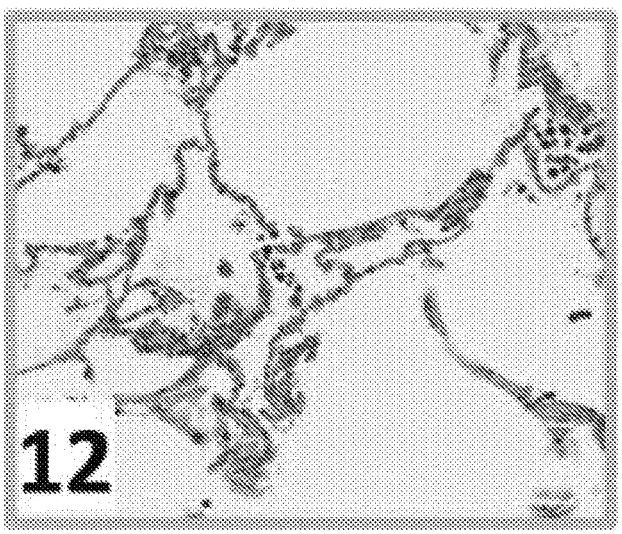
FIG. 22A12

EXPLAINABLE AI (XAI) PLATFORM FOR COMPUTATIONAL PATHOLOGY

CROSS-REFERENCE TO RELATED APPLICATIONS

This application is a continuation of U.S. patent application Ser. No. 16/819,866, filed on Mar. 16, 2019, which claims priority to and benefit of U.S. Provisional Patent Application No. 62/819,035, entitled "An Explainable AI (xAI) Platform for Computational Pathology," filed on Mar. 15, 2019, the entire contents of which are incorporated herein by reference.

FIELD OF THE INVENTION

This disclosure generally relates to an artificial intelligence (AI)-based system that performs image analysis and manipulation and, in particular, to a system that can assist in classification of one or more regions of an image based on the respective conditions indicated by those regions, where such conditions are determined using an explainable artificial intelligence (xAI)-based platform.

BACKGROUND

A growing number of pathologists have transitioned to viewing digital images of patient slides on computer monitors with the recent growth of digital pathology whole slide image (WSI) platforms. Following a protracted course, the FDA recently approved a first WSI system as a class II medical device and there are several additional WSI platform vendors (e.g., Leica, Philips, Roche, etc.). In response to these new market forces and to recent technology advances outside of pathology, a new field of computational pathology is emerging that applies machine learning to WSI. This has also led to innovative new concepts such as computer assisted diagnosis for pathologists (pCAD), that propose methods for integration of machine learning into pathology workflow.

Deep learning in the form of convolutional neural networks has been popular in early computational pathology efforts. While powerful in isolated, lower level applications such as mitosis counting or cancer detection, deep learning has not yet yielded validated, comprehensive, high level systems. There is also pathologist fear and skepticism about the application of AI to pathology, and there is no consensus about how pathologists should supervise or work with computational pathology systems.

SUMMARY

To address the challenges discussed above, various techniques described herein use xAI for analysis and inferencing in pathology. As an example, inferences from breast biopsies are derived using xAI to assist pathologists. A crucial new concept is explainable AI (xAI), which refers to AI that can justify its results with data. This is intended to address certain issues pertaining to AI-based analysis such as bias, transparency, safety, and causality. Bias refers to potentially flawed AI resulting from biased training data, which might appear to work initially but could later fail catastrophically. In various embodiments, our xAI platform (also referred to as HistoMapr) can prevent such occurrences by providing real-time feedback to its users about the xAI's process of deriving the inference. Using this feedback, the user (e.g., a pathologist) can determine if the xAI inferencing is based on a biased training dataset. Transparency is related; xAI can justify its results to users providing them with all of the information needed to make good decisions based on xAI recommendations.

In various embodiments, such information may include:
1) Why—a list of quantitated features, each with a plus/minus score that influences both the diagnostic label and its confidence score;
2) Why not—same as above, but also a ranked list of alternative provisional diagnoses with its own plus/minus tally of the quantitated features. The features associated with the alternative provisional diagnosis the same as above, but they generally have different plus/minus values for various different provisional diagnoses;
3) I know where you succeed—the features in 1 and 2, in context of the ROI image, in context of pathologist user's domain knowledge; if concordant then the user feels confident that HistoMapr succeeded
4) When you fail—same features as #3 but if they are discordant then the pathologist knows the xAI may have failed
5) When to trust—based on full situational awareness of why/why not, succeed/fail, on all of the ROIs
6) When to not trust—an executive decision based upon preceding factors; the pathologist may be provided with the option of not trusting the xAI, and proceeding to diagnose with a manual WSI review.

In pathology, patient safety is paramount and is the result of a complex interaction between pathologist, other physicians and laboratory personnel, and computer systems including computational pathology applications. Patient safety can be improved by xAI not only by reducing undetected bias or by providing transparency to the pathologist, it is also related to the pathologist being able to monitor xAI's functionality in real-time, on individual patient samples. In other words, various embodiments of the xAI system described herein provides an explanation of a particular individual's pathology at the time the pathologist is reviewing it. The explanation is not limited to retrospective or accumulated data review of multiple patients.

Finally, causality refers to scientifically understanding the pathological mechanisms underlying xAI systems. Many deep learning efforts simply chase engineering statistics (e.g., area under the curve, AUC), without gaining new insight into the pathology itself. By disclosing the quantitated features, however, embodiments of HistoMapr reveal the pathological mechanisms underlying the decisions made by the xAI system. As such, embodiments of HistoMapr may allow researchers to understand new disease mechanisms that can lead to meaningful diagnostic or therapeutic advances.

Accordingly, in one aspect a method is provided for performing explainable pathological analysis of medical images. The method includes: for a region of interest (ROI) in a whole slide image (WSI) of a tissue, identifying features of several different feature types, where at least one feature type is at least partially indicative of a pathological condition of the tissue within the ROI. The method also includes classifying the ROI into a class within a number of classes of tissue condition, and (ii) designating to the ROI a label indicating a tissue condition associated with the class, where the label would then identify the condition of the tissue in the ROI. For the classification, a classifier that is trained to classify, using the features of the identified feature types, is used to classify a tissue image into one of the several classes of tissue conditions.

In addition, the method includes storing explanatory information about the designation of the label. The explanatory information includes information about the identified features. Furthermore, the method includes displaying: (i) at least a portion of the WSI with boundary of the ROI highlighted, (ii) the label designated to the ROI, and (iii) a user interface (UI) having: (a) a first UI element for providing to a user access to the stored explanatory information, and (b) one or more additional UI elements enabling the user to provide feedback on the designated label.

In some embodiments, the tissue includes breast tissue, and the classes of tissue conditions include two or more of: invasive carcinoma, ductal carcinoma in situ (DCIS), high-risk benign, low-risk benign, atypical ductal hyperplasia (ADH), flat epithelial atypia (FEA), columnar cell change (CCC), and normal duct. In some other embodiments, the tissue includes lung tissue, and the classes of tissue conditions include: idiopathic pulmonary fibrosis (IPF) and normal. In some embodiments, the tissue includes brain tissue, and the classes of tissue conditions include: classical cellular tumor and proneural cellular tumor.

the different feature types may include cytological features and/or architectural features (AFs). A cytological feature can be of a subtype such as: nuclear size, nuclear shape, nuclear morphology, or nuclear texture. An architectural feature can be of a subtype such as: an architectural feature based on a color of a group of superpixels in the ROI (AF-C); (ii) an architectural feature based on a cytological phenotype of nuclei in the ROI (AF-N); or (iii) a combined architectural feature (AF-CN) based on both a color of a group of superpixels in the ROI and a cytological phenotype of nuclei in the ROI. An architectural feature can also be of a subtype such as: nuclear arrangement, stromal cellularity, epithelial patterns in ducts, epithelial patterns in glands, cell cobblestoning, stromal density, or hyperplasticity.

In some embodiments, the information about the features includes one or more of: a total number of features types that were detected in the ROI and that correspond to the tissue condition indicated by the label; a count of features of a particular feature type that were detected in the ROI; a measured density of features of the particular feature type in the ROI; or a strength of the particular feature type in indicating the tissue condition.

The explanatory information may include a confidence score computed by the classifier in designating the label. The confidence score may be based on one or more of: a total number of feature types that were detected in the ROI and that correspond to the tissue condition indicated by the label; for a first feature type: (i) a strength of the first feature type in indicating the tissue condition, or (ii) a count of features of the first feature type that were detected in the ROI; or another total number of features types that were detected in the ROI but that correspond to a tissue condition different from the condition associated with the label.

In some embodiments, the method further includes, in response to the user interacting with the first UI element generating explanatory description using a standard pathology vocabulary and the stored explanatory information, and displaying the explanatory description in an overlay window, a side panel, or a page. The method may further include highlighting in the ROI, features of a particular feature type, that at least partially indicates the tissue condition indicated by the label, using a color designated to the feature type; and displaying the highlighted ROI in the overlay window, the side panel, or the page.

In some embodiments, the method includes repeating the identifying, designating, and storing steps for a plurality of different ROIs. In these embodiments, the method also includes, prior to the displaying step: (i) computing a respective risk metric for each of the ROIs, where the risk metric of an ROI may be based on: (a) designated label of the ROI, and/or (b) a confidence score for the ROI; and (ii) sequencing the ROIs according to the respective risk metrics thereof. In these embodiments, the displaying step includes: displaying in one panel: (i) at least a portion of the WSI with boundary of the ROI having the highest risk metric highlighted, (ii) the label designated to that ROI, and (iii) a user interface (UI) providing to the user access to the stored explanation for the designated label of that ROI. The displaying step also includes displaying in another panel thumbnails of the sequence of ROIs.

In some embodiments, the method includes obtaining the whole slide image (WSI), and identifying the ROI in the WSI. Identification of the ROI may include: (i) marking in the WSI, superpixels of at least two types, one type corresponding to hematoxylin stained tissue and another type corresponding to eosin stained tissue; and (ii) marking segments of superpixels of a first type to define an enclosed region as the ROI. The method may include identifying several different ROIs in the WSI.

In some embodiments, the method includes updating a training dataset for the classifier. Updating the training dataset may include receiving from the user via the one or more additional UI elements feedback for the label designated to the ROI, where the feedback indicates the correctness, as perceived by the user, of the designated label, and storing a portion of the WSI associated with the ROI and the designated label in a training dataset. The classifier can be a decision tree, a random forest, a support vector machine, an artificial neural network, or a logistic regression based classifier.

In another aspect, a method is provided for distributing cases among a group of pathologists. The method includes: for each one of several cases, processing a corresponding whole slide image (WSI) of a tissue, where the processing of the WSI includes: identifying one or more regions of interest (ROIs) in the WSI, where each ROI has designated thereto a respective diagnostic label indicating a condition of a tissue in the ROI. The diagnostic label may be generated by a classifier or may have been provided by a pathologist.

The method also includes, for each ROI, computing a respective confidence score for the respective designation; and computing for the WSI: (i) a severity score based on the respective diagnostic labels designated to the one or more ROIs in the WSI; and (ii) a confidence level based on the respective confidence scores for the one or more ROIs. In addition, the method includes storing as explanatory information, the severity score, the confidence level, and the respective confidence scores. The confidence score for an ROI may be computed for a label suggested by the platform or for a label that was provided by a pathologist.

The method further includes determining if the severity score is at or above a specified threshold severity score and, if so determined, transmitting the WSI to a rush pathologist in the group of pathologists, who may immediately (or with a high priority) review the WSI. The method includes, if the severity score is below the specified threshold severity score, determining if the confidence level is at or below a specified threshold confidence level and, if so determined, transmitting the WSI to a subspecialist in the group of pathologists; and otherwise, transmitting the case to a generalist pathologist in the group of pathologists. Thus, a subspecialist may be able to review relatively difficult cases with high priority. Transmitting the case to a general pathologist may include selecting the general pathologists from a pool of general pathologists within the group of pathologists such that upon transmitting the case to the selected general pathologist maintains a balanced workload for the pool.

In some embodiments, the method includes designating the respective diagnostic label to at least one ROI in at least one WSI. To designate the respective diagnostic label to a particular ROI includes: using a classifier, trained to classify an image, using features of several different feature types that are identified in the image, into one of a number of classes of tissue conditions, to: classify the ROI into a class within the number of classes of tissue conditions; and designate to the ROI a label indicating a tissue condition associated with the class. In some other embodiments, for at least one ROI in at least one WSI, the respective diagnostic label was provided by a prior reviewer, and the group of pathologists represents a group of subsequent reviewers.

In some embodiments, the method further includes: in response to a user requesting, via a UI element, an explanation for the transmission of a particular WSI: generating an explanatory description using a standard pathology vocabulary and the stored explanatory information, and displaying the explanatory description. The method may also include selecting from the particular WSI, an ROI for which the designated label indicates a severe condition or the confidence score is at or below a specified threshold confidence score. In addition, the method may include highlighting in the ROI, the features of a particular feature type, that at least partially indicates the tissue condition indicated by the label designated to the ROI, using a color designated to the feature type, and displaying the highlighted ROI along with the explanatory description.

The explanatory information may include, for a first ROI in a first WSI, one or more of: a total number of features types that were detected in the first ROI and that correspond to the tissue condition indicated by the label designated to the first ROI; a count of features of a particular feature type that were detected in the first ROI; a measured density of features of the particular feature type in the first ROI; or a strength of the particular feature type in indicating a corresponding tissue condition.

The confidence score for a first ROI in a first WSI may be based on one or more of: a total number of feature types that were detected in the first ROI and that correspond to the tissue condition indicated by the label designated to the first ROI; for a first feature type: (i) a strength of the first feature type in indicating a corresponding tissue condition, or (ii) a count of features of the first feature type that were detected in the ROI; or another total number of features types that were detected in the first ROI but that correspond to a tissue condition different from the condition associated with the label designated to the first ROI.

In another aspect, a method is provided for ground truth labeling of images used for training a classifier. The method includes: obtaining a whole slide image (WSI) of a tissue, and identifying one or more regions of interest (ROIs) in the WSI. The identification of an ROI includes: (i) marking in the WSI, superpixels of at least two types, one type corresponding to hematoxylin stained tissue and another type corresponding to eosin stained tissue; and (ii) marking segments of superpixels of a first type to define an enclosed region as the ROI. The method also includes displaying, in a sequence, one or more ROIs; and for each ROI: displaying one or more UI elements, where a first UI element can provide or affirm a respective ground-truth label to be assigned to the ROI. In addition, the method includes: in response to the user interacting using the first UI element, designating the respective ground-truth label to the ROI and storing the ROI in a training corpus.

In some embodiments, the first UI element indicates the user's agreement with a provided suggestion, and the method includes, for each ROI in at least a subset of the one or more ROIs: identifying features of several feature types, where at least one feature type is at least partially indicative of a pathological condition of the tissue within the ROI. The method further includes using a classifier, trained to classify an image using features of several different feature types into one of a number of classes of tissue conditions, to: (i) classify the ROI into a class within the plurality of classes, (ii) designate to the ROI a suggested label indicating a tissue condition associated with the class, and (iii) store explanatory information about the designation of the suggested label. The explanatory information includes information about the identified features. The method also includes displaying the suggested label as the provided suggestion.

The method may further include, in response to a user requesting, via a UI element, an explanation for the suggested label for a particular ROI: generating an explanatory description using a standard pathology vocabulary and the stored explanatory information, and displaying the explanatory description. In some embodiments, the method includes highlighting in the particular ROI, features of a particular feature type, that at least partially indicates the tissue condition indicated by the label designated to the ROI, using a color designated to the feature type, and displaying the highlighted ROI along with the explanatory description.

The explanatory information may include, for the particular ROI, one or more of: a total number of features types that were detected in the particular ROI and that correspond to the tissue condition indicated by the suggested label designated to the particular ROI; a count of features of a particular feature type that were detected in the particular ROI; a measured density of features of the particular feature type in the particular ROI; or a strength of the particular feature type in indicating a corresponding tissue condition.

The confidence score for the particular ROI may be based on one or more of: a total number of feature types that were detected in the particular ROI and that correspond to the tissue condition indicated by the suggested label designated to the particular ROI; for a first feature type: (i) a strength of the first feature type in indicating a corresponding tissue condition, or (ii) a count of features of the first feature type that were detected in the particular ROI; or another total number of features types that were detected in the particular ROI but that correspond to a tissue condition different from the condition associated with the suggested label designated to the particular ROI.

In another aspect, a system is provided for: (i) performing explainable pathological analysis of medical images; (ii) distributing cases among a group of pathologists; or (iii) ground truth labeling of images used for training a classifier. The system includes a first processor, and a first memory in electrical communication with the first processor, where the first memory includes instructions that may be executed by a processing unit that may include the first processor or a second processor, and that is in electronic communication with a memory module that may include the first memory or a second memory. The instructions program the processing unit to perform one or more of the operations according to the methods, and/or one or more steps thereof, that are described above.

Various embodiments described herein have several technical effects. For example, the accuracy of image analysis of whole slide images of tissue can be greatly improved, because the process of identifying regions of interest in a whole slide image scans the entire image, without omitting any portions thereof, and marks any region that may have a diagnostic condition associated therewith as a region of interest. Thus, the likelihood of missing a region of a whole slide image having a condition that should have been diagnosed is minimized, which can minimize the errors of missed diagnosis and can thus improve the quality of care by minimizing the risk of illnesses, serious health conditions, or complications that could arise from a missed diagnosis.

Moreover, because various embodiments described herein not only suggest a provisional diagnosis but also an explanation of how a particular diagnostic determination was made, these embodiments can improve the accuracy of the diagnosis and can also improve concordance among the reviewing pathologists. In addition, to suggest the provisional diagnosis various embodiments employ an artificial intelligence based system that can be trained on an on-going bases, especially when images for which there is a discrepancy between the provisional diagnosis and the final diagnosis performed by a reviewer. In some embodiments, the system itself facilitates the generation of ground-truth-labeled datasets that can be used for the initial and/or on-going training. This can further improve the accuracy of diagnosis.

Some embodiments can improve the accuracy of diagnosis in yet another way. In particular, these embodiments can distribute cases to reviewers, e.g., pathologists according to their expertise. This distribution can be performed as part of finalizing an initial diagnosis or, post final diagnosis, for quality checking and assurance. The distribution of cases to reviewers according to their expertise can also improve diagnostic accuracy because the specialists or subspecialists are not burdened with having to review straightforward cases, and may focus on hard to diagnose cases. Likewise, generalists or less experienced reviewers are not burdened with reviewing hard to diagnose cases, as their review can be erroneous or they may not be able to review such images at all. Moreover, cases requiring immediate attention because the underlying condition is serious, can be given such attention by directing them to reviewers tasked with reviewing such cases, which can also improve the quality of care.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will become more apparent in view of the attached drawings and accompanying detailed description. The embodiments depicted therein are provided by way of example, not by way of limitation, wherein like reference numerals/labels generally refer to the same or similar elements. In different drawings, the same or similar elements may be referenced using different reference numerals/labels, however. The drawings are not necessarily to scale, emphasis instead being placed upon illustrating aspects of the invention. In the drawings:

FIG. 13 shows a table of categories of tissue conditions that may be used by embodiments of an xAI platform;

FIGS. 21A-21F show a process of identifying features of a tissue image, where such features are used to determine a condition associated with the tissue, and where the determination can be explained using the features, using embodiments of an xAI platform;

FIGS. 22A1-22A12 show examples of different samples of lung tissue having different architectural features;

DETAILED DESCRIPTION

Pathology is considered a gold standard of medical diagnosis. Therefore, pathologists have been conservative about making large practice changes. There is substantial interest in computational pathology, but are concerns, as well, because any error made by a computer can pose a serious risk of harm to humans and even loss of life. It is likely that xAI can facilitate adoption of computational pathology because it would not only present a result efficiently, but would also explain how the result was obtained. A human, generally a pathologist, can then readily determine whether the computer-generated result should be accepted or whether further review is warranted. Explainable AI can also help drive scientific understanding of pathology underlying cancer and other diseases that have been elusive. It is important to note that our use of xAI is to support the pathologist in making efficient and more accurate "calls."

Figure 1A:
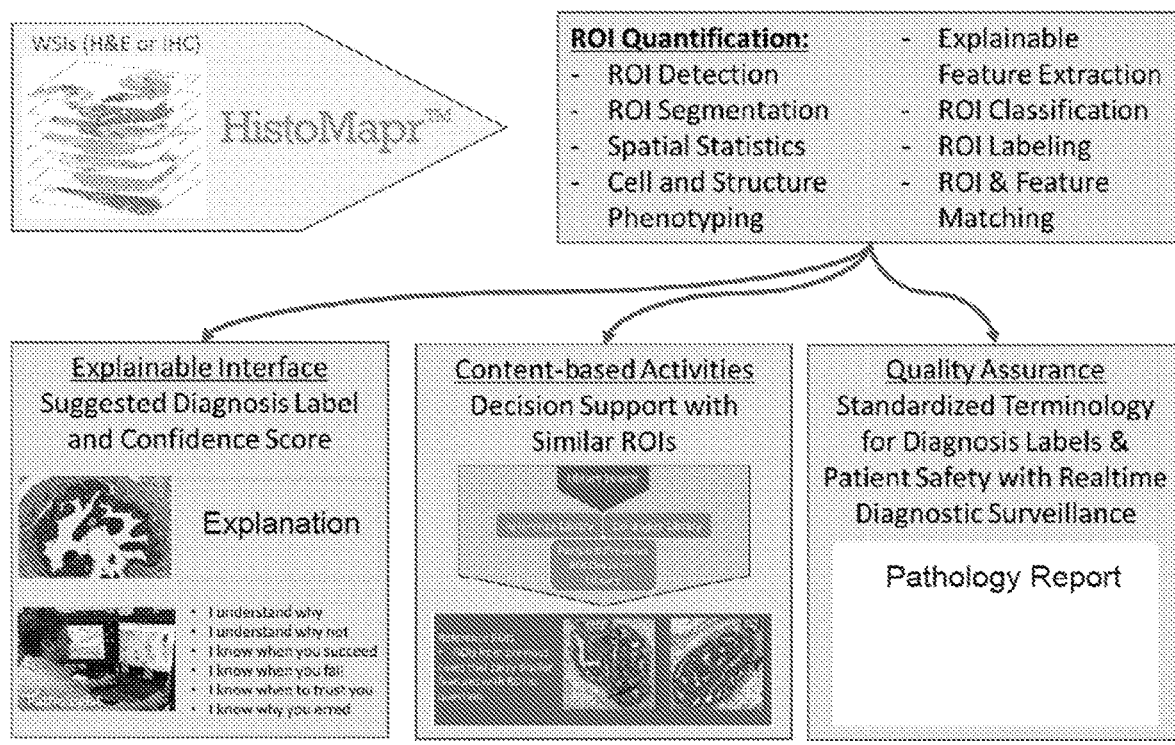
FIGS. 1A-1C schematically depict the use of an xAI-based platform in pathology, according to various embodiments.
Figure 1B:
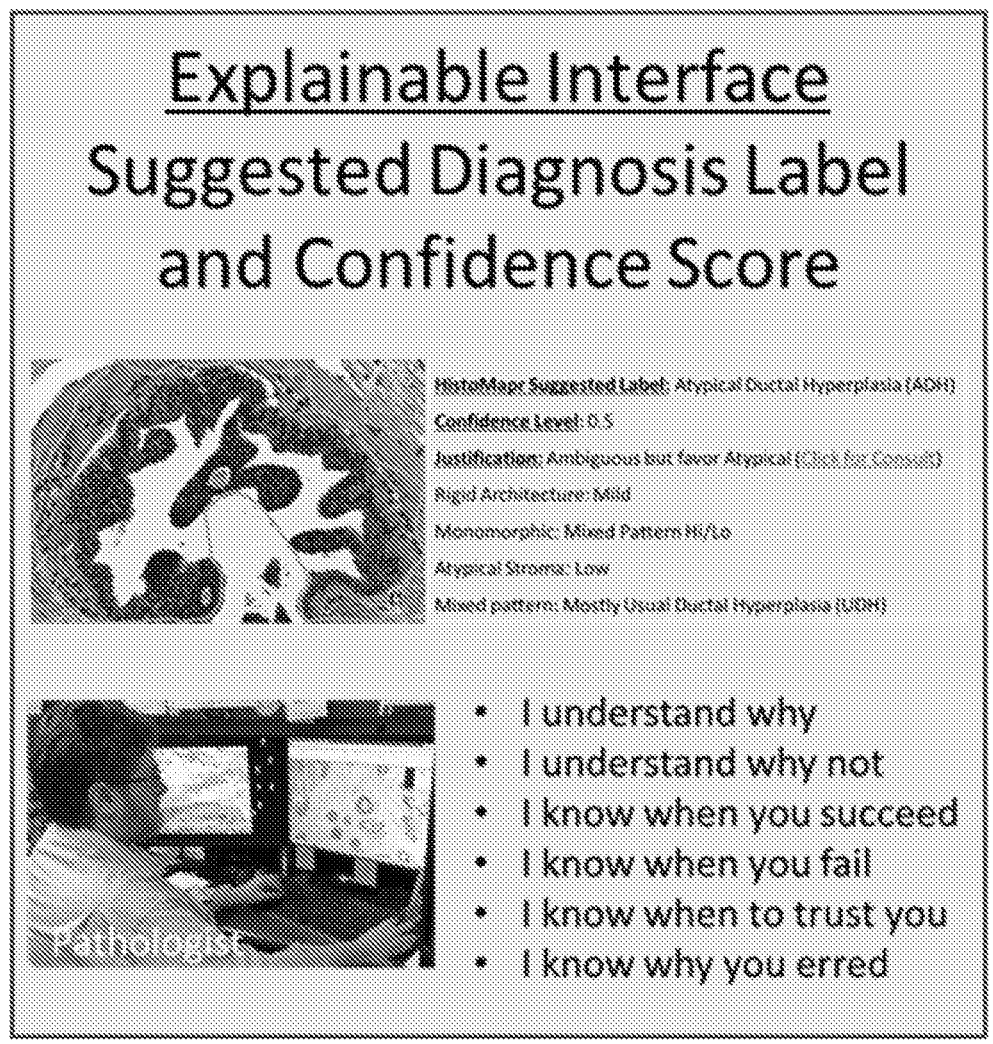
Figure 1C:
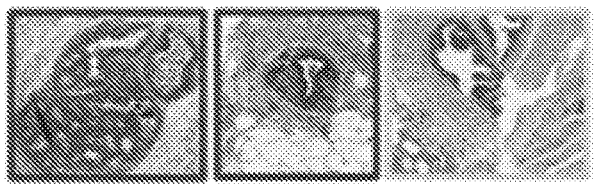

With reference to FIGS. 1A-1C, revelation of information leading to the decisions made by an embodiment of an xAI platform can make such a platform a critical feature of computational pathology. In general, in various embodiments HistoMapr xAI can lead to content-based image applications that are based on analyses of regions of interest ROIs. HistoMapr can analyze WSIs to discover one or more ROIs and then provide a diagnostic label to each ROI. HistoMapr can also generate descriptive information pertaining to bias, transparency, safety, causality, etc. HistoMapr may be used by pathologist to aid in diagnosis, where the descriptive information can provide a real-time explanation of the HistoMapr's analysis. Content-based image searching is also enabled in some embodiments, which facilitates several related activities such as decision support, education, or clinical trial screening (lower center). Finally, quality assurance activities may be facilitated and include ongoing monitoring by HistoMapr and pathologists, and improved reporting by promotion of standardized terminology.

Figure 2A:
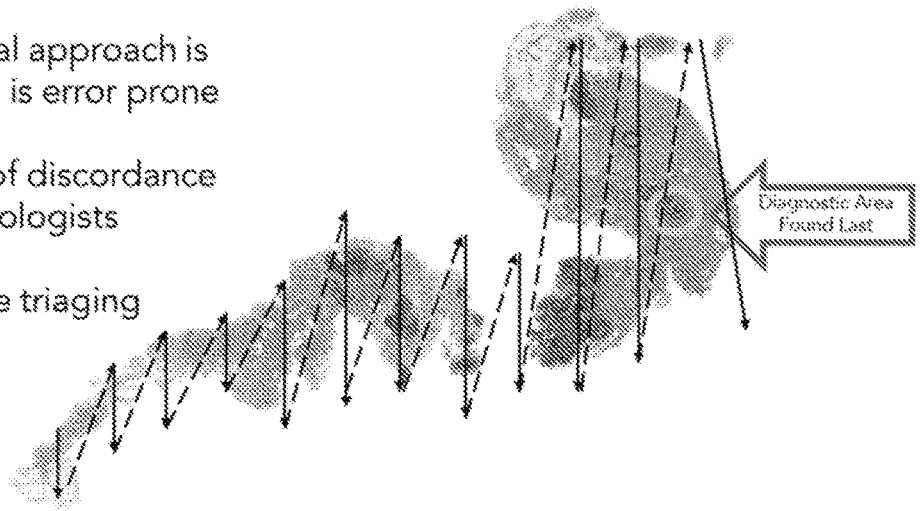
FIG. 2A illustrates a conventional process of analyzing a whole slide image.

With reference to FIG. 2A, traditional, manual pathology diagnosis, either with glass microscope slides or with manual WSIs, is often inefficient and error-prone. FIG. 2A shows a simplified, usual microscope or manual WSI 202 and a typical viewing pathway 204 (dashed and solid black arrows). Pathologists must view the tissue in a systematic fashion to ensure that all tissue was viewed. This can lead to an efficiency issue wherein the diagnostic area (circle 206), is discovered unpredictably and without warning. It could even be missed if small or subtle. The ongoing search for potential diagnostic areas is also slower than the confident review after decisions identifying the diagnostic areas of interest (or ROIs) have been made. Finally, there is no before-hand knowledge of whether an individual pathology case will be difficult, or whether it needs to be expedited.

As such, one group reported low diagnostic concordance between pathologists when diagnosing difficult lesions in breast biopsies such as atypical ductal hyperplasia (52% concordance). This report also noted that different kinds of pathologists (i.e. breast pathologists vs. general pathologists) were subject to different levels of performance. Regarding efficiency, manual WSI viewing may not provide adequate efficiency, versus traditional glass slide microscopy, to justify its implementation for primary diagnosis given the cost and workflow changes of WSI including time delay for slide scanning. This is based on unpublished data but is also borne out by the sluggish adoption of digital pathology for primary diagnosis in recent years despite a regulatory opening in 2017.

Figure 2B:
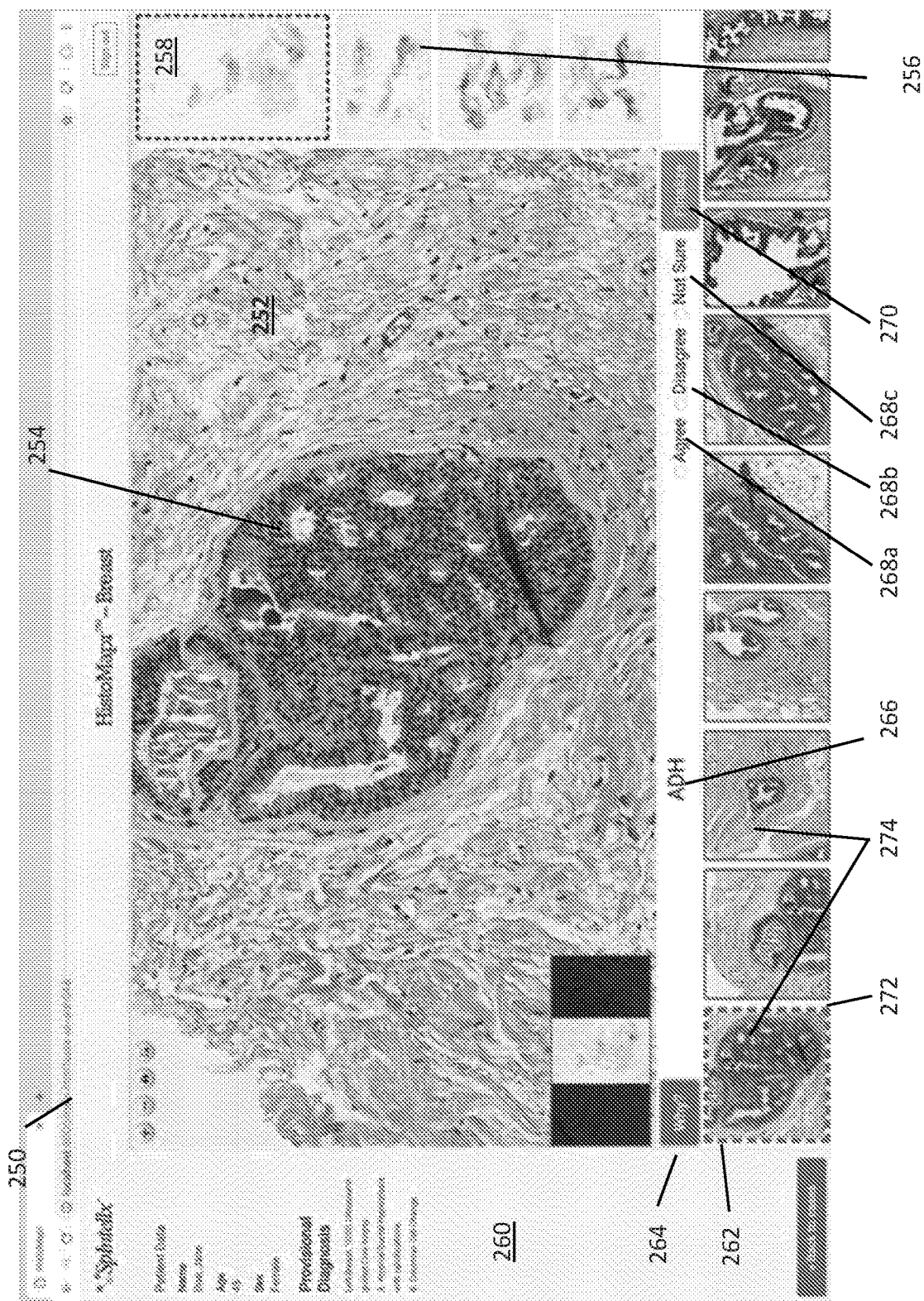
FIG. 2B illustrates typical pathological analysis that can be perform using an embodiment of an xAI platform.

FIG. 2B depicts an example display 250 of an embodiment of HistoMapr referred to as HistoMapr-Breast, which is configured to analyze breast tissue WSI. The central panel 252 shows the WSI viewing area with a computer-identified ROI boundary 254 in green. The boundary may be generated using other colors or techniques. The panel 256 to the right shows the WSIs 258 that have been analyzed and are available for viewing. The panel 260 to the left shows patient information and a provisional diagnosis produced by HistoMapr-Breast. The bottom panel 262 shows key elements of HistoMapr, including a "Why?" UI element (e.g., a button) for xAI 264, a HistoMapr diagnostic label 266 of "ADH" (atypical ductal hyperplasia), pathologist UI elements (e.g., buttons) 268a-c, to indicate agreement, disagreement, or uncertainty about the HistoMapr label, and a finalize UI element (e.g., a button) 270. Below the indicators and buttons, there is an ROI subpanel 272 showing the ROIs 274 triaged from most atypical to least atypical. The ROIs 274 are typically shown at a size smaller than the size of the ROI shown in the central panel 252. The ROIs 274 may also be shown as thumbnail images.

According to our simulations of a pCAD model, computational pathology, such as that facilitated by HistoMapr-Breast, can be 56% more efficient than traditional microscopy for breast core biopsies. Efficiency gains appeared to come from several factors, including earlier discovery of diagnostic regions of interest (ROIs); decreased uncertainty due to a triage effect; and ability to review less diagnostic ROIs in an expedited fashion after major diagnostic decisions were made.

Definitions

As used throughout the discussion below, the following terms can be generally interpreted according to their plain and ordinary meaning within the context of the field of computational pathology. The following descriptions of various terms is not necessarily limiting but can inform the plain and ordinary meaning.

Pathology case—This is a patient specimen that is submitted to a laboratory by a physician, such as a breast core biopsy or a collection of specimens such as a mastectomy with separate lymph node biopsies. These specimens, or cases are described and processed into glass microscope slides that may be subsequently imaged as whole slide images (WSIs). Pathologists view microscope slides and/or WSIs to make diagnostic decisions, which are then issued as a results report.

Digital pathology—This refers to the use of digital imaging in pathology. Initial efforts focused on remote viewing of microscopy with both manual and robotic remote-controlled microscopes, or basic image analysis including biomarker reads. Whole slide images (WSIs) are a more recent area of digital pathology, both for earlier applications (e.g. telepathology or image analysis) and for more recent primary diagnosis applications (i.e. replacement of microscopes). Computational pathology is a new form of digital pathology.

Computational pathology—This is the application of computing technologies, including machine learning or AI, to pathology data. This includes both image data such as WSIs, and non-image data such as patient demographics, clinical information, or pathologists' observations.

Artificial intelligence (AI)—The ability of a computerized system to perform tasks commonly associated with natural beings. The term is frequently applied to the project of developing systems endowed with the intellectual processes characteristic of humans, such as the ability to reason, discover meaning, generalize, or learn from experience.

Machine Learning—A computer science discipline in artificial intelligence research that is mainly concerned with the implementation of computer software that can learn autonomously. Expert systems and data mining programs are the most common applications for improving algorithms using machine learning.

Deep Learning (DL)—A part of a broader family of machine learning methods based on learning data representations, as opposed to task-specific algorithms. Deep learning algorithms imitate the workings of the human brain in processing data and creating patterns for use in decision making, by utilizing a hierarchical level of artificial neural networks. Deep learning enhanced programs are usually called "black box" in machine learning where even their designers cannot explain why the AI arrived at a specific decision.

Computer assisted diagnosis for pathologists (pCAD)—A conceptual framework that lays out a path forward for applying computational pathology to real-world practice. The intent is to augment pathologists with intelligent computer guidance that allows pathologists to delegate everything possible, so that they can focus on the critical decisions that only pathologists can make. This requires high level integration of pathology case information, highly detailed clinical situation plans, and computational pathology pipelines. HistoMapr represents an early iteration of this type of intelligent guide.

Pointwise Mutual Information (PMI)—Two-dimensional maps, defined by the total number of cellular phenotypes, for recording the relative co-occurrences and anti-associations of spatially distributed cellular phenotypes in a tissue sample. A PMI map with strong diagonal entries and weak off-diagonal entries describes a tumor sample that is locally homogeneous but global heterogeneous with respect to the spatial distribution of the cellular phenotypes. PMI maps with strong off-diagonal entries describe a tumor with many localized interactions between different cellular phenotypes, thus signifying a tumor sample exhibiting strong local heterogeneity.

Explainable artificial intelligence (xAI)—Also known as Transparent AI, or Interpretable Machine Learning, is an artificial intelligence whose actions can be trusted and easily understood by humans. xAI algorithms are programmed to describe its purpose, rationale and decision-making process in a way that can be understood by the average person. xAI is often discussed in relation to deep learning and plays an important role in the FAT ML model (fairness, accountability, and transparency in machine learning). Although the term xAI is usually used for explaining black-box DL tools, it is not limited to FL tools, and applies generally to machine learning, including AI algorithms, and can generate human-understandable statements describing the inferences and intermediate and final conclusions of the machine learning/AI processes.

HistoMapr and xAI

Figure 3:
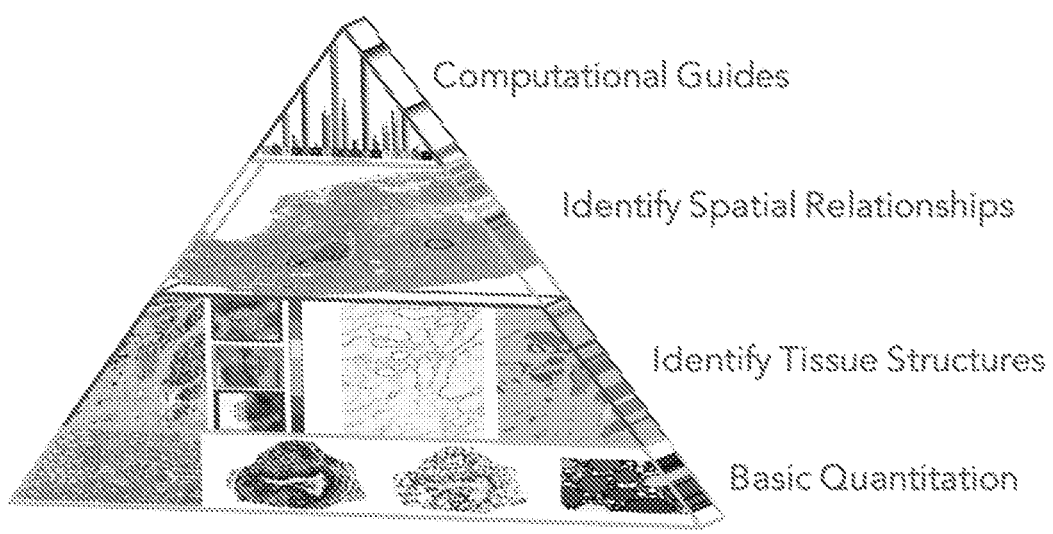
FIG. 3 shows the natural hierarchies found in the spatial organization of a tissues, where such hierarchies are used in the analysis performed by various embodiments of the xAI platform.

To address the unmet needs of efficiency and accuracy in pathology diagnosis, and to accelerate the adoption of computational pathology in pathology practice we have developed an xAI platform called HistoMapr™. HistoMapr-Breast, described above with reference to FIG. 2B, is one example of the HistoMapr platform. In various embodiments, HistoMapr echoes the natural hierarchies found in the spatial organization of human tissues, as illustrated in a pyramidal diagram shown in FIG. 3. At the lowest level, simple image analyses, such as nuclear size/shape determination, mitosis counting, color optimization, etc., is performed. This analysis can be integrated with pointwise mutual information (PMI) maps at the second level to identify and classify potential features in the WSIs, e.g., tissue structures such as ducts in breast tissue, inflammatory infiltrates, or tumor and their locations within regions of interest (ROIs).

Diagnostic labels for the regions of interest (ROIs), where the labels are based upon the tissue structures' spatial relationships and/or cell populations are identified at level three, and the ROIs are labeled with such diagnostic information, also at layer/level 3. The labeled ROIs may then be triaged based on diagnostic significance at layer/level 4. In this fashion, the xAI HistoMapr guides emerge; WSIs are represented as a guided review of triaged ROIs in the context of the pathologist's diagnostic tasks. Additional details about the various steps in this process and the manner in which analyses are performed at various levels are provided in Appendix A below.

By including relationships between distinct cellular populations of the tissue microenvironment (e.g., tumor, stromal and immune cells), various embodiments of HistoMapr enable precision medicine approaches to be incorporated into routine diagnostic and prognostic activities. As an example, breast core biopsies can be difficult for pathologists to diagnose concordantly. Therefore, we created an embodiment of HistoMapr, HistoMapr-Breast (discussed above with reference to FIG. 2B), that is directed to analyzing WSI of breasts. HistoMapr-Breast can analyze an entire breast core biopsy that may include one or more WSIs, using both basic image analyses and PMI maps to locate regions of interest (ROIs) that contain diagnostic breast tissue structures such as ducts, blood vessels, or stromal infiltrates.

Figure 4:
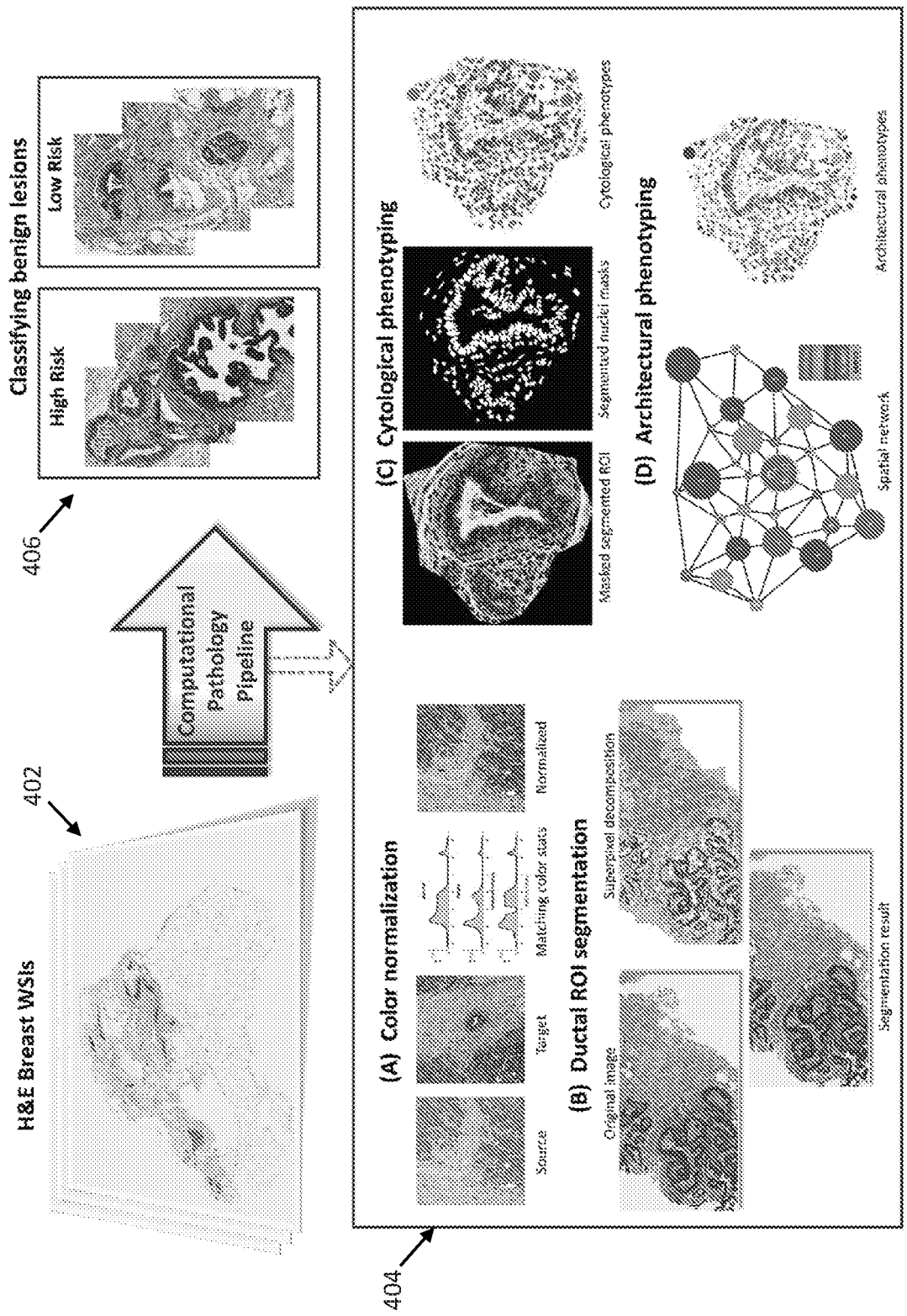
FIG. 4 shows a pipeline of the analysis performed by an xAI platform, according to some embodiments.

Specifically, FIG. 4 shows a computational pathology pipeline for an embodiment HistoMapr-Breast, which features an end-to-end high-risk benign breast lesion detector for WSIs. From the WSIs received at step 402, a WSI is selected and analyzed in step 404. In particular, WSI stain color normalization is performed in substep (A), followed by ductal ROI segmentation in substep (B). Cytological and architectural feature extraction (phenotyping) are performed in substeps (C) and (D), respectively, leading to ductal ROI classification in step 406, where each region may be labeled as or identified as high risk or low risk.

In some embodiments, HistoMapr-Breast analyzes the ROIs to find pre-trained features and quantitate them if present. This analysis may be used to label the ROIs with diagnostic terms such as "atypical ductal hyperplasia," "invasive carcinoma," etc. This labeling is based on an analysis of the patterns and strengths of architectural features, where the strength can indicate how strongly discriminative a particular feature is. HistoMapr can also indicate its confidence in the label using a confidence score that incorporates the features and feature quantities. The labeled ROIs may then be triaged based upon both the diagnostic labels and the confidence scores of those labels.

Figure 5:
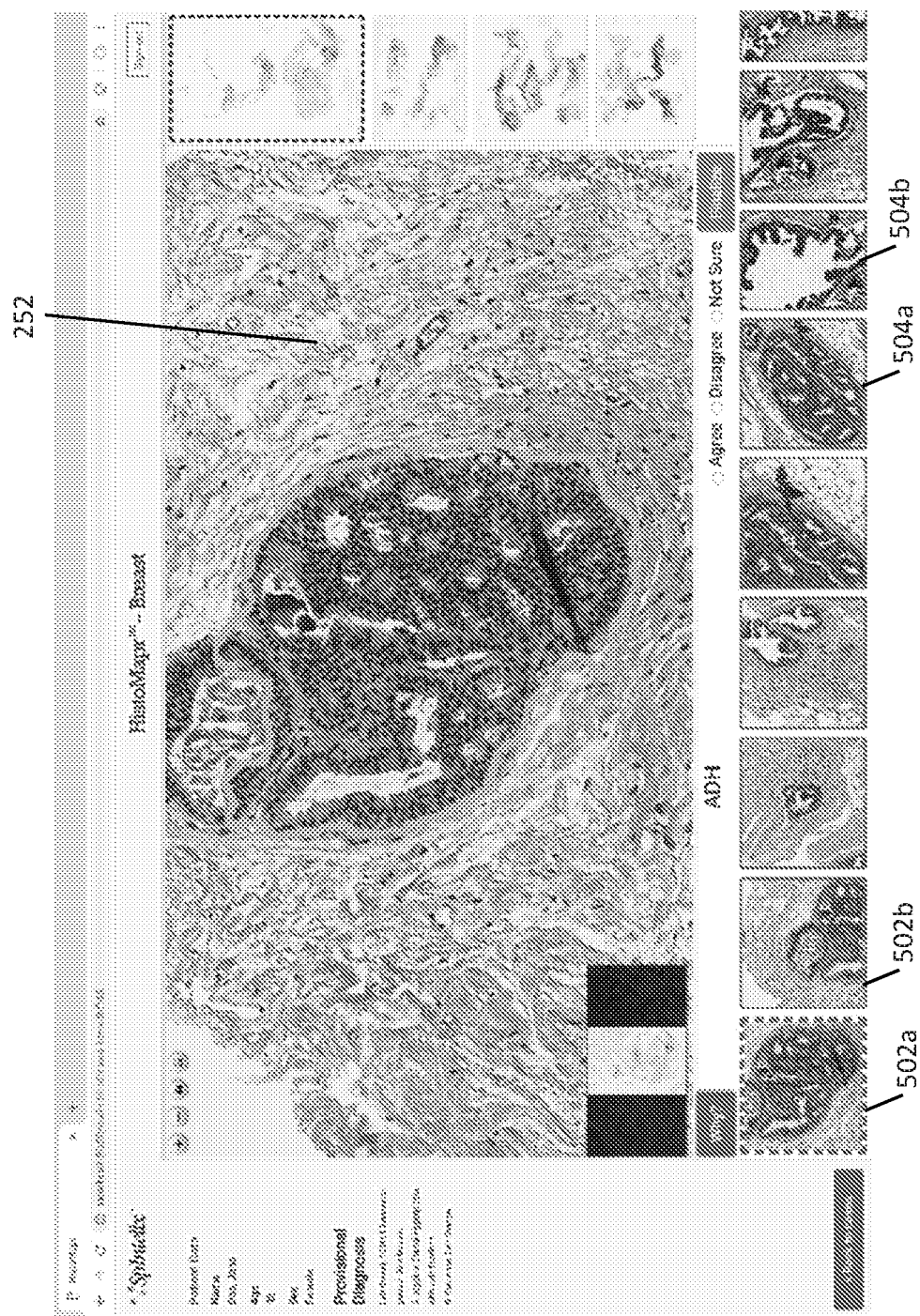
FIG. 5 illustrates pathological analysis that can be perform using an embodiment of an xAI platform.

For example, ROIs may be sorted from benign to malignant, or if cancer is not present, then from benign to atypical. Within a diagnostic category, ROIs can be triaged based on the confidence score. These steps occur before the pathologist begins viewing the case, possibly overnight or during weekend off hours. Using a pathologist-centric interactive interface, HistoMapr can display the ROIs in the triage order, so that the pathologist sees the most malignant or most atypical areas first, if present, as shown in FIG. 5 (which is same as FIG. 2B). Specifically, in some embodiments, the ROIs are sorted using a risk metric in a way such that high risk ROIs 502a, 502b, are shown to pathologist first, followed by lower risk ROIs 504a, 504b, in the bottom subpanel 272 of HistoMapr-Breast. The ROI associated with the highest risk is shown first, in the central panel 252. Critically, at any time the pathologist can be fully in control and may take manual control of the WSI viewer system. The risk metric for a particular ROI may be based on the severity of the label assigned to the ROI, a confidence score corresponding to the labelling, difficulty or uncertainty in deriving the ROI, or a combination of two or more of these factors.

Figure 6:
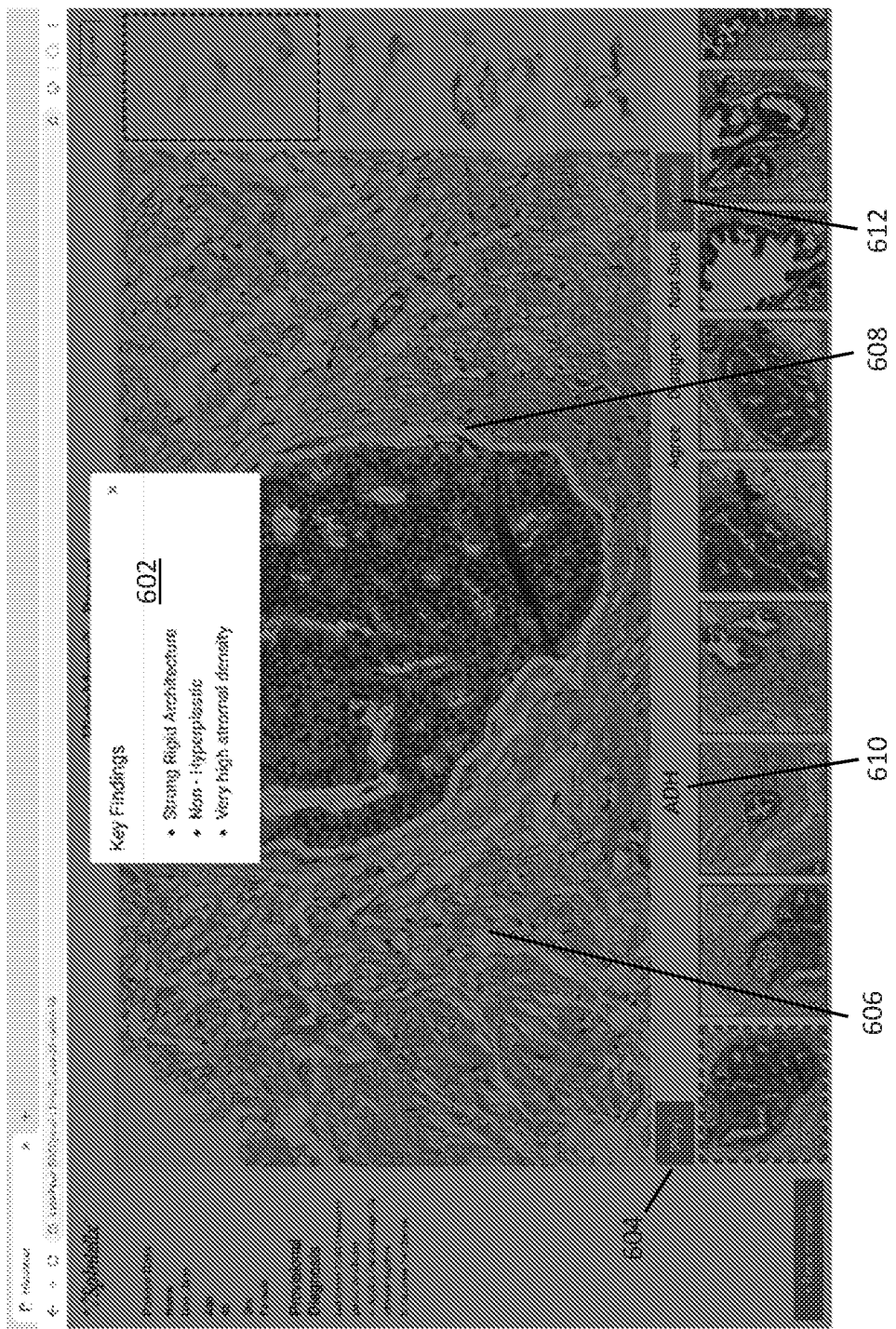
FIG. 6 shows an example of displaying the information justifying the analysis performed by an xAI platform, according to one embodiment.

With reference to FIG. 6, the xAI aspect of various embodiments manifests as a "Why?" button that provides one or more panels of supplementary information about how the AI arrived at a particular decision. Pathologists can interpret the xAI output by accessing an interface panel 602 or a page (not shown) by clicking a "Why?" or "Explain" button 604. The display panel 606 of HistoMapr-Breast xAI system shows the green bounded region of interest 608, that is classified as "ADH" 610. Clicking the button 604, named "Why?," opens the explanation panel 602, named "Key Findings", where justifications from the ROI in question are shown to the pathologists as why the xAI system decided to classify this region as ADH. In general, these justifications are based on information about the features identified in the ROI. This information includes the types or kinds of features identified, their strengths in determining the chosen labeling, counts of features of different types, types and/or counts of features suggesting a different labeling, etc. The justification may be displayed using the feature information and a standard vocabulary generally understood by pathologists.

In the example discussed herein, the justifications includes: (i) strong evidence of a rigid architecture; (ii) a determination that the detected tissue is non-hyperplastic; and (iii) has very high stromal density. In some cases, the strength of the rigidity may be quantified, e.g., on a numerical scale or as a percentage relative to a norm. Likewise, the stromal density may also be quantified. In addition, a confidence score, determined using t-values or z-values and indicating the confidence of the xAI in labeling the ROI, may also be presented.

The pathologist thus may have complete situational awareness and is thus able to make the very best diagnostic decisions. Embodiments of HistoMapr also facilitates the pathologist's work by managing diagnostic information and tracking the pathologist's agreement or disagreement with the provided diagnostic labels. The pathologist may also indicate uncertainty, and some embodiments of HistoMapr collect this information for possible additional stain work-up or consultation. When the pathologist is ready to finalize the case, he or she may press the "Finalize" button 612 and, in response, HistoMapr can automatically construct a results report using the pathologist's interpretations of the ROIs review, and also using suggested/standardized terminology. In one study, embodiments of HistoMapr-Breast performed well and showed 83% f-measure concordance for atypical ductal hyperplasia (N=300 WSIs and approximately 2,000 ROIs).

Figure 7:
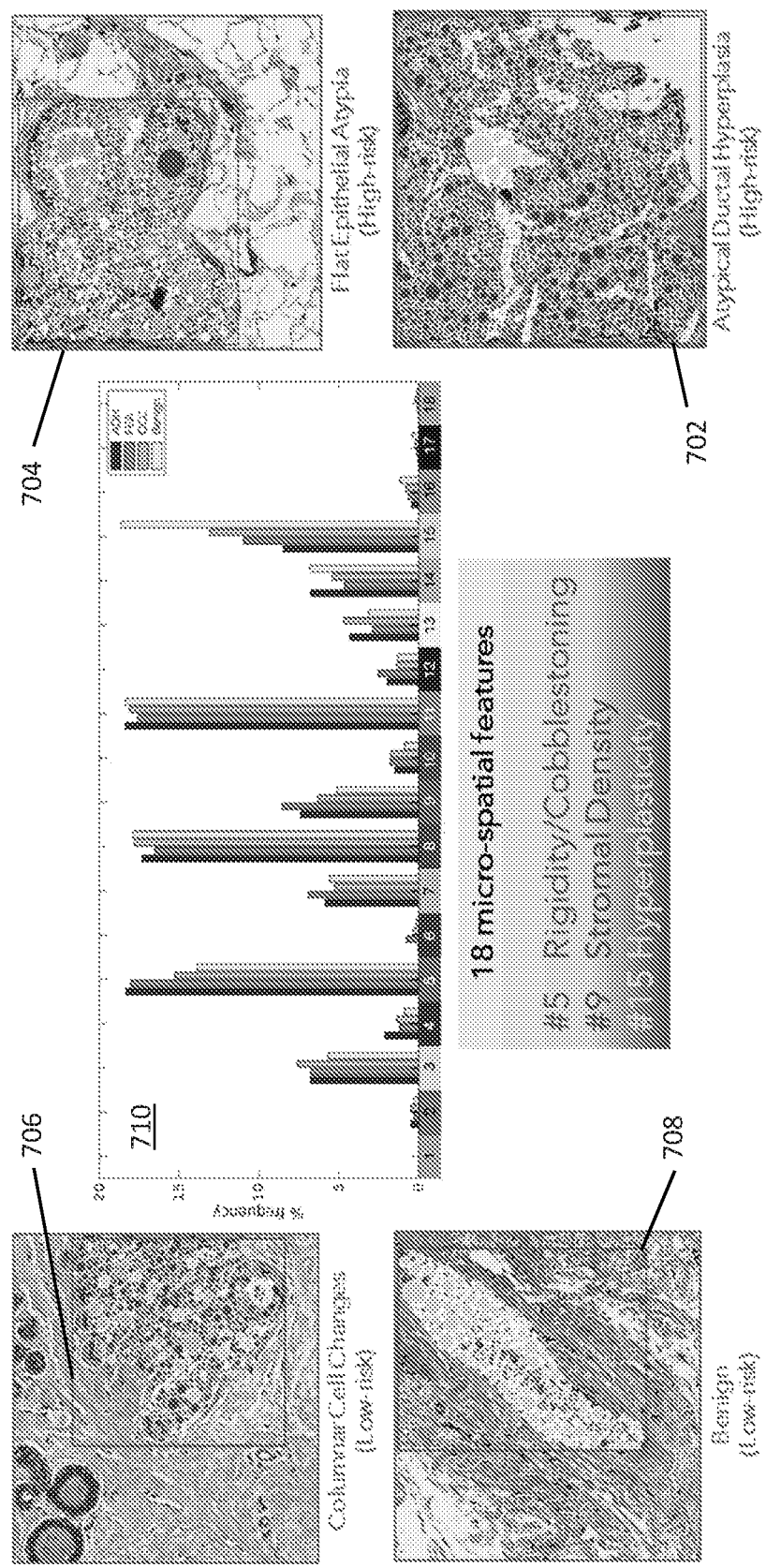
FIG. 7 shows an example of the features of an image that relate to different tissue conditions, where such features are used by an embodiment of an xAI platform.

FIG. 7 shows micro-spatial discriminant features in breast ROIs that are identified by an embodiment of HistoMapr-Breast. HistoMapr identified four ductal ROIs representing: (A) atypical ductal hyperplasia (ADH) 702, (B) flat epithelial atypia (FEA) 704, (C) columnar cell change (CCC) 706, and (D) normal duct 708. HistoMapr-Breast provided a visualization of the architectural patterns that it discovered in the ROIs, and overlaid those patterns on the original image, as can be seen in the ROIS 702-708. The patterns are derived from a combination of cytological and architectural features that are visualized as color coded objects. A total of 18 distinct features were identified in each of the four ROIs, and a distinct color was assigned to each object, as shown on the x-axis of histogram 710.

Note the relatively higher population of pattern #5 in ADH 702, pattern #7 in FEA 704, and pattern #15 in normal duct ROI 708. As used herein, the term relatively higher population of a pattern in an ROI generally means that a pathologist or a trained technician can see that that particular pattern is occurring more frequently relative to a normal or a baseline ROI. Relatively higher population of a pattern does not necessarily mean that that pattern occurs more frequently than any other pattern in the ROI to be evaluated. This observation is supported by the histogram 710, where we measure relative proportions of architectural patterns separately in each one of the categories: ADH, FEA, CCC, and normal duct. These architectural patterns are generally named based on the visual properties they are representing by our expert pathologists.

In addition to pathologist guides, embodiments of HistoMapr also includes features for additional applications/uses, such as ground truth data labeling, image-content based distribution of pathology work, and archival of key diagnostic information for longitudinal continuity of care or clinical research, as depicted in FIGS. 1A-1C. Ground truth data labeling is necessary for machine learning training but has historically been a bottleneck. Poorly implemented labeling tools can also squander scarce pathologist time.

Some embodiments of HistoMapr can effectively address this with both automated ROI discovery and with the pathologist-friendly interface. As discussed above, embodiments HistoMapr can analyze one or more WSIs and extract ROIs from each one. Using an efficient interface, pathologists can rapidly apply diagnostic labels to the identified ROIs. In some experiments pathologists were able to label approximately 1,000 ROIs identified by an embodiment of HistoMapr in one hour.

Figure 8:
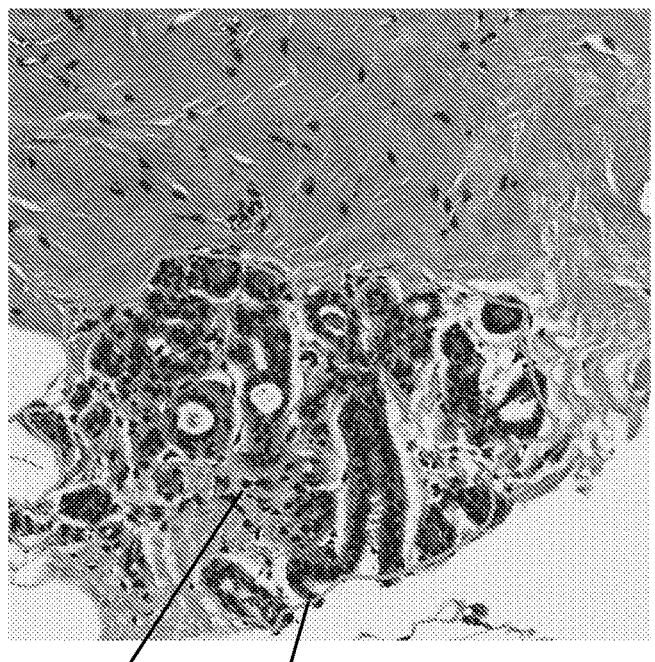
FIG. 8 shows an example graphics user interface (GUI) that may be used for ground-truth labeling, so as to generate a training corpus for training embodiments of an xAI platform.

FIG. 8 depicts a pathologist-centric graphic user interface (GUI) for collecting annotations from segmented regions of interest. We employ a GUI in Java environment to be easily used in any operation system, since an embodiment of HistoMapr may be used in pathologists' workstation or personal computer. The GUI can be implemented using any other programming language or scripting language, however. In some cases, a HistoMapr embodiment is a plug-in and play system, installed in an encrypted USB drive together with ROI images to be labeled. The GUI design for ground truth annotation is easy to learn and efficient to use. Pathologists do not need to hand-draw or type their inputs. Instead, they are shown a series of ROIs, one ROI 802 at a time, and are asked to hit a keyboard or display button from a group of buttons (not shown) to classify the shown ROI. In one example, the pathologist is asked to hit one of the buttons from 1 to 5, each corresponding to labels "benign", "high-risk benign", "DCIS", "Invasive carcinoma", and "Other".

Each ROI 802 is shown with a green segmentation boundary 804, to collect feedback from pathologists about the quality of the segmentation results produced by the embodiment of HistoMapr. For example, the option "Other" may be used by pathologists in case they could not decide the nature of the ROI shown or determined that there is a problem with the identified segmentation boundary 804. The pathologists may be asked to complete sets of 250 ROIs at a time, with an option of saving to be able to continue the process later. A relational database may then be created to store, manage, and retrieve the ground truth annotations, i.e., labelled ROIs. The labelled ROIs may be used as a training dataset to train embodiments of HistoMapr. During diagnostic use, the corrected labels derived during diagnostic work can also be included in the training dataset and used to improve HistoMapr based on real-world pathology diagnoses.

In some embodiments, the previously mentioned confidence scores are automatically generated by HistoMapr during WSI preview and analysis. Aggregated confidence score data associated with different ROIs can then be used to estimate the difficulty of a case, and also combined with the number of ROIs to estimate the amount of worktime required to view the case. This permits work triage based upon case attributes; difficult cases might be assigned to an expert subspecialist pathologist rather than a generalist pathologist. Pathology work may also be distributed evenly to a pool of pathologists, thereby improving efficiency of pathologist time utilization.

The xAI derived statistics of ROIs or of entire cases are a fingerprint of sorts that can also be used for other content-based purposes. The statistics include features present, quantitation of those features, and/or confidence scores. In general, a confidence score is the confidence in the diagnostic label. The diagnostic label is generally based on quantitated features, where each feature's quantitation score may contribute to the confidence score. The confidence scores permit matching of an ROI with libraries of known diagnostic images for decision support, for education, for quality assurance activities, or for image content searching and retrieval. Content-based analysis can also facilitate clinical trials by supplementing or automating patient screening and/or central review of the pathology.

Finally, as noted above in the xAI discussion of causality, in some embodiments, archived HistoMapr information may be used to facilitate subsequent re-visiting of a prior biopsy case. This includes comparison of older biopsies with newer materials or centralized review for clinical trials. Pathologists can readily view the diagnostic ROIs without need to manually search through the WSIs. Previously recorded computational features may also play a role in research where diagnostic entities are re-evaluated for risk or diagnostic criteria.

Some embodiments of HistoMapr are designed for transmitted light applications where tissue samples are stained with Hematoxylin and Eosin (H&E), immunohistochemistry (IHC) labels, and/or other stains (e.g. special stains, chromogenic in situ hybridization, enzyme metallography, etc.). A companion platform of intelligence guides for multiplexed-to-hyperplexed fluorescence, called TumorMapr™, is also provided in some embodiments.

Summary of Features of the Explainable AI/HistoMapr

In various embodiments, HistoMapr can effectively change pathologists' view of a case from one or more WSIs into a guided series of triaged, diagnostically relevant regions of interest (ROIs). HistoMapr previews entire WSIs to discover relevant structure/features. For breast core biopsies, HistoMapr-Breast finds ducts, vascular structures, and stromal features using spatial statistics based on pairwise mutual information (PMI). By analyzing PMI maps, HistoMapr can find ROIs that contain these structures. In some cases, an ROI represents a single structure. Impactful ROIs are typically smaller with fewer structures, and less diagnostic ones (i.e., those at the end of triage list) may represent several lumped together benign ROIs for purpose of expedited viewing of easier/benign ROIs. Once ROIs are identified, HistoMapr then analyzes them for certain features. For example, an embodiment of HistoMapr-Breast used 18 features to classify ROIs as atypical or not atypical (FIG. 7). Each of these classes may include two or more subclasses and the HistoMapr, in general, may classify an ROI into one or more subclasses.

In general there would be several features in a set of features, and the machine learning process itself can determine that a subset of these features can reliably indicate the conditions of interest. In one embodiment of HistoMapr, from a total of 33 features considered, 18 features were AI-discovered as significant, and 3 of them were most informative. The other 15 features played some role but were not as impactful as the others. In this analysis, HistoMapr finds which features are present in an ROI, and it quantitates each feature that it finds. The ROI analyses are patterns that can be matched to HistoMapr's library of diagnostic labels. The combination of diagnostic labeling and ROI quantitation is then used to triage the ROIs. Thus, for Each ROI, a feature vector would be generated. For example, each element of the vector may include the counts of a particular feature in the ROI. A machine-learned classification or predictor function would be applied to classify the ROI, e.g., as ADH, FEA, CCC, and/or normal. Each ROI designated only one classification or, in some cases, one or more ROIs may be designated a number of classifications, each with a likelihood score. in borderline ROIs, i.e., when the likelihood scores for two or more possible diagnoses are similar, HistoMapr might present a best-fit diagnosis together with other diagnoses that are also nearly probable. Based on the severity of the class to which a particular ROI is determined to belong, the ROIs would be triaged. For example, ROIs classified as ADH would be shown to the pathologist first.

For breast core biopsies, HistoMapr-Breast can triage ROIs in a clinical spectrum from invasive cancer at one end, to low-risk benign at the other (FIG. 5). In an interactive work session, the pathologist reviews the entire case, ROI by ROI, in a triaged fashion. This approach is highly efficient because HistoMapr presents the most clinically impactful ROIs to the pathologist first; this guidance enables the pathologist to focus on the hardest decisions first. If necessary, HistoMapr also keeps track of ROIs that may need further workup with additional stains, or ROIs that may require consultation with another pathologist.

HistoMapr can also expedite ground truth data labeling for training the machine learning. Pathologists can rapidly view ROIs and provide streamlined diagnosis labels. This unique approach can provide hundreds of labeled ROIs per hour. In automating ROI discovery, HistoMapr is much more efficient than traditional ground-truth labeling and effectively addresses what was a bottleneck in machine learning. Specifically, ROI discovery can be used in generating labelled datasets for training the xAI system. Also, depending on what labels the pathologists have assigned, the xAI system can determine if the training dataset is biased. HistoMapr has a pathologist-centric graphical user interface (GUI) for efficient annotation of segmented ROIs, which employs a GUI that can be implemented on the pathologists' workstation or personal computer. The GUI design for ground truth annotation is easy to learn and efficient to use (FIG. 8). Pathologists do not need to hand-draw or type their inputs; instead they are shown a series of ROIs and asked to choose from one of the labels: "benign", "high-risk benign", "DCIS", "Invasive carcinoma", and "Other". The ROIs may be shown with a green (or another suitable color) segmentation boundary to collect feedback from pathologists about the quality of the segmentation results. The option "Other" may be used by pathologists in case they cannot decide on the label of the ROI or there is a problem with the segmentation boundary. The pathologists can be asked to complete sets of 250 ROIs (or another suitable number, e.g., 50, 100, 300, etc.) at most at a time, with an option of saving their progress to be able to continue later. HistoMapr has a database to store, manage and retrieve the ground truth annotations. In some experiments, pathologists were able to label around 1000 ROIs in an hour after getting used to the platform.

Explainable AI (xAI): Analysis of HistoMapr output generally yields multiple features (with quantitation of those features) that can be described in pathologist-friendly language, thereby linking impactful features with diagnostic labels that can be used to explain HistoMapr labels in subsequent clinical sessions, providing pathologists with all the information that they need to make the best decisions possible. In one study, using the computational pathology pipeline (FIG. 4), we extracted and then triaged breast duct regions of interest (ROIs) in breast core biopsies as atypical vs not atypical (n=46 cases). For this, 269 deidentified whole slide images (WSIs) were created (using 20×, ScanScope XT, Leica Biosystems, Buffalo Grove Ill. USA). The AI used a combination of nuclear morphology and architectural arrangement to create 18 micro-spatial duct features that described 95% of the training set (1009 ROIs) (FIG. 7). ROIs were reviewed in the context of the 18 features, especially features 5, 9 and 15 which were differentially seen in atypical vs. non-atypical ducts (as also seen in the histogram 710 in FIG. 7). Feature 5 appeared to correlate with architectural rigidity and cobblestoning of cells; feature 9 appeared to represent stromal density immediately surrounding ducts; and feature 15 seemed to correlate with hyperplasticity of the duct. Using this information, an embodiment of HistoMapr incorporating xAI was created. This embodiment provides an AI feedback overlay, automatic presentation of feature examples, etc. (FIG. 7).

xAI visualization in real-time: A "Why?" user interface (UI) button can provide complete transparency by presenting additional information in real-time that explains HistoMapr's labels, fleshes out the relevant differential diagnosis, where the xAI determined that a particular ROI was ambiguous and designated two or more labels thereto, for a final determination by a pathologist, and acknowledges the strength of HistoMapr's analysis via one or more confidence score. HistoMapr can display the results of its ROI analysis to the pathologist. An embodiment of HistoMapr-Breast includes the "why?" button (FIG. 6). As previously mentioned, HistoMapr finds and then quantitates features in the ROIs. When the pathologist presses the "Why?" button, she or he can see a visualization of the ROI analysis by HistoMapr, in pathologist-friendly language (e.g., using terms such as strong rigid architecture, highly monomorphic nuclear patterns, etc.).

Figure 9:
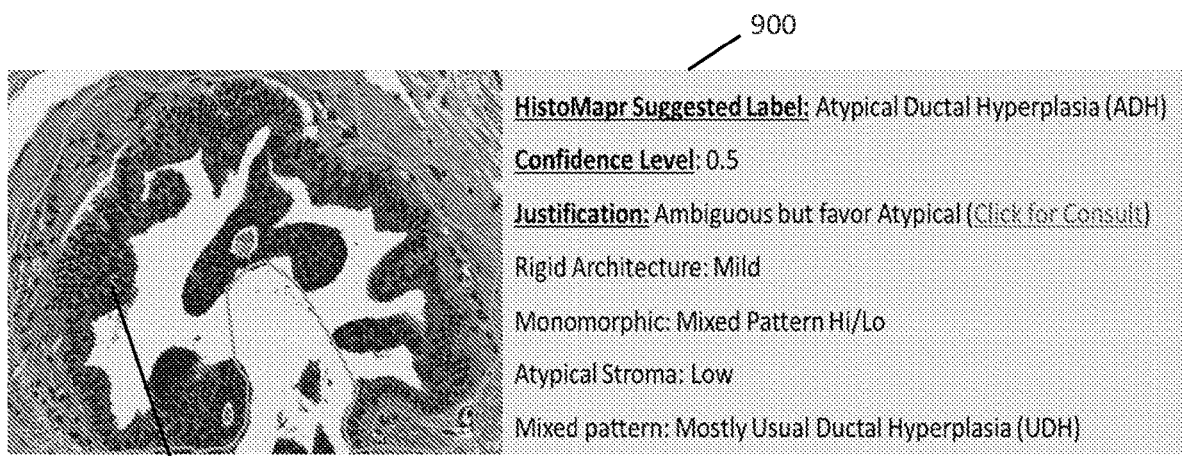
FIG. 9 shows another example of displaying the information justifying the analysis performed by an xAI platform, according to one embodiment.
Figure 10:
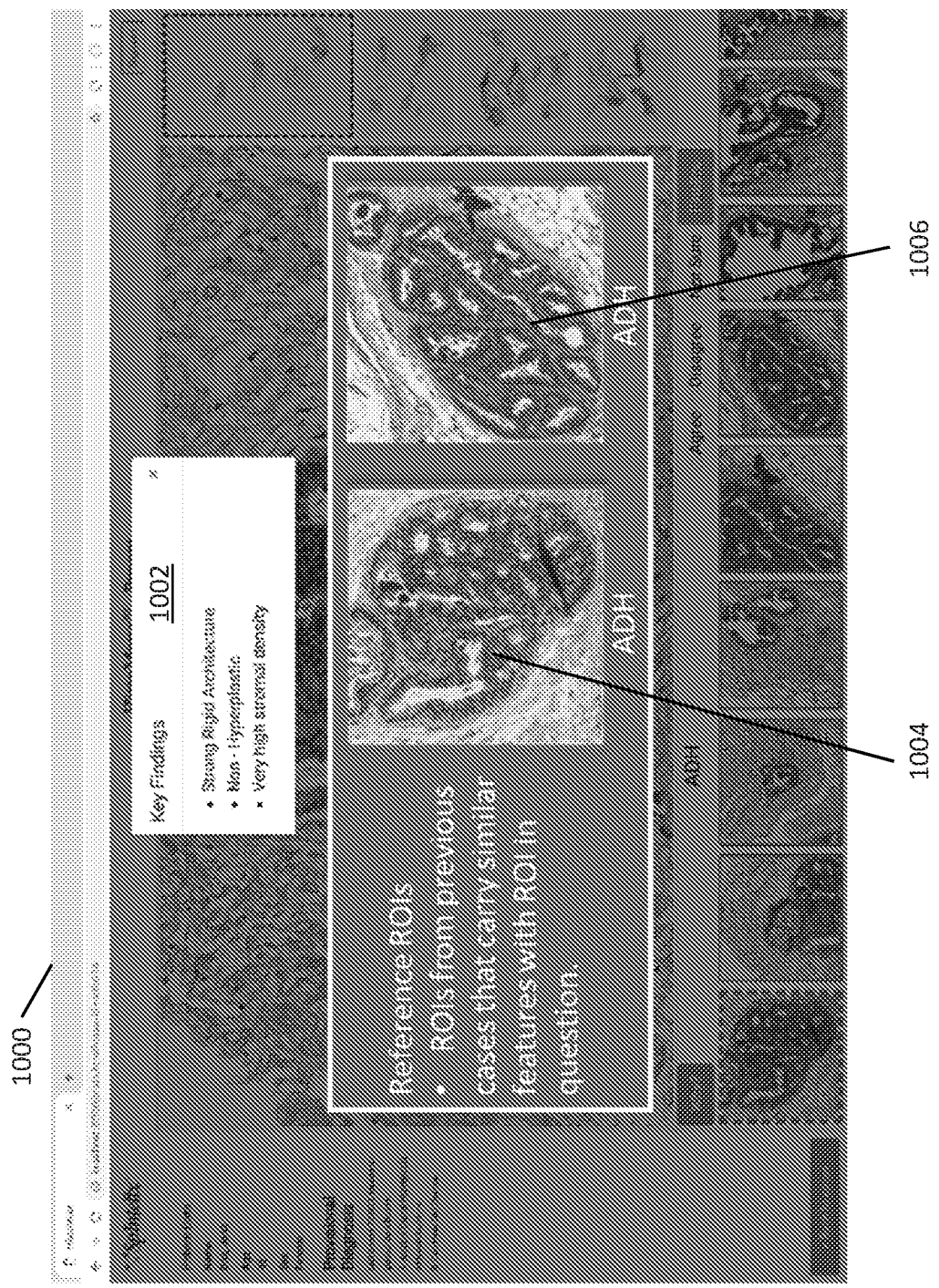
FIG. 10 shows yet another example of displaying the information justifying the analysis performed by an xAI platform, where the displayed information includes regions of interest similar to that being analyzed, according to one embodiment.

In various embodiments, pathologists can interpret the xAI output by accessing an interface panel or page by clicking a "Why?" or "Explain" button (FIG. 6). FIG. 9 shows an example display panel 900 displayed by an embodiment of HistoMapr. In some cases, a window or a page may be displayed instead of a panel. The features detected in the ROI 902 are listed along with quantitation of one or more features. In some cases, the features may be associated with a numerical or a qualitative score, such as high, mild, medium, etc. A confidence score analysis of the features (e.g., 0.5, as shown in FIG. 9), which transparently provides HistoMapr's estimate of the strength of its labeling and of the difficulty of the ROI, may also be displayed on the panel 900. The confidence level may be determined based on the presence of explainable features derived from the ROI. A user can forward an ROI to someone else, e.g., an expert, for consultation in ambiguous cases In various embodiments, the confidence score associated with an ROI is based on a composite of individual features' quantitations and/or also on the labeling of the ROI. In some cases, examples of similar ROIs from other cases that can serve as a reference guide, for decision support, may be presented. For example, FIG. 10 depicts a panel 1000 that includes the ROI 608 (FIG. 6), which is labelled ADH. Information about the features is shown, in response to clicking the "Why?" button 604 in the panel 606 (FIG. 6). Upon clicking the "Why?" button 604, an overlay panel 1002 is shown. The overlay panel 1002 includes two reference ROIs 1004, 1006, from one or more other cases, where the reference ROIs are also labelled ADH and have similar features as that shown in the overlay panel 602 for the ROI 608 that is under review. The pathologist can assess the similarity of the different ROIs in determining the correctness of the labeling of the ROI 608. A reviewer may feel more confident about the designated label by visually comparing the ROI 608 that is under review with other ROIs (e.g., ROIs 1004, 1006) that have the same label, where such labeling was accepted.

In some embodiments, a schematic representation of the features in question, with a control (e.g. a slider) that allows the pathologist to view the continuum of that feature from low to high, where the features are ranked based on the importance of the features to a particular condition that is labeled for an ROI. In some embodiments, HistoMapr xAI system presents its differential diagnosis and displays pros and cons of various diagnoses under consideration. If ambiguous, an embodiment of HistoMapr can suggest further work-up with stains, or expedited (e.g., on-line) consultation with another pathologist.

Some embodiments of the xAI system provide a confidence score based (content based) triage of patient biopsies. Cases above a certain difficulty threshold can be distributed to subspecialty expert pathologists, whereas other cases can be sent to front-line general pathologists. The estimate of case difficulty provided by an embodiment of HistoMapr and image volume can be used to distribute pathology cases to a group of pathologists more evenly for better utilization of professional resources. Specifically, as discussed above, embodiments of HistoMapr provide data that supports its diagnostic labelling, and may include a measure of the strength of HistoMapr's decision (e.g., a confidence score), which may indicate whether the decision was straightforward or ambiguous/difficult.

This is a powerful communication from HistoMapr to the pathologist, for it permits the pathologist to understand why HistoMapr labeled the ROI as it did and whether HistoMapr considers the ROI to be difficult or ambiguous. This permits the pathologist to have all of the necessary information for making a diagnosis, and it permits the pathologist to fully examine HistoMapr's performance in real time. At a higher level, this assessment can also be harnessed to drive case triage; difficult appearing cases can be routed to subspecialty expert pathologists for review instead of front-line general pathologists.

Figure 11:
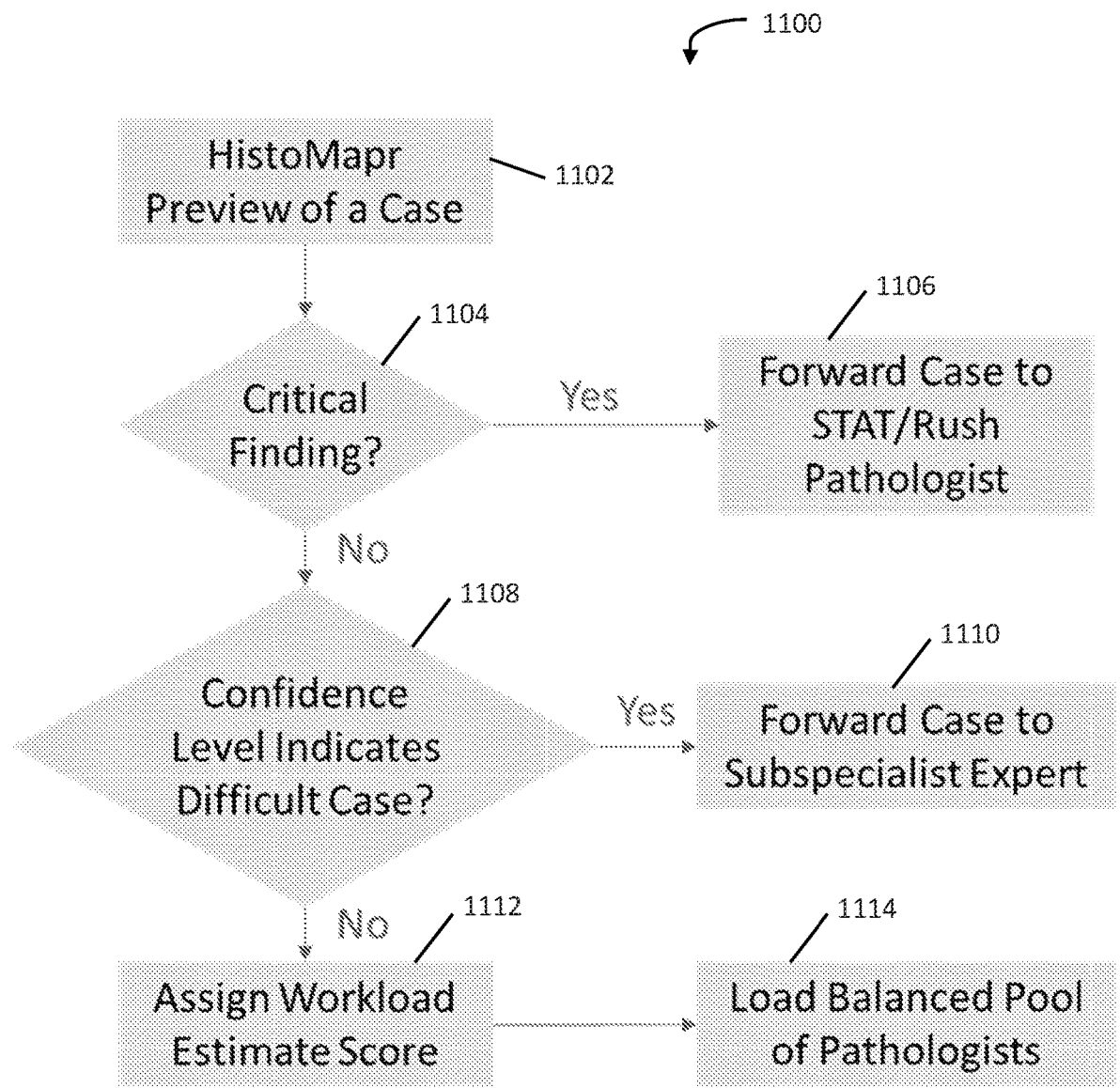
FIG. 11 is a flow chart of triaging performed by an xAI platform, according to some embodiments.

FIG. 11 illustrates an example triaging process 1100. At step 1102, an embodiment of HistoMapr previews and analyzes a case (e.g., one or more WSIs), identifies one or more ROIs, and assigns labels and confidence scores to each ROI. At step 1104, it is determined whether one or more ROIs indicate a critical finding, based on the designated labels. For example, the labeling invasive carcinoma or ductal carcinoma in situ (DCIS) may be considered severe, while a labelling low-risk benign lesion may not be considered severe. If one or more labellings of the ROIs of a case are determined to be critical, the case may be forwarded to a rush pathologist (step 1106).

The labellings of various ROIs of a case are not determined to be severe, the confidence scores of the different ROIs may be considered in step 1108. If the confidence scores or one or more ROIs (up to a threshold number of ROIs) are less than a specified confidence threshold (e.g., 40%, 50%, 75%, etc.), the case may be forwarded to a subspecialist (e.g., carcinoma subspecialist, ADH subspecialist, etc.) that is selected based on the labelling (step 1110). The threshold number of ROIs can be a specified number, e.g., 3, 5, 10, etc., or it can be a percentage, e.g., 10%, 20%, 50%, etc., of the total number of ROIs associated with the case. In some cases, the confidence scores of different ROIs may be aggregated to derive a confidence level for the case/WSI, such as by selecting the maximum of the confidence scores of the different ROIs, a simple average or a weighted average based on the sizes of the ROIs and/or severities of the labels designated to the ROIs, etc.

If it is determined in step 1108 that the confidence scores of the ROIs or the confidence level for the WSI are/is acceptable, a workload estimate score may be computed in step 1112, based on the number of WSIs analyzed and/or the total number of ROIs detected. Using the workload estimate score, the cases may be distributed evenly to a pool of pathologists in step 1114. Thus, in some embodiments, HistoMapr can triage patient biopsies based on confidence level and critical findings in the case. Cases above a certain difficulty threshold can be distributed to subspecialty expert pathologist, whereas other cases can be sent to front-line general pathologists.

Using standardized terminology for diagnosis labels, embodiments HistoMapr can encourage pathologists to report results in a more uniform fashion, thereby improving the quality of the reports. As the pathologist and HistoMapr work through the case together, HistoMapr may use the pathologist's decisions to construct the pathology report in real-time, using standardized language. This can standardize the pathology practice and can improve the quality of a practice's reports by making them easier to understand due to standardization. An example of such a standardized report is shown in FIGS. 1A-1C.

In general, a case (e.g., a WSI) or its individual ROIs, via xAI, are annotated by an embodiment of HistoMapr. In addition to the diagnostic labels there are the features, feature quantitation (numerical and/or qualitative), and confidence scores. These form a fingerprint that can be used to match ROIs with other cases, with libraries of known diagnoses, or with other pathologists' cases for many purposes (FIG. 1). Some of the uses of the annotated WSI/ROIs include: (1) Decision support—Examples of similar ROIs from other cases, from libraries of known diagnoses, or from didactic materials may be shown to a pathologist, to assist in making a decision about an analyzed ROI. (2) Education—comparison of an ROI with known good examples of a diagnosis, and comparison of an ROI to almost-similar ROIs that have different diagnoses (i.e. presenting the differential diagnosis). (3) Quality assurance (QA) activities—partial automation of second review of pathologists' work by other pathologists (e.g. QA reviews, standard second-opinion situations, etc.). Also, ongoing monitoring of HistoMapr performance as part of a pathology practice's QA framework. (4) Clinical Trials—computer-assisted screening of patient suitability for potential clinical trials, streamlining central review of pathology materials (i.e. ROI presentation without need to review an entire case). (5) Content-based image searching for the above purposes or for other reasons.

Importance and Evaluation of HistoMapr xAI System

Figure 12:
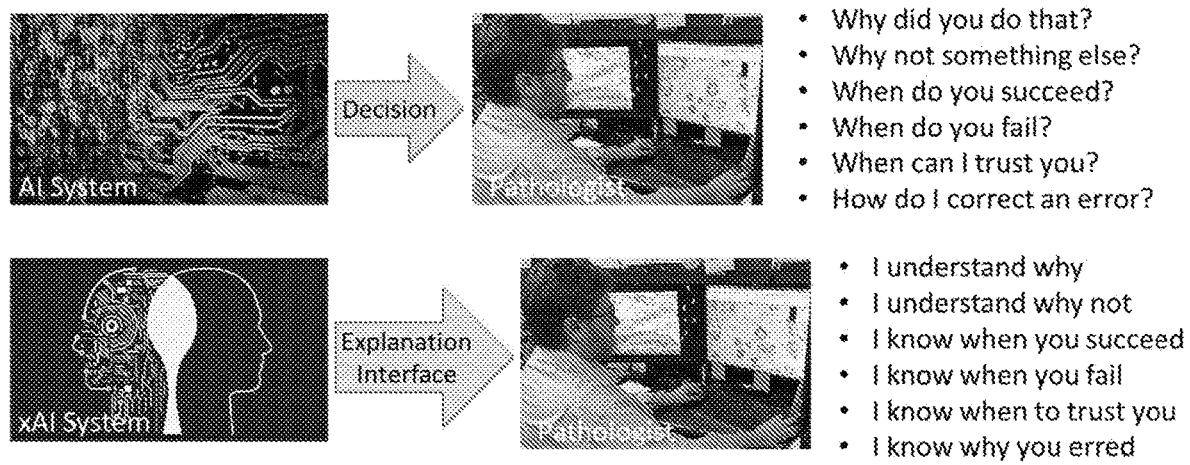
FIG. 12 compares pathological analysis performed according to the conventional techniques with the analysis performed via various embodiments of an xAI platform.

Embodiments of HistoMapr can assist pathologists in a transparent fashion using xAI and can guide them to make the best diagnoses they can. This is a unique aspect of HistoMapr because currently the AI techniques that are known to be used in pathology are based on Deep Learning. It is not currently possible to ask a Deep Learning system, "why?" and to obtain an insight into the analysis performed by the AI. Explainable AI, however, is an important feature for early computational pathology systems, because it can help pioneer pathologists to begin building trust even with a highly-validated intelligent software guides, as shown schematically in FIG. 12.

Another important aspect of using xAI technology comes from possible future regulations on use of AI in decision-making procedures that may affect human rights and/or health. A proposed regulation before the European Union prohibits "automatic processing" unless user's rights are safeguarded. Users now have a "right to an explanation" concerning algorithm/machine-created decisions that are based on personal information. Future laws may further restrict AI use in professional practices, which can represent a significant challenge to industry. Moreover, business and clinical owners may not aim for full automation of machine learning models because they may not blindly trust a model, because there is no quantifiable confidence in how a conventional machine learning model works and transparency in the decision making of a conventional AI is generally inadequate. The regulatory constraints that healthcare must operate within, provide an opportunity for explainable AI, and the HistoMapr xAI system can introduce a level of trust in pathologists with the explanation interface.

In the design of HistoMapr xAI system, key concepts of measurement for the evaluation of xAI systems and human-machine performance are considered. These key concepts include explanation goodness, explanation satisfaction, curiosity metric, and user performance. Briefly, explanation goodness stands for clarity and precision of the explanation provided by the xAI system. The evaluation for this criterion can be made by simply asking yes/no questions to the user to learn: a) if the explanation helps them to understand how the software works, b) if the explanation is satisfying, sufficiently detailed and complete, c) if the explanation is actionable (i.e. helps user know how to use the tool), d) if the explanation lets the user know how accurate and reliable the software is, and e) if the explanation lets the user know how trustworthy the software is. In various embodiments, HistoMapr provides detailed feature explanations in the explanation interface (e.g., confidence level, effect of features on the decision, detailed explanation of features, lets user to act on the output), and, as such, the explanation goodness metric for HistoMapr is likely high.

Explanation satisfaction is to tell the degree to which users feel that they understand the AI system, or the process explained to them. This criterion is common for many xAI systems as it aims to serve the user's goals in understanding the AI process. In order to satisfy this criterion, the xAI system should be able to address users' questions such as, a) how do I avoid the failure modes? (shows user's desire to mitigate errors), b) what do I do if it gets it wrong? (shows user's desire to avoid mistakes), c) what does it achieve? (shows user's interest in understanding the system's functions), d) what did it just do? (user's feeling of satisfaction at having achieved an understanding of how the system made a particular decision), and e) why didn't it do "z" instead of "x"? (shows user's resolution of curiosity at having achieved an understanding of the decision). HistoMapr xAI system can address explanation satisfaction criterion by answering users' questions through its explanation interface. "Why?" button in the HistoMapr GUI is specifically designed to address these by providing explanation to why HistoMapr thinks an ROI is belonging to a specific type of lesion.

Curiosity metric is also an important criterion as explanations can suppress curiosity and reinforce flawed manual processes. This can happen in a number of ways: a) an explanation might overwhelm people with details, b) the xAI system might not allow questions or might make it difficult for the user to pose questions, c) explanations might make people feel reticent because of their lack of knowledge, and d) explanations may include too many open variables and loose ends, and curiosity decreases when confusion and complexity increase. For these reasons, the assessment of users' feelings of curiosity might be informative in the evaluation of xAI systems. HistoMapr xAI system is designed to receive feedback from the end users by asking simple survey questions. Using the user feedback, the information panel can be customized to achieve a high curiosity metric.

Finally, user performance, including measures of joint user-system performance, will improve as a result of being given satisfying explanations. A main aspect of user performance measurement is the quality of the performance of the user, such as the correctness of the user's predictions of what the AI will do. For these aspects of performance, just like performance of the HistoMapr, we measure response speed and correctness (hits, errors, misses, false alarms), but in this case the user's predictions of the machine outputs are measured. Examination can be made for both typical and atypical cases/situations. Additionally, HistoMapr can measure the correctness and completeness of the user's explanation of the machine's output for cases that are rare, unusual, or anomalous.

HistoMapr-Breast: Validation Study

The major goals for this study were to: i) validate an embodiment of HistoMapr-Breast (HMB) over a large number of breast biopsy whole slide images (WSIs); ii) collect ground truth annotations on ROIs from expert pathologists, where such annotations may be used for training embodiments of HMB; iii) detect high-risk benign breast lesions with high accuracy and efficiency that are very challenging for pathologists to agree on with high concordance; and iv) demonstrate that embodiments of HMB can increase the efficiency and accuracy of the pathologists' "calls," and can also increase concordance among pathologists.

Towards these goals, we a) collected 4,865 breast biopsy WSIs; b) tested and evaluated the performance of different embodiments of HMB in differentiating a broad spectrum of breast lesions: benign, atypical hyperplasia ("atypia"), ductal carcinoma in-situ (DCIS), and invasive carcinoma; c) demonstrated navigation of WSIs based on diagnostically triaged (benign to malignant) ROIs; and d) tested the concordance between 3 expert pathologists and performance of 2 training pathologists both with and without the aid of HMB.

A total of 2,171 cases, selected by a pathologist, included 3,347 breast core samples. A total of 4,865 glass tissue slides from these 3,347 samples were imaged and de-identified using Aperio ScanScope AT2 at 0.5 microns per pixel resolution (20× magnification). The resulting 4,865 WSIs were processed by an embodiment of HMB to segment about 201,000 ROIs. We chose 4 main diagnostic categories (Invasive carcinoma, DCIS, High-risk tissue, and Low-risk/benign tissue) to map 24 different diagnoses for potential annotations as shown in Table 1 in FIG. 13. While Table 1 shows several subcategories in each main diagnostic category, in our experiment we used only the four main diagnostic categories for ground-truth labelling. In other cases, one or more subcategories from one or more main categories may be used for ground truth labeling.

Ground truth data labeling is necessary for machine learning training but has historically been a bottleneck. Poorly implemented labeling tools can also squander scarce pathologist time. Embodiments of HMB can effectively addresses this with both automated ROI discovery and a pathologist-friendly ground-truth annotation GUI.

Figure 14:
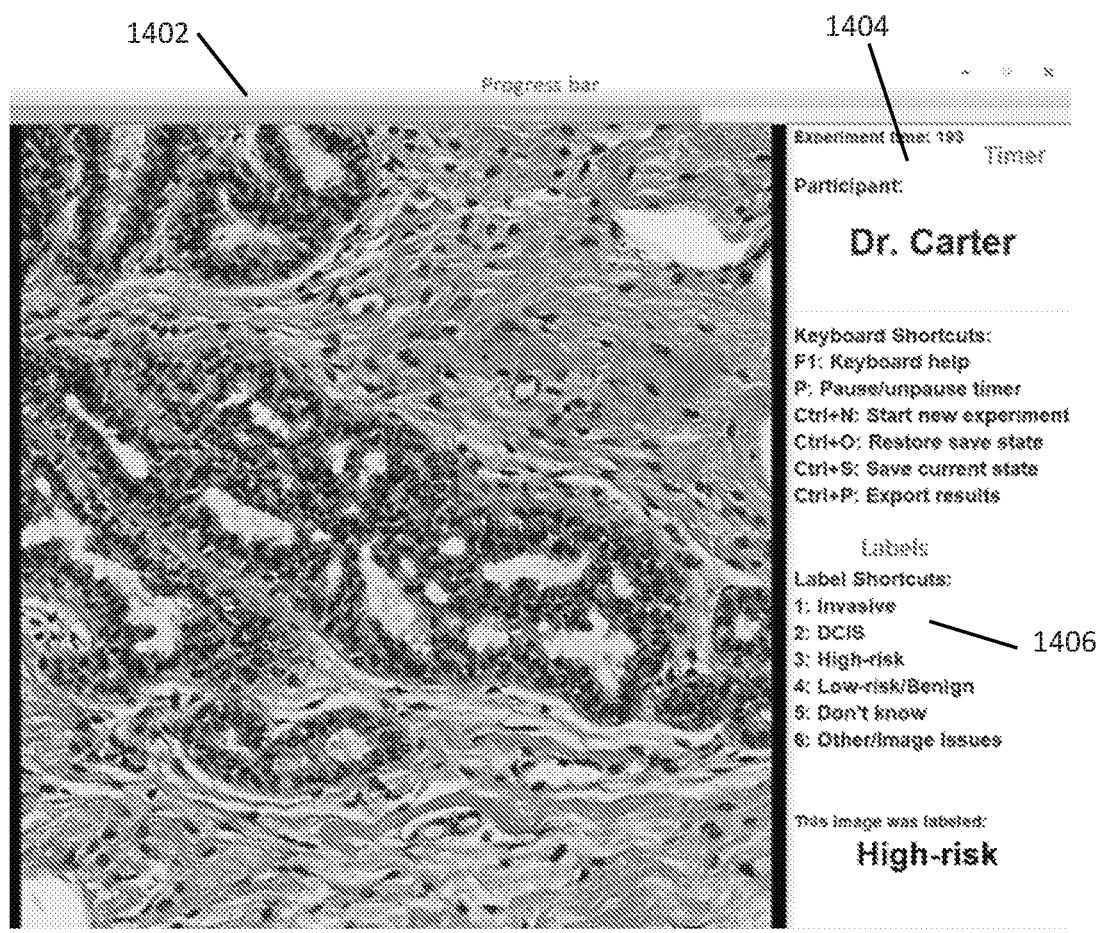
FIG. 14 shows an example GUI that allows a user to diagnose and accordingly label a tissue image, where no suggestion about a condition of the tissue is provided.

Various embodiments of HMB feature an annotation tool having a Java-based GUI, and these embodiments or the annotation tool are easily installable on many operating system platforms. FIG. 14 depicts one embodiment of a rapid annotation GUI, allowing pathologists to go through HistoMapr detected ROIs and to label the ROI using keyboard shortcuts. The field of view in the interface is typically centered around the ROI 1402. The side panel 1404 shows the available categories 1406 and the corresponding keyboard shortcuts.

Unlike many other annotation systems, the GUIs in embodiments of HMB do not require pathologists to hand-draw or print/type their inputs. Instead, in one embodiment, they are shown a series of ROIs one by one and are asked to hit keyboard buttons from 1 to 6, corresponding to labels "Invasive", "DCIS", "High-risk", "Low-risk/Benign", "Don't know", and "Other/Image Issues," respectively. In some embodiments the buttons may be provided on-screen, as part of the display. Fewer or more than six buttons, depending on the number of classes or categories, are contemplated.

In the experiment, first, using the GUI, each of the three pathologist were asked to label 4,462 ROIs. The embodiment of the HMB that was used did not provide any guidance in this phase, i.e., the HMB did not suggest labels for the ROIs. The ROIs for which at least two of the three pathologists agreed on the label (majority vote) were named as consensus labeled set, which included 4,281 ROIs. The pathologists fully agreed on the diagnostic label of 3,172 ROIs, resulting in 71% overall concordance. From the 4,281 consensus labeled ROIs, we selected a test image set of 1,077 ROIs, balanced between the four main diagnostic categories. For concordance analysis, the Fleiss' kappa for this test set was calculated as κ=0.66. We also evaluated the performance of two clinical instructors in pathology ("breast/gynecology fellows") using the 1,077 ROIs. Their accuracy, based on the consensus label from the three experts, across the four major categories was about 67%, as shown in Table 2. In Table 2 "NOT-Using HistoMapr-Breast" means not using the guidance from HMB; the GUI was used.

Figure 15:
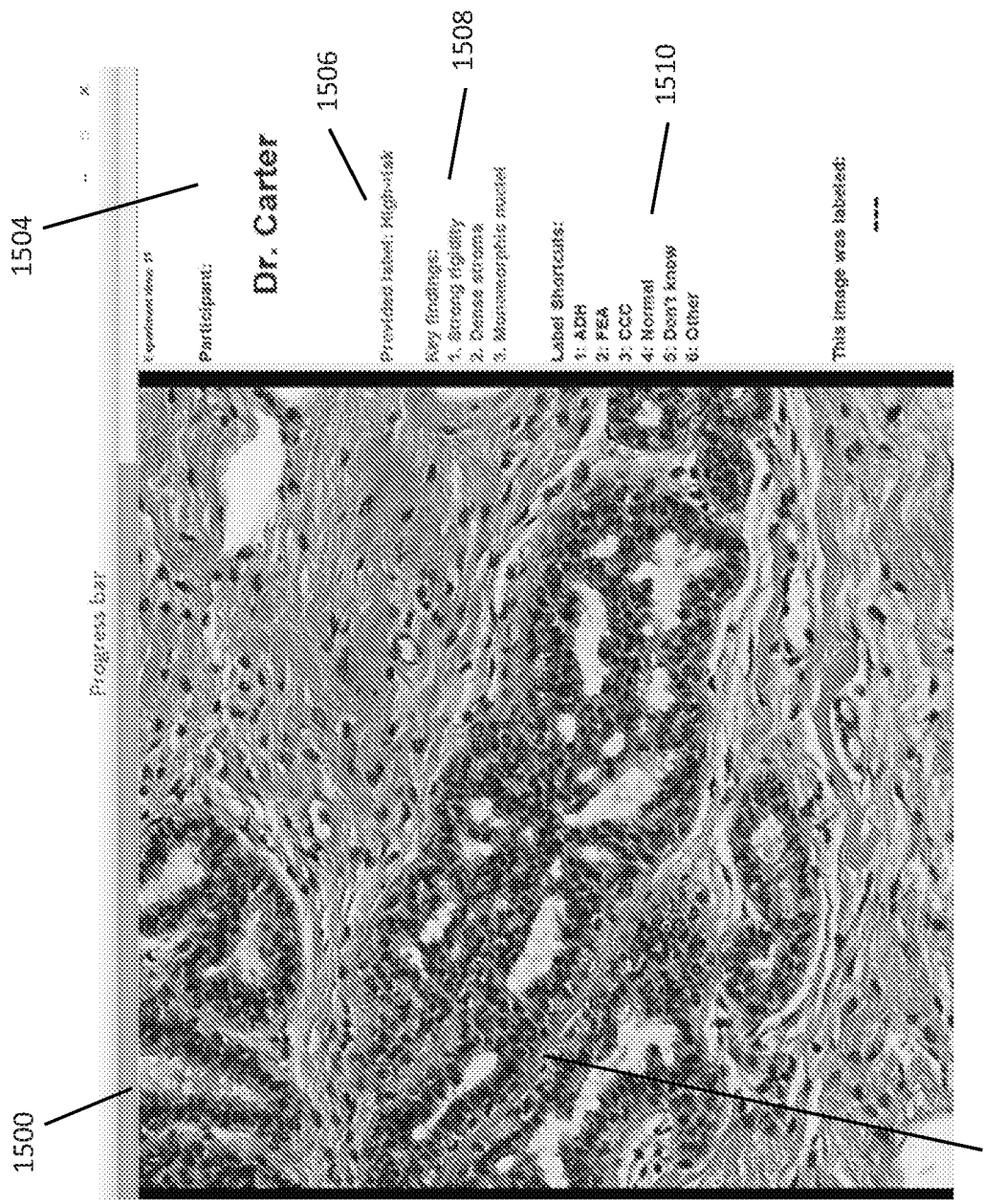
FIG. 15 shows another example GUI that allows a user to diagnose and accordingly label a tissue image, where a suggestion about a condition of the tissue is provided by an xAI platform, according to one embodiment.

Then we re-ran the experiment, but this time the embodiment of the HMB used was configured to provide guidance by designating a respective xAI-generated label to each ROI. FIG. 15 depicts an example GUI 1500. The ROI 1502 is shown, and on the right, in a panel 1504, the HMB's recommendation or suggested label 1506 is shown. The key findings 1508 (i.e., features that explain the labeling) are also shown in the right panel 1504, to assist the user during annotation and/or diagnosis, along with the categories 1510 that are available for labelling. In this phase of the experiment, we tested the effectiveness of the embodiment of HMB by showing ROIs to pathologists with a recommended label from HMB for a given ROI, to determine whether their performance improves.

Specifically, the three expert pathologists were asked to label the 1,077 selected ROIs again, but this time with the guidance of HMB-suggested label, as shown in FIG. 15. Their concordance improved as indicated by an increase in the Fleiss' kappa to κ=0.75. We also re-evaluated the performance of two fellows using the 1,077 ROIs, but with the guidance of HMB-suggested label. Their performance improved significantly, as the accuracy improved from 67% (without guidance) to 91% (with guidance), as shown in Table 2. In Table 2 "Using HistoMapr-Breast" means using the guidance from HMB and the GUI. Thus, the embodiment of HMB that was used demonstrated increased diagnostic accuracy and the performance of fellows. As such, embodiments of the HistoMapr platform can greatly enhance annotation of images for digital pathology.

expert curation, we retained a balanced distribution of breast lesion categories in the image dataset. We trained our AI system with 50% of the annotated data, and used the remainder for validation and testing.

For cytological phenotyping of a ROI, we generated a precise set of nuclei masks for each ductal ROI. Each nucleus was characterized by 196 features that includes morphological, intensity, and texture features. We discovered three dominant phenotypes ($nuclei_1$, $nuclei_2$, $nuclei_3$) as a consequence of normal, atypical, and pleomorphic nuclei in high-risk benign breast lesions. For architectural phenotyping, tissue is represented by 5 different objects: three cytologically phenotyped nuclei ($nuclei_1$, $nuclei_2$, $nuclei_3$) and two superpixel based components (stroma and lumen). A spatial network was constructed by breadth-first traversal from each object. Neighborhood statistics for each object were collected and clustered using k-means into q different architectural patterns, covering 95% of the input variance.

We constructed architectural feature vectors for three different scenarios based on (i) color based architectural features (AF-C) that use superpixel derived nuclei, i.e., stroma and lumen objects; (ii) cytologically phenotyped nuclei based architectural features (AF-N) that use nuclei phenotypes alone; and (iii) combined architectural features (AF-CN) that use nuclei phenotypes in combination with stromal and lumen superpixels. When there is no defined ductal structure, such as in invasive cancer, we expect cytological phenotyping, which captures the frequency and co-occurrence of nuclei phenotypes, to be enough for classification. More sophisticated features, such as our architectural phenotypes, may be considered for a finer subclassification of preinvasive ductal lesions. The runtime performance of the embodiment of the HMB that was used to analyze a WSI was, on an average, less than 2 minutes per WSI on an 8-core 64 GB RAM workstation.

Figure 16:
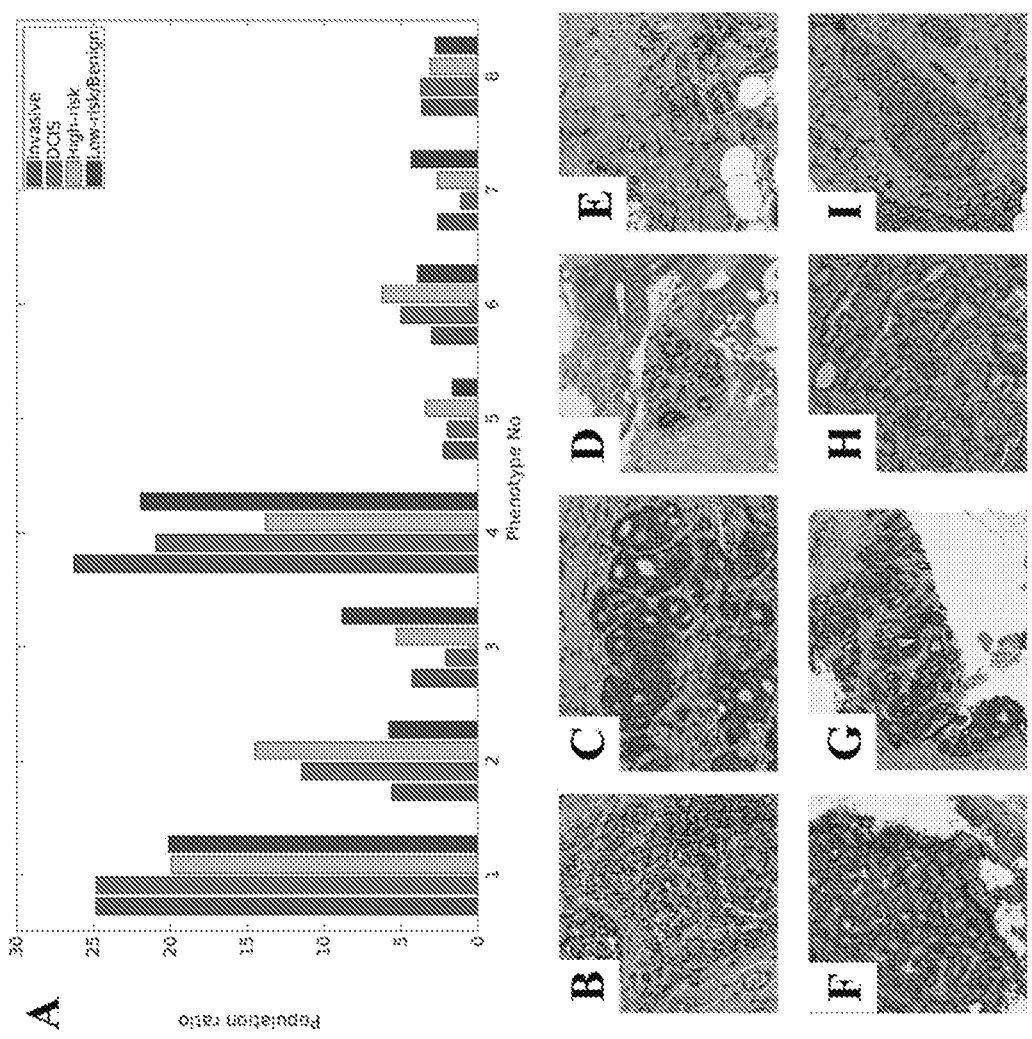
FIG. 16 shows various architectural features of breast tissue that some embodiments of an xAI platform may use in analyzing samples of breast tissue, and examples of different samples of breast tissue having the different architectural features.

We discovered additional discriminative architectural phenotypes to expand our feature vocabulary for xAI. FIGS. 16 depicts these discriminative architectural phenotypes. Panel (A), shows relative proportions of most discriminative architectural phenotypes (8 out of 67 analyzed) in each of the following categories: invasive carcinoma, DCIS, high-risk lesions, and low-risk/benign lesions. Note the following relatively higher populations of architectural phenotypes: #1 in invasive carcinoma and DCIS; #2 in high-risk lesions; and #3 in low-risk/benign lesions. All these phenotypes have

TABLE 2

Performance of Clinical Fellows in Diagnosing 1,077 ROIs

|  | Overall Accuracy (%) | Invasive Sensitivity (%) | DCIS Sensitivity (%) | High-risk Sensitivity (%) | Low-risk Sensitivity (%) |
| --- | --- | --- | --- | --- | --- |
| Mean ± Std dev. NOT-Using HistoMapr-Breast | 66.6 ± 6.8 | 83.6 ± 12.5 | 76.3 ± 2.7 | 26.7 + 22.5 | 72.0 ± 11.3 |
| Mean ± Std dev. Using HistoMapr-Breast | 91.1 ± 3.6 | 96.7 ± 1.3 | 91.4 ± 0.5 | 78.5 ± 13.8 | 95.7 ± 1.5 |

Experiment: Using an Embodiment of HMB to Differentiate a Spectrum of Breast Pathologies Ranging from Benign to Atypia to DCIS to Invasive Carcinoma As described above, the HMB computational pipeline, in general, includes WSI stain color normalization, ductal ROI segmentation, and cytological/architectural feature extraction to further classify ductal ROIs. This process can analyze large WSIs at a rate of about 90 seconds per WSI. With been further reviewed by expert pathologists as they are shown the ROIs that contain the highest proportion of that phenotype. Panels (B)-(I) in FIG. 16 depict ROIs that contain dominant phenotypes #1 through #8, respectively. These phenotypes have histologically meaningful explanations as follows:

Phenotype #1 (panel B) is "nuclear texture smoothness" feature; Phenotype #2 (panel C) is "uniform spacing between nuclei" feature; Phenotype #3 (panel D) is "benign stroma" feature; Phenotype #4 (panel E) is "cellularly populated benign stroma" feature; Phenotype #5 (panel F) is "apocrine & atypical nuclei" feature; Phenotype #6 (panel G) is "Atypical & malignant nuclei" feature; Phenotype #7 (panel H) is "variable inter-nuclei distances" feature; and Phenotype #8 (panel I) is "larger nuclei" feature. These explanations are later used in some embodiments HMB to provide explanation to the user, e.g., in panel 602 shown in FIG. 6.

Following discussions with expert pathologists and practicing clinicians, we designed a stratified classification strategy to suit the purpose of case triaging and retrospective QA where invasive vs non-invasive call is made first, followed by a division of non-invasive diagnosis into preinvasive lesions (atypia and DCIS) or benign and finally applying a classification step of DCIS or atypia. Invasive cancer destroys the normal tissue organization, so it is placed higher on the classification ladder to tailor the feature space on more difficult high-risk atypia.

Because cytological and architectural phenotyping critically depend on precise duct segmentation, we tested embodiments of the HMB pipeline using improved duct segmentation algorithm (described in Appendix A) on the most challenging of all the tasks: low-risk (Normal tissue and columnar cell changes (CCC)/columnar cell hyperplasia (CCH)) vs. high-risk (flat epithelial atypia (FEA) and atypical ductal hyperplasia (ADH)) benign lesions.

Cross-validation experiments were repeated 100 times, splitting into training and testing datasets with a subsampling step ensuring roughly equal training data in all diagnostic categories, before reporting the mean accuracies. We tested different embodiments of the HMB pipeline with naive Bayes, decision tree, random forest, support vector machine (SVM), and logistic regression, and an artificial neural network used as classifiers. The performance of our models using Color Architectural Features (AF-C), Nuclei Architectural Features (AF-N), Combined Architectural Features (AF-CN), and Cytological Features (CF) was observed.

Table 3 summarizes the classification performance results for the three cohort categories: invasive vs. non-invasive; DCIS vs. high-risk & low-risk tissue; and high-risk tissue vs. low-risk tissue. As can be seen in Table 3, decision trees using AF-CN yielded the best performance on the test set of 1,077 ROIs. In some embodiments of HMB, the spatial organization and morphometric properties of nuclei and lumen may be considered, to enhance further the classification performance scores. Although there are several studies on cancer detection in breast tissue images, to the best our knowledge our study using embodiments of HMB is the first of its kind in addressing the most challenging task of classifying high-risk vs. low-risk benign breast lesions from WSIs with high precision.

TABLE 2

Evaluation of an Embodiment of HistoMapr-Breast performance on Three Breast-Core Biopsy Cohorts

|  | Invasive vs. Non-Invasive | DCIS vs. High-Risk & Low-Risk | High-Risk vs. Low-Risk |
| --- | --- | --- | --- |
| F-Score | 0.83 | 0.76 | 0.74 |
| Recall | 0.77 | 0.68 | 0.66 |
| Precision | 0.91 | 0.86 | 0.83 |

Intelligent Case Triaging

As described above, one of the benefits of embodiments HistoMapr xAI platform is the use of xAI features to stratify all the slides (e.g., breast core slides, brain slides, etc.) belonging to a patient. For example, embodiments HistoMapr can analyze all the WSIs of a patient's biopsy by locating and segmenting ROIs. These ROIs may be further ranked based on the classification results according their diagnostics importance. For example, embodiments of HistoMapr-Breast (HMB) can rank the ROIs as: malignant, then DCIS, then atypical and finally benign. Some embodiments of HistoMapr using this information to provide a three-level triaging system that can prepare and triage all the cases within a pathology practice. These three levels of triaging are described below.

ROI triaging: Regions of interest are found, segmented, spatially characterized, and triaged according to their severity and complexity. This can help pathologists in assessing diagnostically critical regions first and can also aid in making the diagnoses. Furthermore, viewing xAI feedback can help the pathologist make critical diagnostic decisions very early in the review process. After reviewing the critical ROIs first, the pathologist may go through the remaining ROIs rapidly, since the decision about the case may have been already formed by the pathologist by looking at the most critical ROIs first. The pathologists can also access the WSI from which the ROIs were identified, where they can visually scan the remaining parts of the tissue (i.e., non-ROI regions) to come to a final diagnosis.

Figure 17:
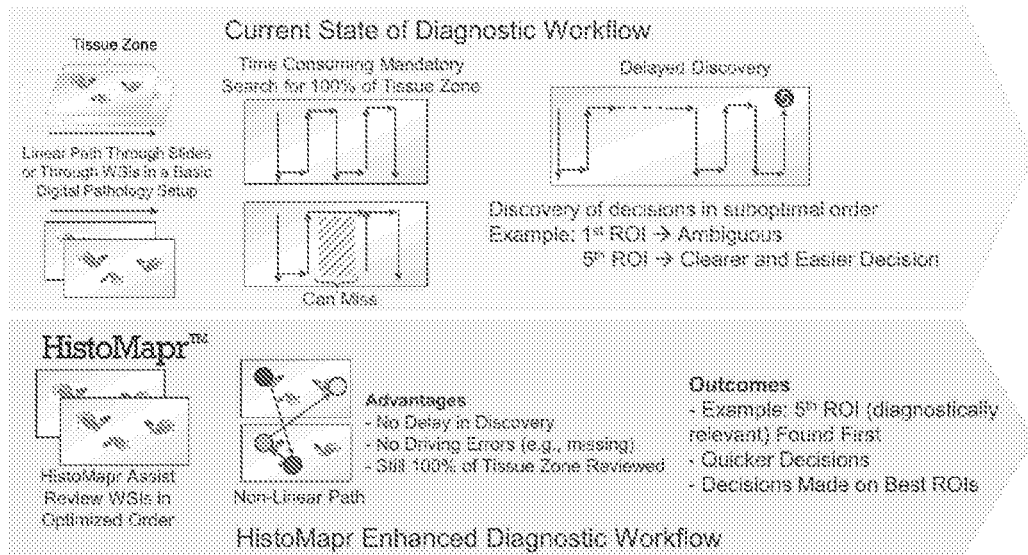
FIG. 17 schematically shows case triaging according to a conventional technique.

FIG. 17 distinguishes between the current review and analysis process that does not use a HistoMapr platform ("non-HistoMapr-process") and an enhanced process using an embodiment of the HistoMapr platform ("HistoMapr-process"). In particular, in the non-HistoMapr-process, the reviewer must go through each WSI sequentially, analyzing a selected region at a time. The reviewer has no prior knowledge whether the region to be viewed is critical to diagnosis. This process is error prone, as some regions may be missed. Moreover, based on the scanning order, critical regions may be examined later than sooner. Furthermore, a difficult to decide, ambiguous region may be viewed/examined before a relatively easy to decide, relatively unambiguous region is viewed/examined. The rigid scanning order generally does not allow the reviewer to benefit from the analysis of easy/unambiguous region in the analysis of the difficult/ambiguous region, unless the reviewer goes back to that region.

Embodiments of HistoMapr-process can avoid many of these problems, because the embodiment of HistoMapr used has first identified and separated regions of the WSI that are important or relevant to analysis from the regions that are not. These relevant, important, critical regions are marked clearly with a suitable border (as shown in FIGS. 2B, 5, 6, for example). Moreover, embodiments of the HistoMapr provide a suggested diagnostic label and, upon request by the user, an explanation of how that region was identified as an ROI, how the suggested label was derived, and an confidence score indicating the platform's confidence in its determination. (See FIGS. 6 and 9, and accompanying discussion). Based on the severity of the suggested label and/or the confidence score, the ROIs deemed most critical are presented to the reviewer first, followed by ROIs deemed less critical. This process can make sure that the entire WSI is reviewed, without missing any regions, the critical diagnosis can be performed early, minimizing delays in the discovery of a critical condition, and diagnostic decisions about relatively easy/unambiguous ROIs can inform the diagnostic decisions about relatively difficult/ambiguous ROIs.

Slide triaging: In this case, the WSIs to be viewed/examined by a pathologist are ordered. To this end, an embodiment of HistoMapr analyzes each WSI, as described above, in a set of WSIs. The WSIs may then be ordered based on the number of ROIs, number of identified conditions, severity of the ROIs (which can be the maximum, average, weighted average, etc., severity across all ROIs in a WSI), confidence scores of the ROIs (which can be the maximum, average, weighted average, etc., confidence scores across all ROIs in a WSI), or a combination of two or more of these factors. The WSIs are triaged, i.e., those deemed more critical (e.g., they may have a large number of ROIs, may have several conditions, may represent severe conditions, and/or the platform may be less confident about its analysis) may be presented to a reviewer for analysis/review before the other WSIs. As such, the reviewer (e.g. a pathologists) do not lose time looking first at WSIs that may not contain diagnostic regions, as can be seen in FIG. 17.

Figure 18:
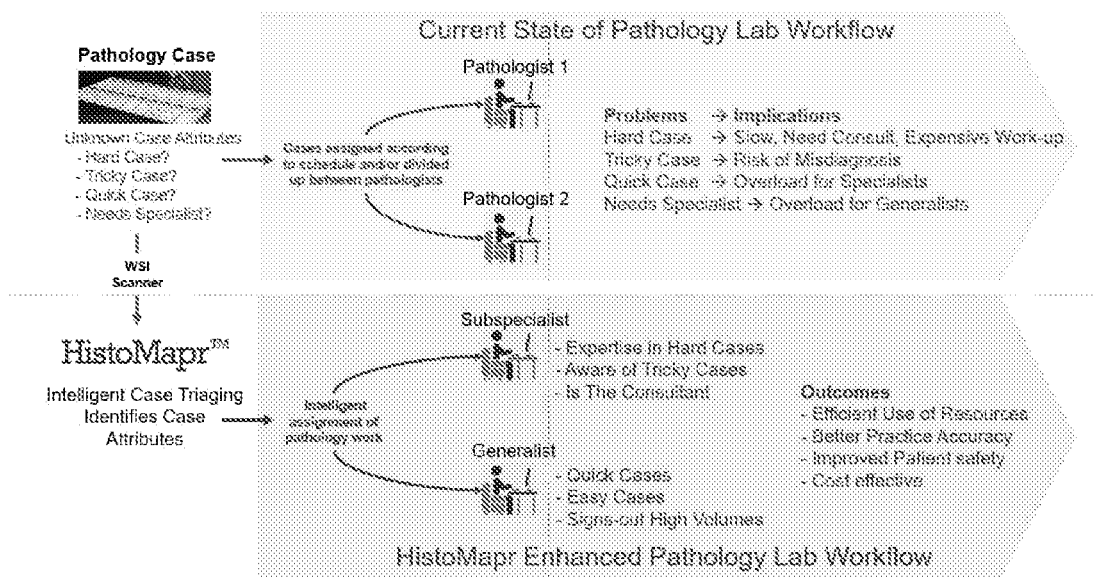
FIG. 18 schematically shows case triaging using an xAI platform, according to one embodiment.

Case triaging: In our discussions with pathologists, we learned that many large practices suffer from unbalanced case distribution due to random forwarding of cases to pathologists. To address this problem, some embodiments of Histo-Mapr can triage cases, and forwarded them to appropriate pathologists according to their subspecialties and/or workload. FIG. 18 shows a comparison of a non-HistoMapr-process and a Histo-Mapr-process. In a non-HistoMapr-process, the case assignment system (or a person) has no prior knowledge about the nature of the case. As such, a hard or a tricky case, if assigned to a generalist or to a specialist who does not specialize in the diagnostic issues pertaining to case, there would be a delay in diagnosis, as the case may need to be forwarded to the right specialist/subspecialist, as shown in FIG. 18. This can also result in overloading the generalists. Moreover, there is a risk of misdiagnosis. On the other hand, if relatively easy cases are forwarded to specialists, that may result in overloading the specialists, and would take their time away from analyzing harder cases. In the Histo-Mapr-process, however, straightforward benign and malignant cases may be forwarded to generalists, while borderline and difficult cases may be forwarded to subspecialists. This can help maintain a case load balance and better usage of the specialists' and subspecialists' time and expertise. An embodiment of a HistoMapr-process is described above with reference to FIG. 11.

In order to apply xAI in a case triaging interface, some embodiments use case subclassification and xAI in terms of "severity of case", "difficulty of case", and "atypical findings" for efficient triage. For example, "severity" may be based on the diagnosis, as cancer is severe, benign is not. In addition, if an embodiment HistoMapr is confident in its decision (e.g., the case has straightforward DCIS or invasive lesions) then a non-specialist pathologist can be assigned to the case, and the case may be designated to be signed-out prior to the benign cases. If the confidence of the embodiment of the HistoMapr is low, the case may be flagged as "difficult" to analyze, and it may be forwarded to a subspecialist (e.g., if the embodiment of HistoMapr is 70% confident that the case is DCIS, then it would be designated go to a subspecialist). Finally, if the embodiment of HistoMapr is confident that the case has "atypical findings" than the case may be assigned to a subspecialist. Embodiments of case triaging can thus improve the throughput of a pathology practice, e.g., by 25% or more. According to our simulations, computational pathology using various embodiments described herein can be up to 56% more efficient than traditional microscopy (e.g., for breast core biopsies).

Figure 19:
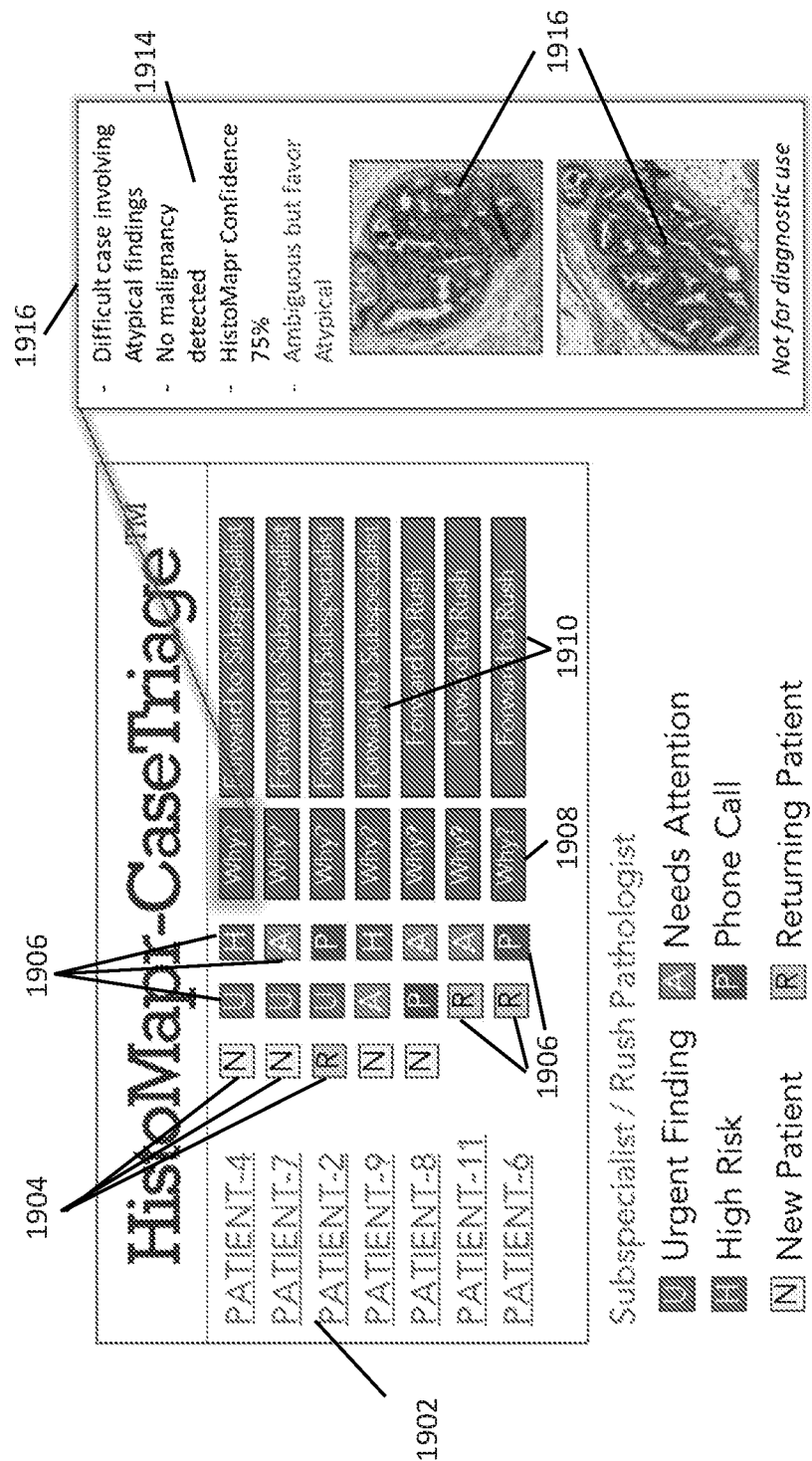
FIG. 19 shows an example of a GUI for case triaging, that embodiments of an xAI platform may provide.

We discussed above, with reference to FIGS. 6 and 9, for example, the valuable explanations various embodiments of the HistoMapr platform provide about the labelling decisions it has made. In a similar manner, some embodiments provide reasons or justifications explaining triaging decisions. Towards this end, some embodiments use an updated terminology, to provide answers in response to a pathologist using a "Why?" or "Explain" option. In particular, in some embodiments, for case triaging, each triaged case is associated with information explaining why the case is triaged in that particular manner. FIG. 19 depicts an embodiment of a GUI 1900 for case triaging. The GUI 1900 includes a list of cases/patients 1902, patient-type indicator 1904 (indicating, e.g., if the patient is new or returning), and indicators 1906 describing the conclusion drawn of the embodiment of the HistoMapr platform used to analyze the case. For each case/patient, the GUI includes a "Why?," "Explain" or a similar button 1908, and an indicator 1910 indicating to whom the case should be forwarded for review. The conclusions that the indicators 1906 indicate may include "Urgent Finding," indicating that the case/patient may have a malignancy or another serious condition, and should be seen prior to other cases. A rush pathologist is typically a non-specialist anatomical pathologist, who is not trained for any specific type of disease/anatomy, but they can diagnose malignancies and benign cases easily and quickly across all organs. Another example of an indicator 1906 is "Needs Attention," indicating that the HistoMapr platform was not highly (e.g., more than 60%, 80%, 90% etc.) certain about its conclusion, "High Risk," indicating that a severe condition was detected with the case, etc.

Upon clicking the "Why?" button 1908, a panel 1912 (or a window or page) is displayed, where the HistoMapr platform would display the information 1914 that is associated with the case and that can explain the particular triaging of the case. One or more relevant ROIs 1916, that can further inform the explanation, may also be displayed in the panel 1912. These explanations/justifications may indicate the difficulty of the case (e.g., "difficult case involving atypical findings", "easy case with definite invasive findings," etc.) and why it is difficult or easy based on the evidence that HistoMapr platform quantified. Some embodiments of the HistoMapr platform also indicate its confidence in the triaging decision using a "Triaging Confidence Score" that incorporates the features, feature quantities, confidence on ROI classifications, etc., within the case.

Figure 20:
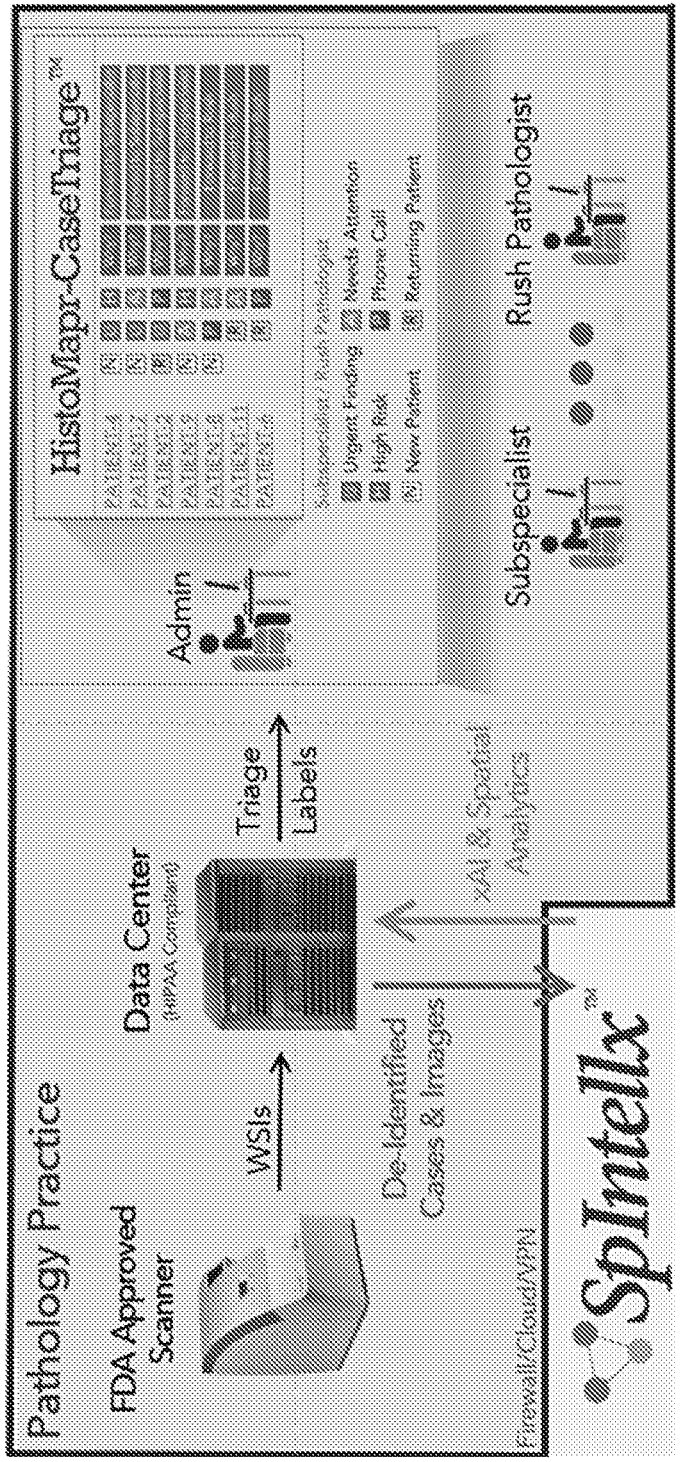
FIG. 20 shows an environment in which embodiments of an xAI platform can perform case triaging.

FIG. 20 schematically depicts a typical operating environment of an embodiment of HistoMapr triaging system. The environment may include the following three modules: (1) a data center interface: an interface that can handle access (e.g., secure, VPN access) to WSI data stored at a remote data center (e.g., at a pathology practice); (2) an embodiment of HistoMapr operated by a third party (e.g., SpIntellx™, as shown in FIG. 20). The data center interface would allow the embodiment of HistoMapr to access and analyze WSI data, and to triage the ROIs, WSI's, and/or cases, as described above; and (3) an embodiment of HistoMapr case triaging tool, installed on a triaging administrator's or a pathologists' computer, that provides a GUI, as described above.

WSIs may be generated, saved, filtered and de-identified at third-party collaborator facilities (e.g., a pathologist lab/office) and would be available for access to the embodiment of the HistoMapr platform via the data center interface. The WSIs may be processed chronologically by running the xAI core algorithms to detect suspected conditions and would then be flagged based on the outcomes and confidence scores of the analysis. The WSIs may be forwarded to the case triaging tool, which can access the results of the analysis of the embodiment of the HistoMapr used to perform the analysis, and the associated explanatory information, from the embodiment of the HistoMapr. The case triaging tool may also access patient data from the pathology practice's information system. The case triaging tool may then automatically (or as used by an administrator) perform triaging and prioritization, as described above. In doing so, case triaging can help distribute cases in a balanced and accurate way, by assigning critical cases to subspecialists or specialists. In some instances, the embodiment of the HistoMapr platform may also be installed at the pathologist's office and the triaging tool may be an integrated component of the platform.

The case triaging GUI (e.g., the GUI 1900 in FIG. 19) can display the list of cases triaged from high priority cases (e.g. malignant, atypical) with pop-up text notifications of new cases with suspected findings when they are ready. In the GUI, each case in the list may have a "Why?" or a similar button. Clicking the "Why?" button of a case in the list pops up a textual explanation of the key findings from the case together with compressed, small, colored, unmarked ROI images that are captioned "not for diagnostic use" and are displayed as a preview of the critical findings, as can be seen in FIG. 19. This compressed preview is meant for informational purposes only, and may or may not contain any annotation/explanation of the findings. Presenting the pathologist with the triaged case list and explanation feedback can facilitates earlier triage by prompting the user to assess the relevant original slides or WSIs. Thus, the suspected cases can receives attention earlier than they would have according to the procedure that does not use case triaging as described herein. Embodiments of the HistoMapr platform do not alter the original medical image. They may provide recommendation for whom to assign the case based on the platform's analysis. The case triaging tool may be used under the control of a supervisor, administrator, or a lead pathologist who will forward the triaged cases to pathologists. Alternatively, the triaging tool may be operated autonomously, and may forward the cases to pathologists by itself.

Retrospective Quality Assurance

One of the most urgent unmet clinical needs for pathology practices are tools and techniques that can reduce diagnosis discordance among pathologists. Many of the studies concerning the diagnostic challenges report only moderate agreement between pathologists. For example, benign breast lesions are an important source of disagreement and uncertainty, resulting in up to 52% discordance on ADH diagnoses. For tough cases like atypia, if the pathologist is not a subspecialist, diagnostic accuracies generally drop significantly. These inaccuracies can lead to unnecessary surgical resections or to missed diagnosis of malignancy, resulting in increased probability of medical malpractice litigation. ADH diagnosis must be reliable, as it confers significant consequences to the patient and can become an economic burden to healthcare delivery systems because of the potential of unnecessary surgeries and the required frequent screening of these patients. Thus, there is a significant unmet clinical need for techniques and tools to allow pathology practices to evaluate how concordant their pathologists are on calls, and to enable them to learn from poor concordance. Although some quality assurance (QA) mechanisms are known, such as randomly selecting 10% of recent retrospective cases for panel review, etc., they are usually neither effective nor efficient QA processes, as many of them are crude and semi quantitative.

To address these challenges, embodiments of a retrospective quality assurance tool RetroQA are provided. RetroQA can be a part of the HistoMapr platform. In various embodiments, RetroQA can review previously finalized cases for ongoing post-diagnostic surveillance. The xAI features of the tool can be used to help identify potential pathology result discrepancies or errors. This important QA activity can reduce risk, improve clinician confidence, and help pathologists monitor their diagnostic work in a timely fashion. As with other HistoMapr xAI applications, a "Why?" button provides the details that identified a QA issue, such as "strong likelihood of malignancy in a biopsy diagnosed as benign", along with supporting evidence, such as an ROI image with highlighted features (such as that shown in FIG. 7), that can support the analysis performed by the tool. In some cases, a confidence score is computed for the finalized diagnosis in a similar manner in which a confidence score is computed for a labelling determined by embodiments of the HistoMapr platform. If the confidence score is low, a message "a very weak confidence score for the diagnosis was rendered" may be provided in response to a user clicking the "Why?" button. Embodiments of RetroQA can improve the post-diagnostic accuracy of the pathologists by up to 25% in many cases, and even more in other cases. According to our studies (see Table 2, above), the sensitivity performance of non-specialists against the ground-truth for the diagnosis of high-risk tissue is moderate (only 27.9%). Using assistance of an embodiment of RetroQA, this performance can be improved.

From our discussions with pathologists, we learned that many practices currently apply quality control to about 10-15% cases that are randomly selected from all the cases analyzed in a certain time period. Cases are either selected retrospectively, post finalization, or during an on-going analysis, prior to finalization, for second review. These cases are reviewed by a pathologist different from the one who first analyzed the case. Since the selection procedure is random, there is still significant risk that misdiagnosed cases are missed, which is especially critical for relatively difficult cases, e.g., those involving atypia in breast lesions. Embodiments of RetroQA can improve the selection procedure, as well.

In various embodiments, RetroQA selects cases that can benefit from a second review. The cases may be selected by using an embodiment of the HistoMapr platform to analyze a WSI associated with a case. The platform may designate a label to the ROIs in the WSI and select a WSI if the assigned label is associated with a severe condition. Alternatively, or in addition, based on the assigned label and/or a confidence score computed by the platform while assigning the label, the platform may determine whether the WSI includes one or more difficult to decide ROIs. In retrospective selection, the platform may compute confidence score(s) for the diagnoses of the ROI(s) in the WSI. Based on any of the factors or scores described above, or their combinations, embodiments of RetroQA may determine that the case/WSI may benefit from a further review and, accordingly, select the case.

Embodiments of RetroQA also feature a "Why?," "Explain," or a similar button, that the pathologist performing the second review may use to understand, e.g., for QA assessment, why that particular case was selected. Upon clicking the "Why?" button, a panel, an overlay, or a page may be displayed in which RetroQA would present the factors and/or scores used in the selection process. Examples of explanatory information or justifications include an indication that the case may be difficult (e.g., a message: "difficult case involving atypical findings, potentially risky for misdiagnosis,"), or other reasons such as: "potential discrepancy, confidence level 85%"). In addition, in some embodiments, RetroQA may also provide the supporting evidence for its selection, such as an ROI image with highlighted features (such as that shown in FIG. 7), that can support the analysis of the tool.

Thus, embodiments of HistoMapr with RetroQA can analyze all previously finalized cases for post-diagnostic surveillance, and may be used to identify cases that will be forwarded for a second review, e.g., for quality control. The cases may be selected because HistoMapr/RetroQA may determine that those cases may have potential discrepancies or errors with respect to the finalized pathology result, and/or their analysis using HistoMapr resulted in a low confidence score, reflecting that the case is difficult to diagnose and potentially carries risk for misdiagnosis. All the cases selected by HistoMapr will be forwarded to consensus of pathologists within the pathology practice for a second review. This can help reduce risk by detecting significant discrepancies (e.g., benign versus malignant), provide evidence to regulators about ongoing and effective QA activities, and improve clinician and patient confidence in diagnoses, especially difficult ones such as breast atypias. The "Why?" button can provide transparency and show why a case was potentially discrepant. This can help improve accuracy of the practice and patient safety.

HistoMapr-Lung: Analysis of Lung Tissue

Tissue staining has been used extensively in pathology for disease or subtype diagnosis, but it has limitations. Computational pathology, i.e. the processing and analysis of medical images with computational methods augmented by high-throughput data collection from the patients can improve disease diagnosis by combining multiple, complementary sources of information. For example, pathologists use Hematoxylin and Eosin (H&E) stained tissue images to diagnose a disease or disease subtype, and H&E image digitization has opened the way to digital pathology. New algorithms were developed to parse image features and assist with the diagnosis or the investigation of molecular mechanisms of disease. These algorithms do not always capture the complex histological heterogeneities, however. Furthermore, tissue images only give a high-level disease pathology. To address these issues, we present a method to parse H&E images to capture explainable heterogeneity features of a tissue, such as breast, lung, and brain tissue. In some experiments, we applied our analysis pipeline to a new dataset that we collected from patients with idiopathic pulmonary fibrosis (IPF) and from control subjects.

Formalin-Fixed Paraffin Embedded (FFPE) lung tissues were collected from University of Pittsburgh and Lung Tissue Research Consortium (LTRC) following Institutional Review Board approved study protocols. Multidisciplinary group of pathologists and clinicians reviewed histopathological, clinical and demographics features of the subjects in the study and confirmed IPF diagnosis. IPF (n=23) and control (n=7) tissues were used in this study as a training cohort, while IPF (n=10) and control (n=10) tissues were used as a validation cohort.

All H&E stained tissues were scanned using Aperio tissue scanner (Leica Biosystems) and submitted for image analysis. Tissue slides in the dataset were scanned at a resolution of 0.5 μm/pixel with a 20× objective resulting in approximately 20,000×30,000 pixels digital whole slide images (WSIs). After the issue-object decomposition step, each image is represented by about 1 million tissue-objects of four different types (lumen, dark stroma, light stroma, and nuclei), as can be seen in FIGS. 21A-F.

Figure 21A:
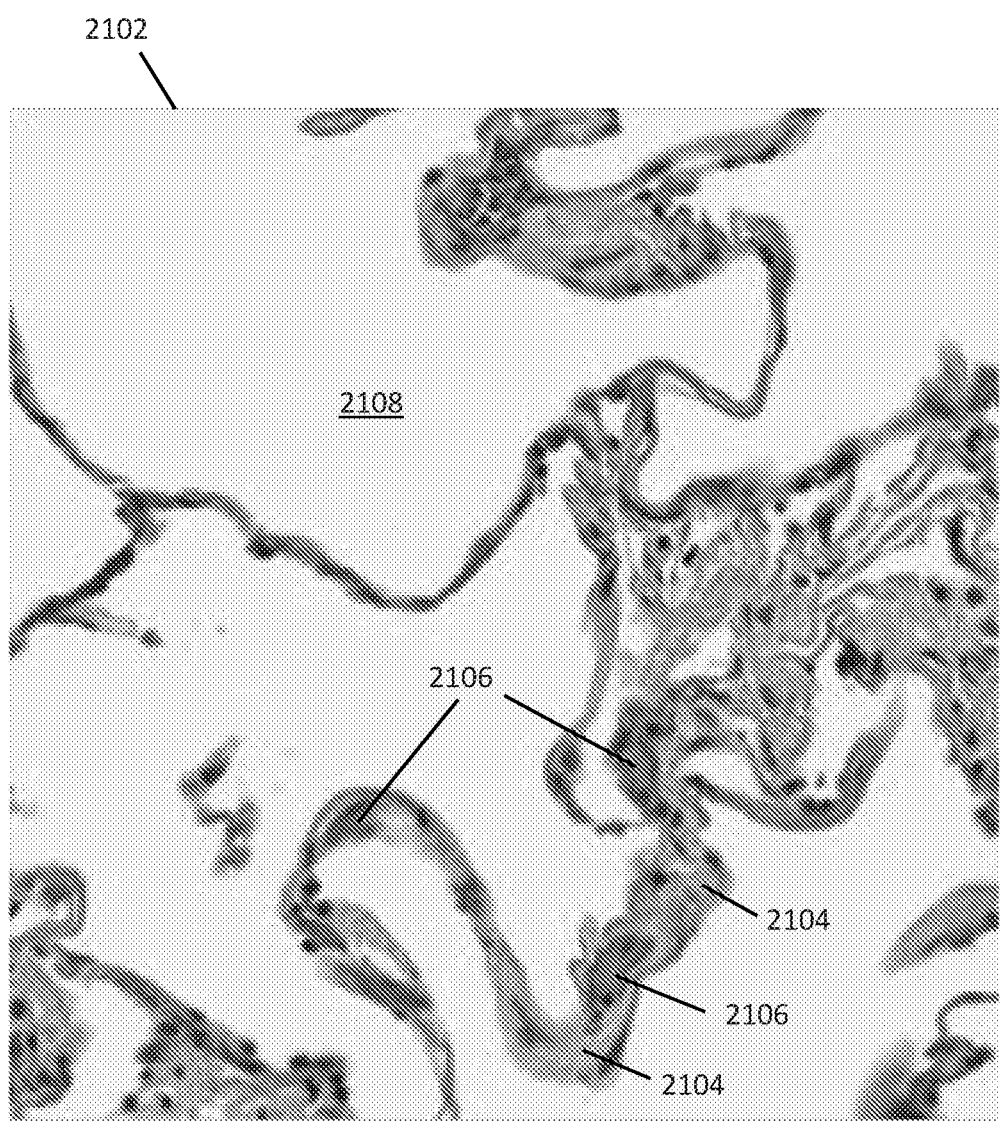
Figure 21B:
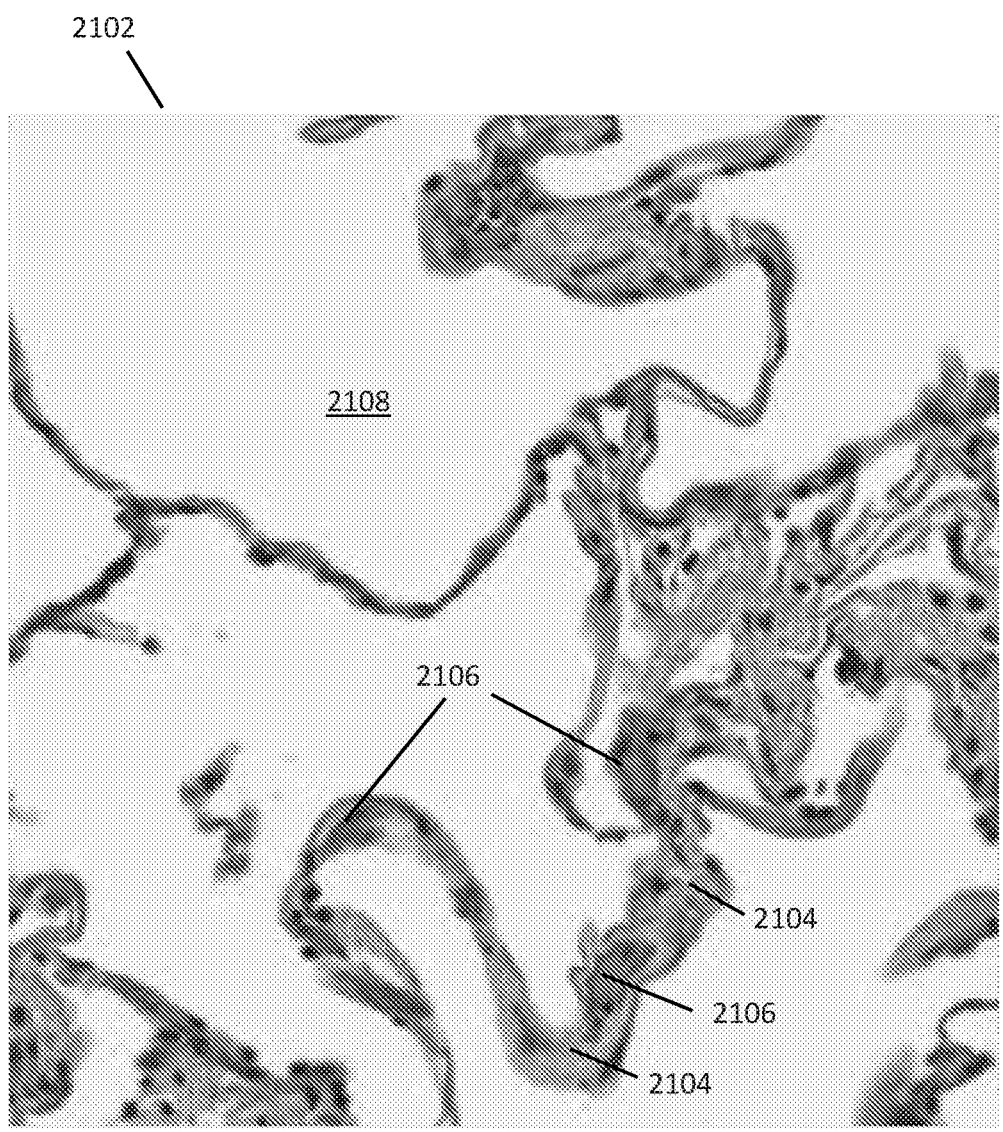
Figure 21C:
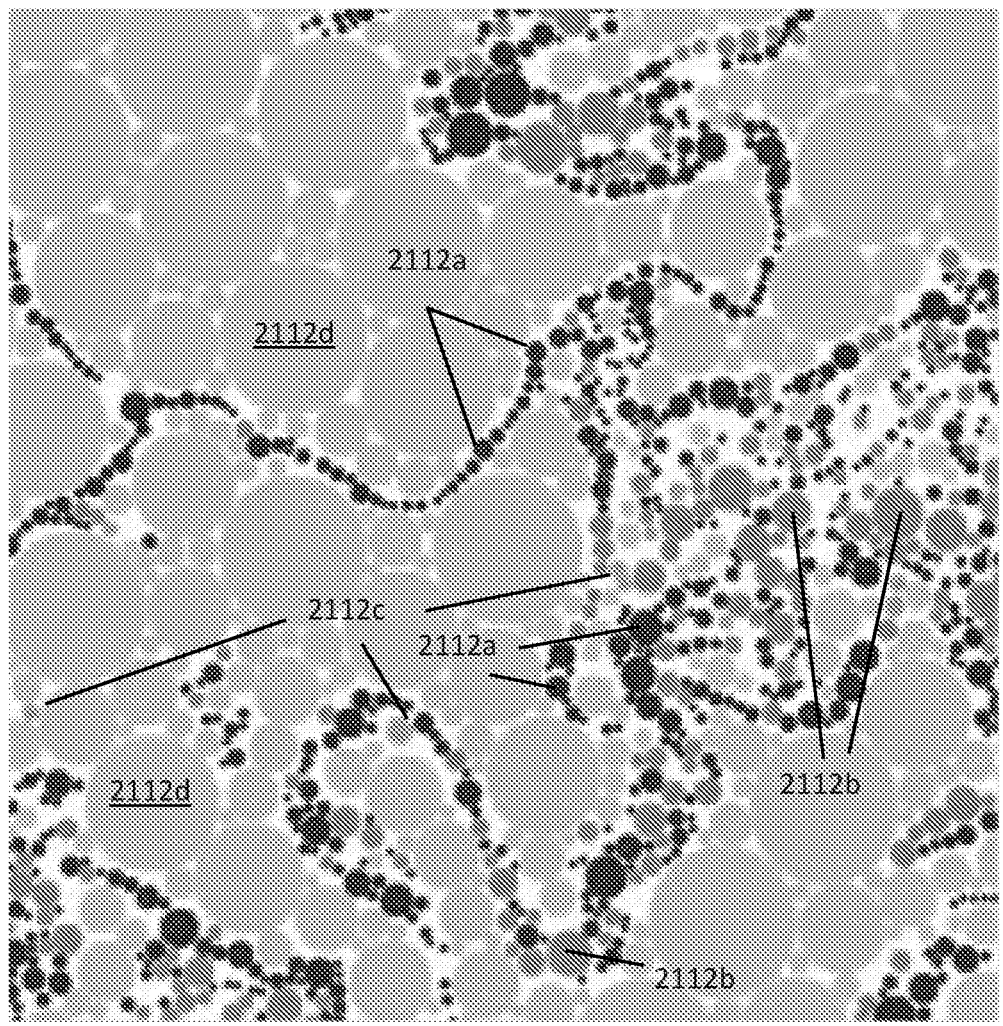
Figure 21D:
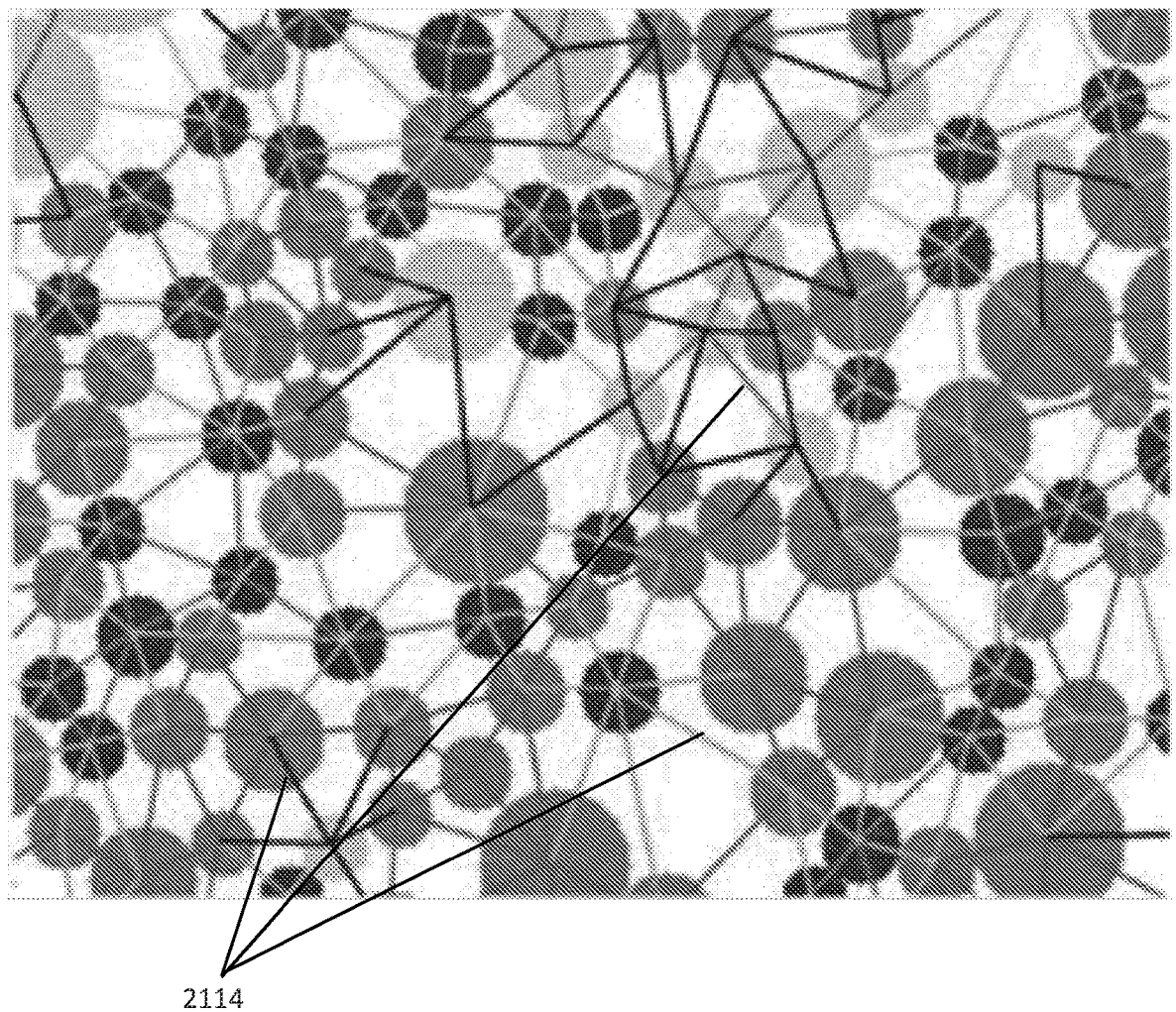

FIGS. 21A-F depict a computational pipeline to model the architectural features (e.g., spatial organization) of histological tissues. In particular, FIGS. 21A-B illustrate color normalization. Histopathology data in the form of whole slide images (WSI) can have a wide range of color appearances due to biological differences, differences in slide preparation techniques, imaging hardware differences, etc. We can reduce this variability by preprocessing the original WSI 2102, a cropped version of which is shown in FIG. 21A, with the cytological components nuclei 2104 (dark purple regions), stroma 2106 (regions with shades of pink), and lumen 2108 (white), to a color normalized version 2110 shown in FIG. 21B. FIGS. 21C-D illustrate object graph generation: The WSI 2102 is then decomposed into circular primitive objects, i.e., tissue-objects 2112, to approximately denote the cytological components of the tissue, as shown in FIG. 21C. A neighborhood graph is built by Delaunay triangulation 2114 on tissue-objects' centers for the entire WSI, where neighboring objects are connected by an edge, as shown in FIG. 21D. FIGS. 21E-F illustrate spatial statistics and feature extraction. We perform random walks on the tissue-object graph 2116 shown in FIG. 21E to encode the spatial neighborhood statistics around each object. A graph such as the graph 2116 is built for each tissue object 2112, as further described below. Then each tissue-object 2112 was represented by a 100-dimensional vector representing the spatial properties of the neighborhood of that tissue object, as shown in FIG. 21F. For example, spatial property #31, corresponding to the vector element #31 denotes nuclei-to-nuclei interaction at four-hop distance for the tissue-object in the center.

Analysis of tissue architecture by pathologist is one of the key aspects in decision making for diagnosis in many diseases and is essential to the diagnosis of IPF. Accordingly, we developed an image processing and analysis pipeline to capture the spatial organization of a different cells within lung tissue. First, we located cell components, such as nuclei and extracellular components such as stroma and alveolar lumen filled with air. Instead of segmenting cytological tissue components, in various embodiments of our technique, we decompose purple, pink, and white pixels of image, corresponding to nuclei, stroma, and lumen respectively, into primitive circular shaped tissue-objects 2112 which then serve as approximate representation of the cytological components of the tissue. In this discussion, reference to "lumen" generally means lumen or white areas of the tissue.

Since decomposition is done on colors of histopathology images that had a wide range of color appearances due to various factors that are noted above, we preprocessed the digital tissue images using a color normalization method. This can be an important step for the robust and correct analysis of histopathological images. For our datasets, we used a known WSI-scalable color normalization method. After color normalization, (FIG. 21B), in some embodiments, we take into account different shades of pink observed in the stroma regions, and we cluster image pixels into four different groups (purple, light-pink, dark-pink, and white) using k-means clustering algorithm, for which cluster centers are computed from principle component analysis (PCA) on color distributions. Next, we fit circular objects 2112 of appropriate sizes into these clustered pixels (with care taken to account for noise) to represent nuclei 2112a, light-stroma 2112b, dark-stroma 2112c, and lumen 2112d objects of the tissue, shown in FIG. 21C. The circular shapes are used for analytical convenience and to serve as a representation for putative nuclei and their neighborhoods. Each image I is represented by a set of tissue-objects $O(I)=[o_i]$, where each $o_i$ is represented by its center coordinates $(x_i, y_i)$, together with its type $t_i \in$[nucleus, light-stroma, dark-stroma, lumen], which serve as a representation for primitive nuclei and their neighborhoods.

To capture spatial architectural features, we construct a neighborhood graph 2116 using Delaunay triangulation 2114 based on the tissue-objects' coordinates $(x_i, y_i)$ (FIGS. 21C-D). Then, we define a breadth-first traversal for each tissue-object $o_i$, by setting $o_i$ as the root 2118 of a tree in the corresponding neighborhood graph 2116, and by visiting the neighboring objects of the root in breadth-first order using the edges of the neighborhood graph (also called Delaunay graph) 2116. We set maximum depth for traversal to be h hops from root tissue-object 2118.

Next, for each depth level we compute the probabilities of finding each type of tissue-object, as shown in FIG. 21E. Since we have four tissue-object types, there are ten different types of edges for each depth level. We selected h=10 as we observed after testing different distances (e.g., h=5, 10, 15, 20, 25) that the random walk converges for h=10. As a result, for a maximum depth of 10 hops, we have a set of 100 probability values describing the spatial properties for each tissue-object. For example, in the graph 2116, the probability of finding another nucleus object from the center object $o_i$ at depth level 1 is 42.9% (=3/7).

In theory, these spatial property vectors capture the distribution of the various cytological components and their interactions in a defined neighborhood. Accordingly, we cluster these vectors, which denote neighborhood properties, into q clusters to find representative architectural features for tissue-object neighborhoods. For that, the principal components of the training data are calculated first and q is selected such that it will cover 95% of the input variance. Following cluster center initialization, each of the tissue-object neighborhoods are assigned to their closest cluster. Finally, for each image, the proportion of q different types of clusters are calculated as the architectural feature vector of the image.

The technique described above, is not limited to lung tissue, and is generally applicable to any type of tissue, such as breast tissue, brain tissue, etc. In some cases, the stroma may not be subdivided into light and dark stroma. Also, instead of only one type of nucleus, as in the analysis of lung tissue described above, there could be different types of nuclei, e.g., three types of nuclei as discussed above in connection with breast tissue. Thus, the number of types of objects in a neighborhood graph and, correspondingly, the number of types of edges in the neighborhood graph can change. Moreover, the depth h at which the random walk of a neighborhood graph would converge can vary from tissue type to tissue type. As the size of the vector representing the neighborhood statistic for each object depends on the number of types of edges in the neighborhood graph and the depth h, the size of the vector and, as a consequence, the number q of the clusters of the vectors that can substantially (e.g., more than 85%, 90%, 95%, etc.) account for input variance, can also change from tissue type to tissue type.

Embodiments of HistoMapr can identify architectural features (AFs) that are consistent with lung pathophysiology. In our experiment, we captured spatial properties from the WSIs without any cropping or tiling, using the image as a whole. To this end, we masked the tissue region to avoid white regions surrounding the tissue and constructed neighborhood graphs, computed spatial properties within tissue regions, and captured architectural features that summarizes the tissue organization as described above. After capturing neighborhood statistics and clustering the decomposed objects based on these spatial statistics into architectural features, we found a total of 12 architectural features that cover 95% of the overall input variance, i.e., q=12 in this experiment. As discussed above, q can change from tissue type to tissue type.

Figure 22B:
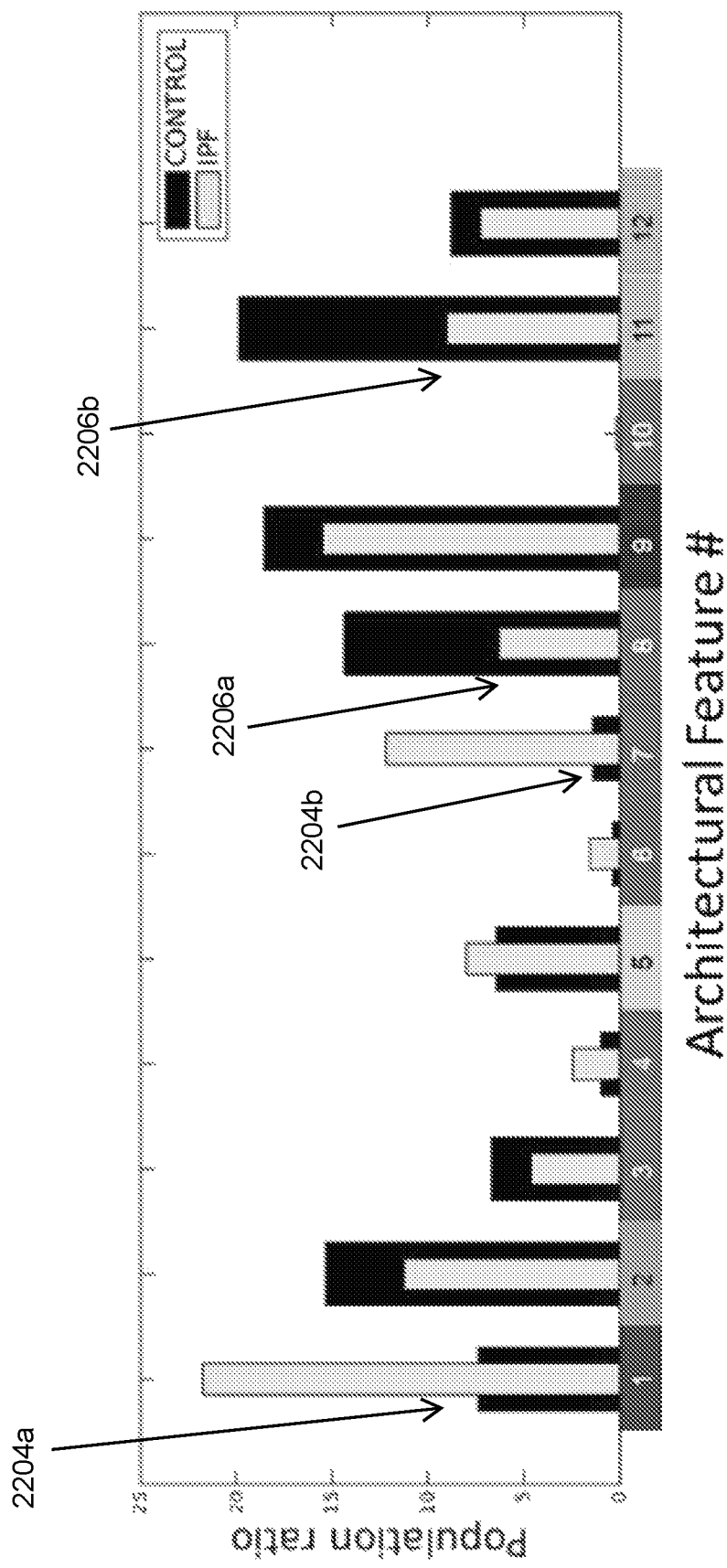
FIG. 22B shows different architectural features of lung tissue.

FIG. 22A shows representative examples of tissue features. The general patterns depicted are consistent with what we would expect from a surgical pathology perspective. Each example comes from IPF or normal samples, depending on which was the predominant category for this particular feature. For the annotation of the AFs below, pathologists examined the surrounding area as well. The 12 AFs are shown schematically, as color coded, in FIG. 22B.

In FIG. 22A, the example in panel 1 corresponds to AF #1 (predominant in IPF) and shows fibroblast foci. The example in panel 2 corresponds to AF #2, paucicellular fibrosis appears to be juxtaposed to normal alveolated lung parenchyma. This could imply various things: subpleural scarring, smoking-related interstitial fibrosis (i.e., scarring in smokers that is often seen in the background lung of cancer resections), an area of IPF, an area of fibrosing lung disease of other etiology (e.g. connective tissue disease, hypersensitivity pneumonitis, etc.), etc. Pertinent feature is the absence of fibroblast foci. This kind of abrupt transition would support a UIP pattern over an NSIP pattern. In a control patient without diffuse fibrosing lung disease, this represents a non-specific scarring.

The image example in panel 3 corresponds to AF #3 and depicts an essentially normal lung. The lung here is collapsed. The red cells 2202 are artifactual (i.e. due to the procedure of procuring this tissue). Our technique can excludes red areas 2202 before image feature extraction. The example in panel 4 corresponds to AF #4 and represents adventitial fibrosis around pulmonary artery branches in a distal bronchovascular bundle. This phenomenon is common and generally increases with age. The connective tissue around the bronchovascular bundle is important to allow for the stretching of the lung around it and for the highly variable vascular loads in different exercise states. Note how there is equally abrupt transition to normal surrounding lung as seen in the example of panel 2 corresponding to AF #2, but this one has medium sized vessels in the center, indicating that this is part of a different structure. The vessels actually are not quite normal. They are small and somewhat haphazardly arranged. The black pigment appears to be carbon dust.

The example of panel 6 corresponds to AF #6 and shows features of cellular and fibrosing interstitial pneumonitis with non-specific interstitial pneumonia (NSIP) pattern. Here the alveolar septa a more or less homogeneously expanded by fibroblasts, inflammatory cells and collagen. There is no accentuation of scarring in the periphery of this pulmonary lobule (which is bordered by the pleura on the upper right), but instead it involved the lobule rather diffusely. The airspace is unremarkable. In the small picture, I think I see some eosinophils, especially in the upper right quadrant. This is a non-specific finding. Tissue eosinophilia can be seen in patients with hypersensitivity pneumonitis, underlying connective tissue or other systemic diseases, drug toxicity (meaning chronic fibrosing interstitial pneumonia due to medication side effect), chronic eosinophilic pneumonia (if this scarred, would be long standing). When we see this features in patients with UIP we raise the possibility that their UIP may be due to connective tissue disease (instead of idiopathic=IPF).

The example in panel 7, which corresponds to AF #7, is characteristic of IPF. This example is architecturally completely remodeled and shows fibrosed lung parenchyma with what appears to be a honeycomb cyst in the lower portion. The ectatic airspace with inspissated mucus is typical for IPF lungs. The amount of chronic inflammation in the surrounding fibrosis is also within the normal spectrum for IPF. The epithelium outside that one large cyst at the bottom often has the eosinophilic appearance of reactive pneumocytes in (various kinds of) pneumonitis.

The example in panel 8 corresponds to AF #8 and shows respiratory bronchiolitis, characterized by airspace pigmented macrophages secondary to cigarette smoking. The alveolar septa are mostly normal, although some show minimal and subtle thickening. What stands out more is the interlobular septum running from top to bottom in the left half of the image. This is a little more fibrosed than usual, and not very cellular. Airspace is normal except for the macrophages. The most common contents are pigment from smoking, pigment from mineral dust exposures and hemosiderin from blood. Blood in airspace happens with bronchiectasis, infections/ARDS, prior biopsies (that kind of hemosiderosis is common in lung allograft biopsies because people get biopsied many times).

The example in panel 11, corresponding to AF #11, depicts a normal lung. Alveolar septa are thin and delicate, capillaries not prominent. There is no alveolar septal edema. The example in panel 12, corresponding to AF #12, similarly depicts a normal lung. Alveolar septa are normal. Airspace contains some pigmented macrophages. The small arteriole at top-left close to the edge of the image looks normal (no onion-skinning or muscular hypertrophy).

FIG. 22A thus illustrates that the architectural features described above can differentiate between normal and fibrotic lung regions. In particular, panels 1-12 of FIG. 22A show that the architectural features derived from neighborhoods of cytological tissue components can help distinguish IPF. These panels show prototypical regions for the various architectural features. For example, panel 1 shows a dominant region of nuclei-to-light stroma interactions that AF #1 represents; panel 11 shows a dominant region of nuclei-to-lumen and lumen-to-lumen interactions; these regions are typically annotated by pathologists as fibroblast focus and normal alveolar region, respectively).

Figure 22D:
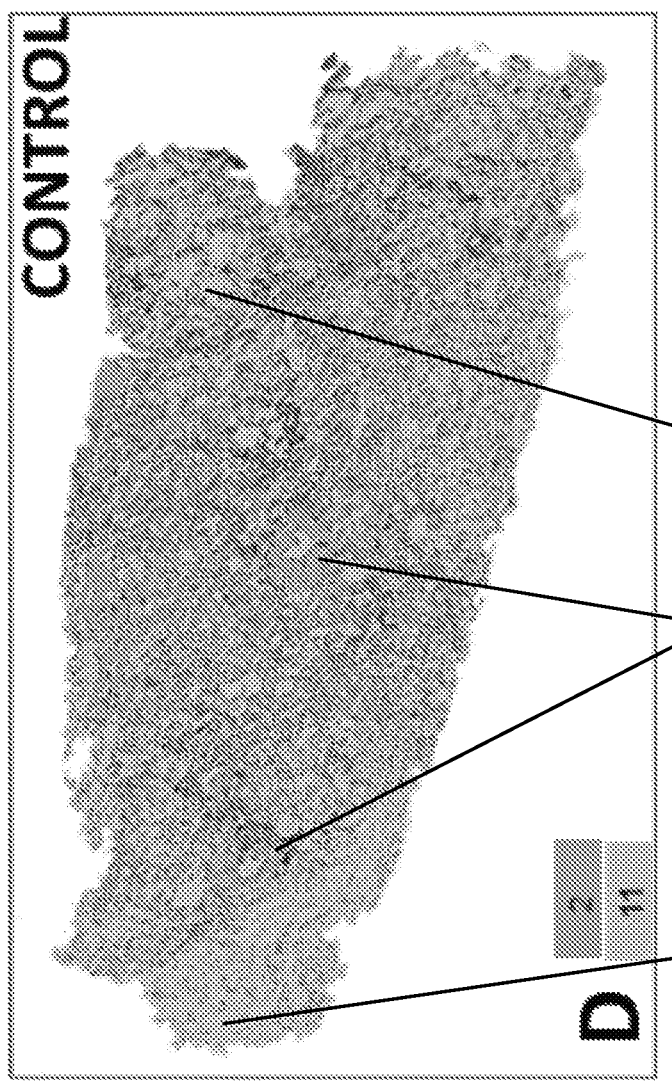
FIG. 22D shows an image of another sample of lung tissue having an over population of certain other types of features, where the tissue image is marked to highlight the features of those other types, according to some embodiments.
Figure 22C:
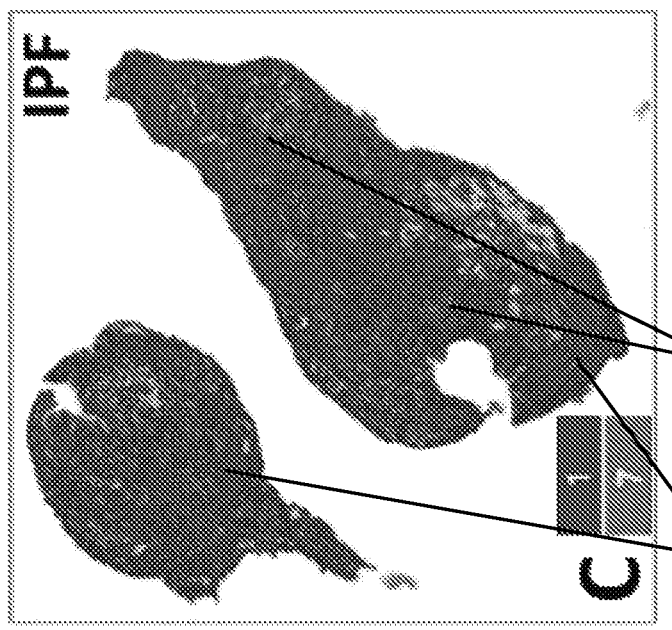
FIG. 22C shows an image of a sample of lung tissue having an over population of certain types of features, where the tissue image is marked to highlight the features of those types, according to some embodiments.

FIG. 22B shows relative populations of architectural features separated for IPF and Control sets. Notice that architectural feature #1 and #7 2204a, 2204b, are dominant in IPF images, while features #8 and #11 2206a, 2206b, are dominant in control images. To visualize some of these patterns in a WSI to be analyzed, an embodiment of HistoMapr highlights them by the colors assigned to each AF. In FIG. 22B, the assigned colors are shown below the x-axis. The objects in a WSI are painted according to the features as shown in FIGS. 22C-D. Specifically, FIG. 22C shows an example WSI from an IPF patient, in which features #1 2212 (blue) and #7 2214 (dark green) are in majority. FIG. 22D shows an example WSI from the control group, where features #2 2216 (light green) and #11 2218 (pink) are dominant.

The percentage of frequencies of these 12 features are shown in FIG. 22B, where the differences between IPF and control types are clearly visible, especially for AF #1, #7, #8, and #11 (i.e., features #1 and #7 are dominant in fibrotic tissue, whereas features #8 and #11 are dominant in normal tissue). Note that these architectural features are connected to tissue structure as they depend on tissue-object interactions. For example, in terms of connectivity in the random walk graph, AF #1 represents a neighborhood where tissue-objects nuclei and light-stroma interact significantly more than other types of interactions and this is followed by interactions in-between light-stroma objects; and AF #11 represents a neighborhood where tissue-objects nuclei and lumen interact significantly more than other types of interactions and this is followed by interactions in-between lumen objects. Having these neighborhood properties represented as architectural features, embodiments of HistoMapr-Lung can summarize each WSI based on how often these features are detected. The difference in features is readily observable between IPF and control samples by comparing FIG. 22C with FIG. 22D.

HistoMapr-Brain: Analysis of Brain Tissue

Some embodiments of HistoMapr, referred to as embodiments of HistoMapr-Brain, can analyze brain tissue. In our experiments, we collected 99 WSIs of brain tissue from Ivy GAP that contain cellular tumor (CT) regions. Here, the WSIs obtained were already H&E stained normalized for color. If unprocessed WSIs are received, however, staining and color normalization would be performed for robust and correct analysis of the WSIs. The tissue slides from which the WSI dataset was generated were scanned at a resolution of 0.5 µm/pixel with a 20× objective resulting in approximately 15,000×18,000 pixels digital WSIs. The received images were also annotated semi-automatically by Ivy GAP to identify certain anatomic features in images. The annotations include leading edge (LE), infiltrating tumor (IT), cellular tumor (CT), and necrosis (NE). For the purpose of our experiments we extracted architecture features of the images, via the process described above, from CT regions of the WSIs. Using the process described above, architectural features can be derived for other regions of the WSIs, as well. Two examples of WSIs with CT regions annotated in green are depicted in FIGS. 23A-D.

Figures 23A, 23B, 23C, 23D:
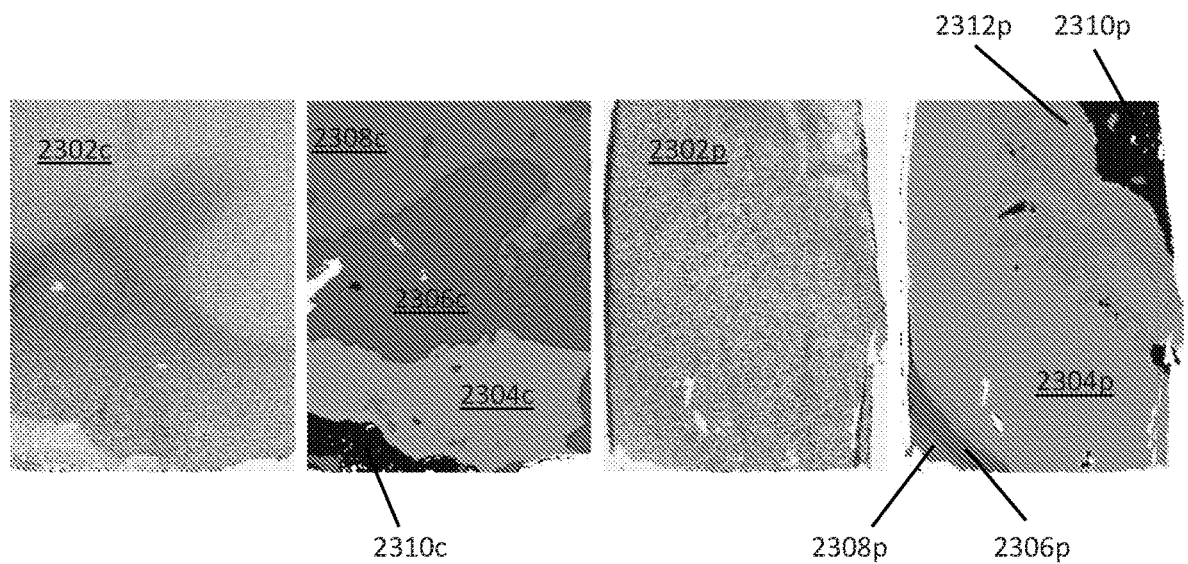
FIGS. 23A-23D shows examples of images of samples of brain tissue.

In particular, representative glioblastoma tissue sections for classical and proneural subtypes 2302c, 2302p, are shown in FIGS. 23A and 23C, respectively. In the references to FIGS. 23A-D, the letter "c" is associated with classical images/regions/features, and letter "p" is associated with preneural images/regions/features. FIGS. 23B and 23D respectively show the annotated regions of each of these images as: cellular tumor (CT) regions 2304c, 2304p (green); infiltrating tumor (IT) regions 2306c, 2306p (magenta); leading edge (LE) regions 2308c, 2308p (blue); necrosis (N) regions 2310c, 2310p (black); and hyperplastic blood vessels in cellular tumor (CThbv) regions 2312p (orange).

An embodiment of HistoMapr-Brain masked decomposed object maps based on the CT regions using the annotations provided by Ivy GAP. We then constructed neighborhood graphs and captured spatial statistics within these masked CT regions, as described above in connection with the overall HistoMapr computational pipeline. After capturing neighborhood statistics and clustering the decomposed objects based on these spatial statistics into architectural features, we found a total of 14 architectural features (i.e., q=14) cover 95% of the overall input variance.

Figure 24A:
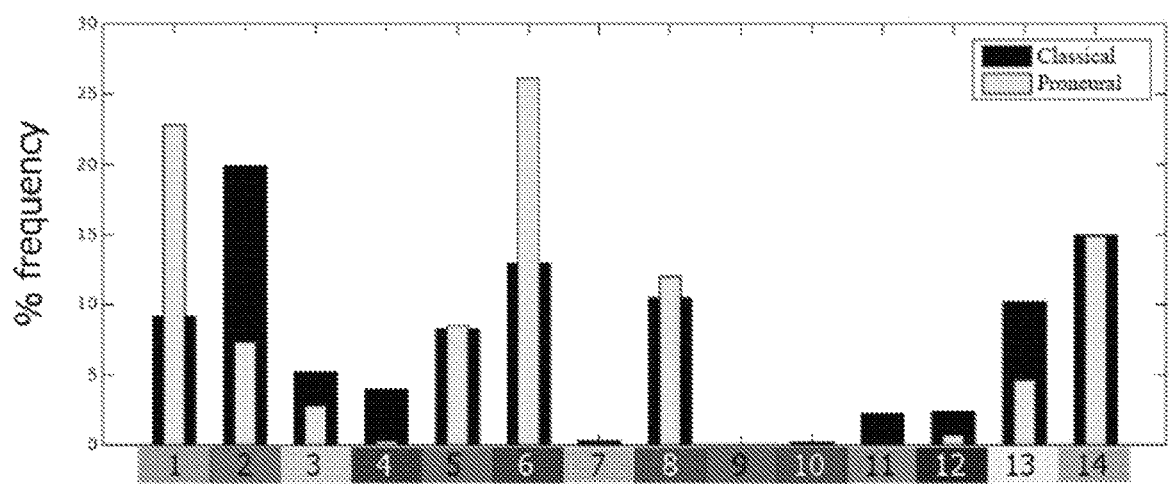
FIG. 24A shows different architectural features of brain tissue.

FIG. 24A shows the percentage of frequencies of these 14 features, where the differences between classical and proneural types are clearly visible, especially for features #1, #2, and #6. Features #1 and #6 are dominant in proneural type of cellular tumor regions, whereas feature #2 is dominant in classical type of cellular tumor regions.

Figure 24B:
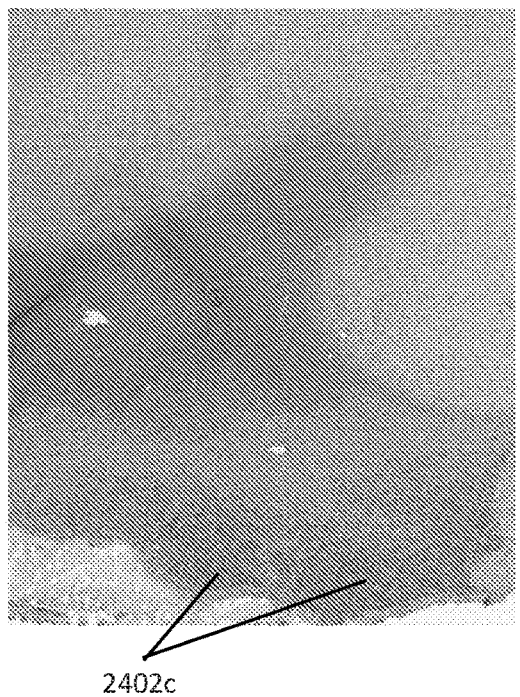
FIG. 24B shows an image of a sample of brain tissue that is shown in FIG. 23A and that has an over population of certain types of features, where the tissue image is marked to highlight the features of those types, according to some embodiments.
Figure 24C:
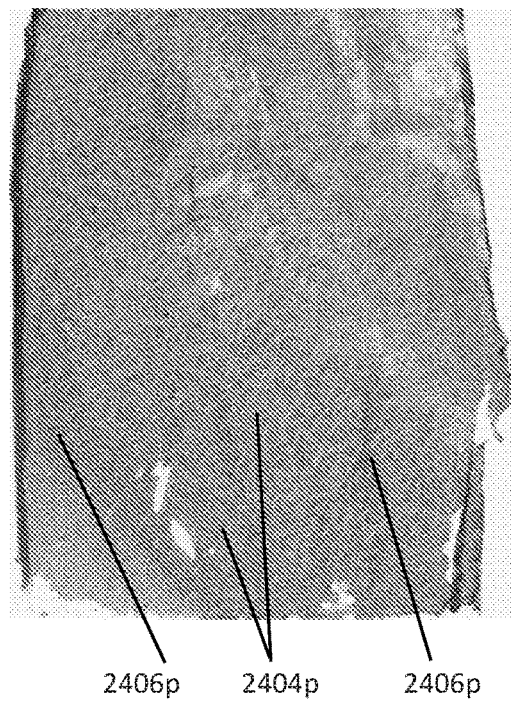
FIG. 24C shows an image of another sample of brain tissue that is shown in FIG. 23C and that has an over population of certain other types of features, where the tissue image is marked to highlight the features of those other types, according to some embodiments.

Specifically, FIG. 24A is a histogram of architectural features, that are numbered 1 to 14, and are color coded. The frequencies for representative classical and proneural glioblastoma sub-types are different for some features. For example, note the relatively higher population of features #1 and #6 in proneural sub-type and of feature #2 in classical sub-type. An embodiment of HistoMapr-Brain then identified in the respective CT regions 2304c, 2304p of the WSIs feature #2 by marking the corresponding objects 2402c red, which is the assigned color of feature #2, as shown in FIG. 24B. Likewise, the embodiment of HistoMapr-Brain also identified in the respective CT regions 2304c, 2304p of the WSIs features #1 and #6, by marking the corresponding objects 2404p, 2406p green and dark blue, respectively, which are the respective assigned colors of features #1 and #6, as shown in FIG. 24C. The difference in the marked features is readily observable between classical and preneural WSI regions by comparing FIG. 24B with FIG. 22C. In the classical WSI, architectural feature 2402 (red) is dominant, and in proneural WSU, architectural features 2404p (green) and 2406p (dark blue) are dominant.

Appendix A

Figures 25A, 25B, 25C:
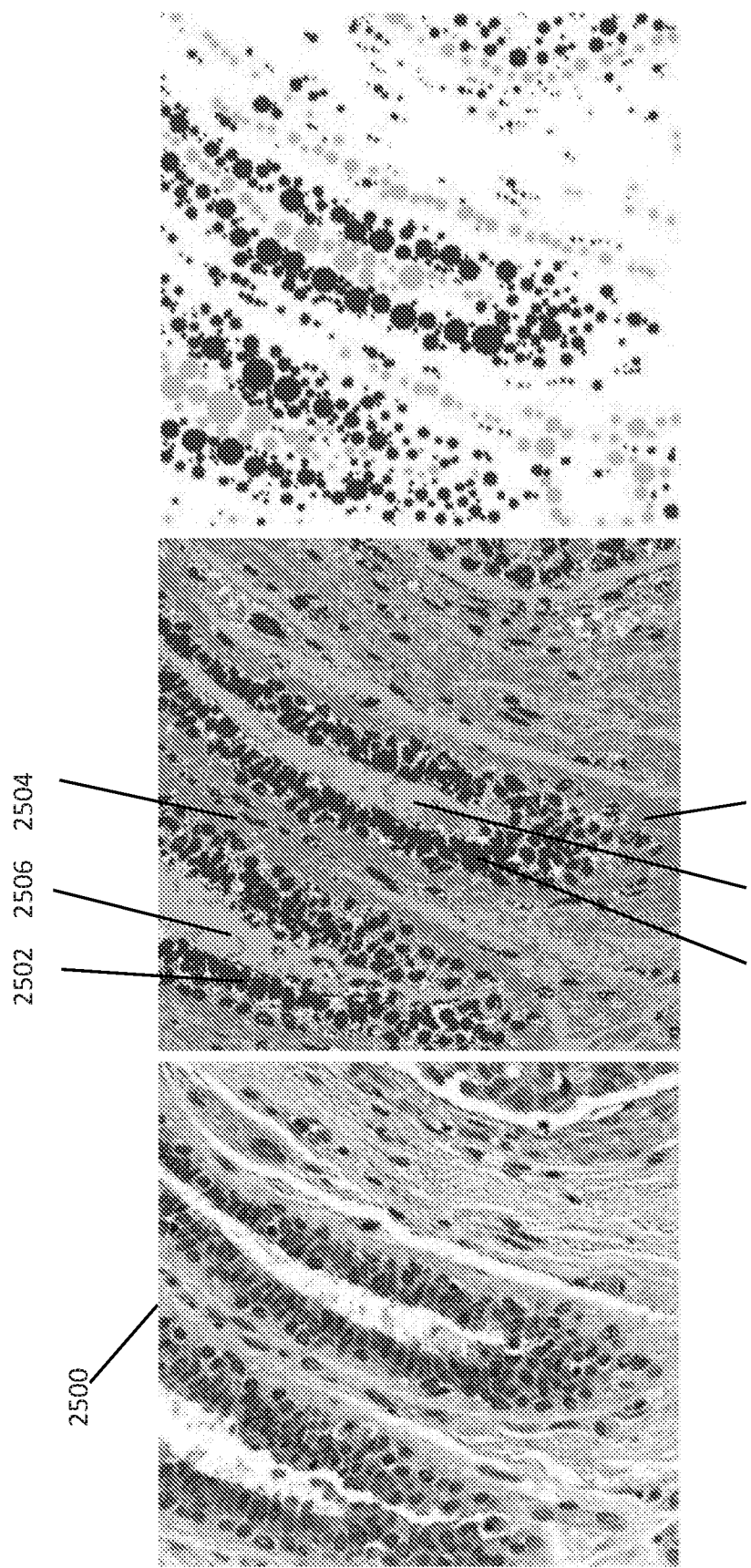
FIGS. 25A-25F show a process of identifying regions of interest, for further analysis thereof, from a whole slide image of a tissue, according to some embodiments.
Figures 25D, 25E, 25F:
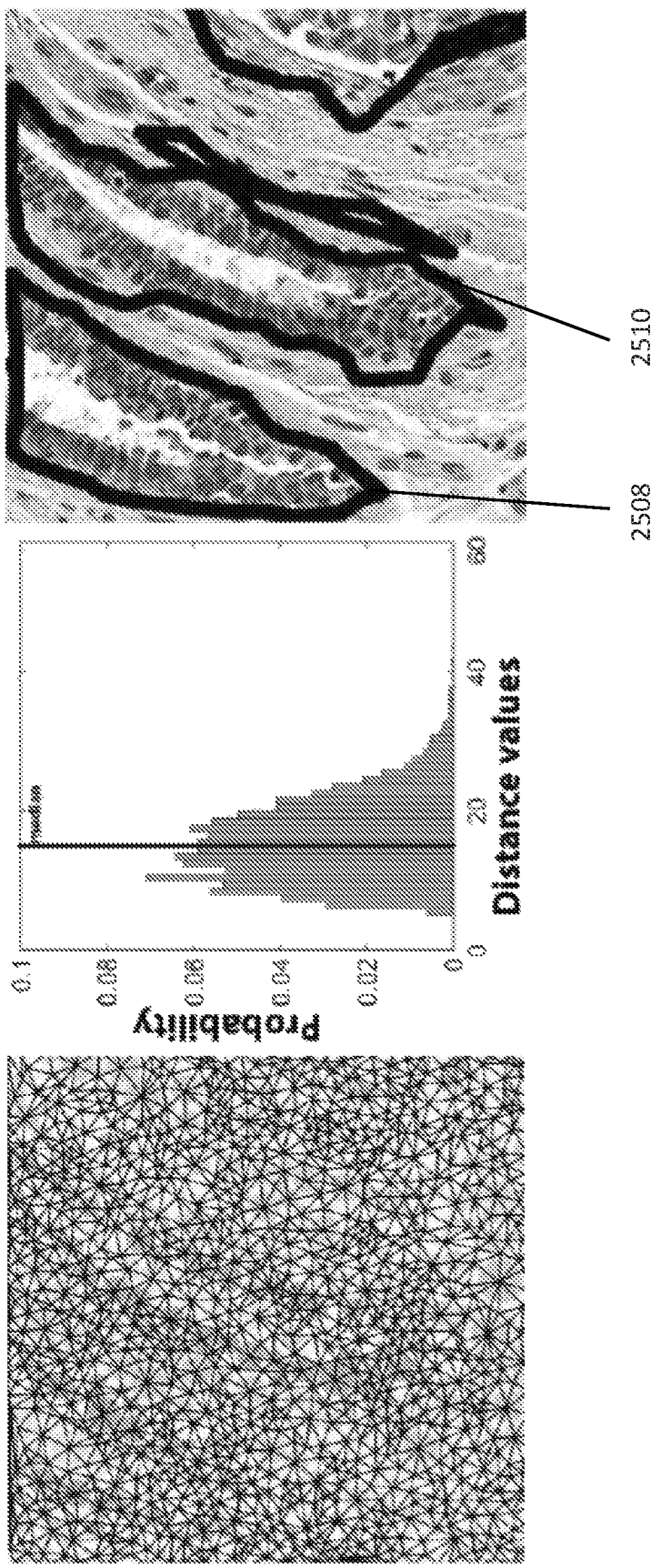

Determination of the Regions of Interest:
We characterize the spatial arrangement of nuclei in a tissue image and use this information to segment regions of interest (ROIs) (see FIGS. 25A-F). The various steps involved in segmenting ROIs include:
1. In a WSI 2500 (FIG. 25A, top-left), we identify putative nuclei locations in the form of superpixels (e.g., circular objects) in the hematoxylin stained tissue regions (H) and characterize neighborhood statistics using superpixels derived from eosin stained (E) and white tissue regions (W). In some embodiments, after color normalization, the H superpixels 2502 are marked purple, the E superpixels 2504 are marked pink, and the W superpixels 2506 are marked cyan. (FIG. 25B, top-right, and FIG. 25C, top-right).
2. To characterize nuclei neighborhoods, we combine superpixels from all three classes, H, E and W, and perform a Delaunay triangulation using their center coordinates (FIG. 25D, bottom-left).
3. We compute pairwise distances between superpixels of the same class. Then, for each class we build a separate graph in which each superpixel as a node, and neighboring superpixels of that class are connected by an edge if their distance is under a specified threshold $\tau$.
4. We set the distance threshold $\tau$ to be at least the median of the distance distribution between neighboring superpixels (FIG. 25E, bottom-middle).
5. We use a greedy connected component analysis algorithm to cluster superpixels into segments.
6. We sort the segments in H and W classes based on their tissue areas in a descending order. We combine segments from these two classes with one simple post-processing rule: if a segment $W_i$ overlaps with a segment $H_j$, regardless of the overlapping area, the overlapping part is absorbed into $H_j$.
7. After merging segments from H and W classes, we have the optimized segmentation of ROIs 2508, 2510 (FIG. 25F, bottom-right).

Ranking of the Regions of Interest:
The ROIs may be ranked based on their cytological and architectural features as described below:
1. To quantify cytological properties, we first segment nuclei by generating a more precise set of nuclei masks in each ROI. Segmentation in this context generally includes applying a threshold on hematoxylin color channel and obtaining putative nuclei regions. Watershed may be used to separate touching and overlapping nuclei and morphological operations may be used to fill any remaining holes. Next, small and large segmented objects and those near the image border may be eliminated. Finally, one round of erosion followed by dilation is performed to smoothen the nuclei shape. Nuclei masks are connected components of pixels denoting each nucleus separately and more precisely. These masks help to locate the shape properties and center coordinates of the nuclei in question.
2. After nuclei segmentation, we compute 196 nuclear features for each nucleus in the ROI.
3. For breast lesions, we found three dominant cytological phenotypes, which we captured using k-means clustering algorithm. The k-means clustering is used to identify the dominant cytological phenotypes. Once they are identified, the xAI would simply use them for a certain kind of analysis. If a different kind of analysis were to be performed, e.g., diagnosis of skin cancer, different cytological phenotypes may be relevant/dominant and need to identified, which can be done using k-means clustering. Thus in general, for different tissue conditions, there may be a different number of and/or different types of dominant cytological phenotypes. The steps may be repeated for the different numbers and/or types of dominant cytological phenotypes.
4. These phenotypes may be a consequence of normal, atypical, and pleomorphic nuclei in high-risk benign breast lesions (FIG. 2C). Amount and type of these cytological phenotypes may differ for different types of tissues.
5. For the task of ROI ranking, we construct a cytological feature (CF) vector for each ROI, which is a summary statistic (e.g., mean, median, std-dev, etc.) of each of the 196 features over all of the nuclei in an ROI under consideration.
6. For quantifying architectural properties, we capture spatial properties of the tissue content.
7. Mainly, the ROI is represented by 5 different objects: three cytologically phenotyped nuclei from previous step ($nuclei_1$, $nuclei_2$, $nuclei_3$) and two superpixel based components from ROI segmentation step (stroma and lumen) as shown in FIG. 2C. Here, nuclei_1, nuclei_2, and nuclei_3 are computational phenotypes, which can be assigned histological meaning by an expert pathologist. In general, lumen superpixels correspond to white space and openings and stroma superpixels correspond to connected tissue. These superpixels do not overlap with nuclei
8. In this dataset pleomorphic phenotype shows up as a distinct subgroup.
9. To characterize the neighborhood around each object, a spatial network is constructed by breadth-first traversal from each object for a small number of depth levels (FIG. 2D).
10. At each depth level we compute the probabilities of finding 15 (this is subject to number of object types defined in previous steps, for 3 types of objects this number would be 6) different object connections (e.g., $nuclei_1$-$nuclei_1$, $nuclei_1$-stroma, $nuclei_1$_lumen, etc.). In some embodiments, an object connection is an edge in Delaunay triangulation that connects two objects as neighbors. As a result, for a maximum depth of 5, we generate a set of 75 probability values describing the neighborhood statistics for each object, i.e., the probability that another nucleus of type nucleus_1, nucleus_2, or nucleus_3 is near/adjacent nucleus-A, or stroma is near/adjacent nucleus-A, or lumen is near/adjacent nucleus-A, where probabilities are separately calculated for each depth level. Each depth level represents the set of neighbors at a given distance, where distance is measured by the number of hops or jumps taken on the graph from center nucleus. With each hop one can go to another depth level as in a breadth-first search fashion).
11. To phenotype the spatial networks, we cluster the neighborhood statistics into q clusters by noting the principal subspace that captures 95% of the input variance. In this, the CF vector defines nuclei phenotypes. Any suitable range for the candidate values of q can be considered. In one study, q was varied from 5 to 38.
12. The architectural phenotypes are learned from applying k-NN (k-nearest neighbors) algorithm, where k=q for each candidate q.
13. Each ROI is then represented by the relative proportion of q architectural patterns. In some embodiments, we perform random walks with architectural patterns as new objects and perform this in a hierarchical fashion with the goal of spatially characterizing the entire whole slide tissue image.
14. We construct architectural feature vectors for three additional sets based on
a. color based architectural features (AF-C) that use superpixel derived nuclei, stroma and lumen objects;
b. cytologically phenotyped nuclei based architectural features (AF-N) that use nuclei phenotypes alone; and
c. combined architectural features (AF-CN) that use nuclei phenotypes in combination with stromal and lumen superpixels.
15. In our pilot study data (46 breast lesion cases with 93 whole slide images), we discovered q=18 patterns/features including architectural and/or cytological patterns/features that represent the ROIs (FIG. 3).
16. We used logistic regression for classification/ranking of ROIs based on feature sets CF, AF-C, AF-N, and AF-CN.

Triaging:

Each ROI is labeled with a diagnosis and a confidence score

ROIs are ordered generally in a descending order based on 1) severity of the diagnostic label and/or 2) confidence score, so that the most confident, most serious labeled ROIs are typically ranked above less confident ones, or less severe ones.

The triaging is done after each ROI has a label or a rank.

Provisional Diagnosis

HistoMapr is not a diagnostic system. It is an assistive system designed to guide pathologists during their daily struggles of signing-out cases.

1. HistoMapr previews cases and then dynamically assigns them to one or more pathologists based on case difficulty (expert subspecialist pathologists versus generalist pathologists) or work-volume (even distribution of pathology cases across pathologists)
2. Pathologists log in to access the cases assigned to them, which appears as a Table with sortable fields consisting of case ID, HistoMapr Status, and additional information about the case (e.g., organ, processing dates, flags about urgency, revisiting patient, etc.)
3. They open a case which will bring the HistoMapr case viewing interface (FIG. 4). The xAI platform may sort the fields/ROI by urgency (e.g., harder or ambiguous cases, straightforward, high-confidence cases, etc.)
4. In the middle of the interface is the whole slide image viewer—the pathologist is always in control of the case
5. Standard and familiar controls for basic user; the breast core biopsy images of the case in review are in the right panel, and there is patient information in the left panel
6. HistoMapr previews all the WSIs and finds the diagnostically relevant ROIs and modifies the boundary pixels to mark the ROIs, at the bottom panel the ROIs collected from all WSIs of the case are triaged from malignant to benign (left to right).
7. For each ROI selected HistoMapr provides a diagnostic label with a key differentiator: explainable A—HistoMapr has a "why?" button that brings diagnostic explanation for each ROI that has a label, explaining why HistoMapr decided on that label and the associated confidence score.
8. HistoMapr provides decision support through its labeling of ROIs, backing up those labels with "why?" information; this reduces uncertainty and improves diagnostic confidence.
9. The pathologist has several workflow options—the agree/disagree boxes are meant to support the pathologist's work. When pathologists want to end HistoMapr review "Finalize" button is used to bring up summary of the assessments.
10. Summary page is to show pathologist a review of ROI that has been viewed and the labels that have been Agreed/Disagreed/Maybe (FIG. 5). The Disagreed/Maybe ROIs can further be reviewed and given new labels using HistoMapr annotation tool described in original document "Innovative Features, item 2".

Providing Explanation in Response to a User Activating the "Why?" Interface

The order of work done to generate reasoning/explanations on the ROI labels is:
1. ROIs are segmented
2. Descriptive spatial features are calculated for each ROI
3. Features are further phenotyped based on their similarities to the principal subspaces describing architectural patterns
4. Prior to the use of an xAI platform for analyzing a new, previously unanalyzed WSI, architectural patterns from other images are examined visually by experts (pathologists) and assigned a histopathologically meaningful description (i.e. rigidity, stromal density, hyperplasticity, etc.).
5. ROIs are classified/labeled based on their relative architectural pattern proportions using logistic regression (the classification can be done using other methods like SVM, Random Forests, etc.).
6. ROIs are ranked based on the severity levels of their classification results (severity of each label is predefined by pathologists in literature). The ranking may also be performed in two steps: Based on the severity levels in Step A and based on the confidence scores in Step B. Either step can be performed before the other step.
7. The distribution of architectural and/or cytological patterns/features within each ROI is quantified and their presence/absence are reported in the explanation interface (i.e., low/medium/high rigidity, etc.). Each pattern feature may have a plus/minus indicator, indicating how that pattern/feature contributed to the ROI diagnosis label. This provides the basis of the confidence score.

It is clear that there are many ways to configure the device and/or system components, interfaces, communication links, and methods described herein. The disclosed methods, devices, and systems can be deployed on convenient processor platforms, including network servers, personal and portable computers, and/or other processing platforms. Other platforms can be contemplated as processing capabilities improve, including personal digital assistants, computerized watches, cellular phones and/or other portable devices. The disclosed methods and systems can be integrated with known network management systems and methods. The disclosed methods and systems can operate as an SNMP agent, and can be configured with the IP address of a remote machine running a conformant management platform. Therefore, the scope of the disclosed methods and systems are not limited by the examples given herein, but can include the full scope of the claims and their legal equivalents.

The methods, devices, and systems described herein are not limited to a particular hardware or software configuration, and may find applicability in many computing or processing environments. The methods, devices, and systems can be implemented in hardware or software, or a combination of hardware and software. The methods, devices, and systems can be implemented in one or more computer programs, where a computer program can be understood to include one or more processor executable instructions. The computer program(s) can execute on one or more programmable processing elements or machines, and can be stored on one or more storage medium readable by the processor (including volatile and non-volatile memory and/or storage elements), one or more input devices, and/or one or more output devices. The processing elements/machines thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processing element as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. Sets and subsets, in general, include one or more members.

As provided herein, the processor(s) and/or processing elements can thus be embedded in one or more devices that can be operated independently or together in a networked environment, where the network can include, for example, a Local Area Network (LAN), wide area network (WAN), and/or can include an intranet and/or the Internet and/or another network. The network(s) can be wired or wireless or a combination thereof and can use one or more communication protocols to facilitate communication between the different processors/processing elements. The processors can be configured for distributed processing and can utilize, in some embodiments, a client-server model as needed. Accordingly, the methods, devices, and systems can utilize multiple processors and/or processor devices, and the processor/processing element instructions can be divided amongst such single or multiple processor/devices/processing elements.

The device(s) or computer systems that integrate with the processor(s)/processing element(s) can include, for example, a personal computer(s), workstation (e.g., Dell, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a processor", or "a processing element," "the processor," and "the processing element" can be understood to include one or more microprocessors that can communicate in a stand-alone and/or a distributed environment(s), and can thus can be configured to communicate via wired or wireless communication with other processors, where such one or more processor can be configured to operate on one or more processor/processing elements-controlled devices that can be similar or different devices. Use of such "microprocessor," "processor," or "processing element" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communication protocols, and unless otherwise specified, can be arranged to include a combination of external and internal memory devices, where such memory can be contiguous and/or partitioned based on the application. For example, the memory can be a flash drive, a computer disc, CD/DVD, distributed memory, etc. References to structures include links, queues, graphs, trees, and such structures are provided for illustration and not limitation. References herein to instructions or executable instructions, in accordance with the above, can be understood to include programmable hardware.

Although the methods and systems have been described relative to specific embodiments thereof, they are not so limited. As such, many modifications and variations may become apparent in light of the above teachings. Many additional changes in the details, materials, and arrangement of parts, herein described and illustrated, can be made by those skilled in the art. Accordingly, it will be understood that the methods, devices, and systems provided herein are not to be limited to the embodiments disclosed herein, can include practices otherwise than specifically described, and are to be interpreted as broadly as allowed under the law.

What is claimed is:

1. A system for performing explainable pathological analysis of medical images, the system comprising:
   a first processor; and
   a first memory in electrical communication with the first processor, and comprising instructions that, when executed by a processing unit that comprises the first processor or a second processor, and that is in electronic communication with a memory module that comprises the first memory or a second memory, program the processing unit to:
   for a region of interest (ROI) in a whole slide image (WSI) of a tissue, identify features of a plurality of feature types, wherein at least one feature type is at least partially indicative of a pathological condition of the tissue within the ROI;
   operate as a classifier, trained to classify an image using features of the plurality of feature types into one of a plurality of classes of tissue conditions, to: (i) classify the ROI into a class within the plurality of classes, and (ii) designate to the ROI a label indicating a tissue condition associated with the class and with the tissue in the ROI;

store explanatory information about the designation of the label, the explanatory information comprising information about the identified features; and display: (i) at least a portion of the WSI with boundary of the ROI highlighted, (ii) the label designated to the ROI, and (iii) a user interface (UI) comprising: (a) a first UI element for providing to a user access to the stored explanatory information, and (b) one or more additional UI elements enabling the user to provide feedback on the designated label.

2. The system of claim 1, wherein:

the tissue comprises breast tissue; and the plurality of classes of tissue conditions comprises two or more of: invasive carcinoma, ductal carcinoma in situ (DCIS), high-risk benign, low-risk benign, atypical ductal hyperplasia (ADH), flat epithelial atypia (FEA), columnar cell change (CCC), and normal duct.

3. The system of claim 1, wherein:

the tissue comprises lung tissue; and the plurality of classes of tissue conditions comprises: idiopathic pulmonary fibrosis (IPF) and normal.

4. The system of claim 1, wherein:

the tissue comprises brain tissue; and the plurality of classes of tissue conditions comprises: classical cellular tumor and proneural cellular tumor.

5. The system of claim 1, wherein a feature type is cytological features or architectural features (AFs).

6. The system of claim 5, wherein a feature of the feature type cytological features is of one of the subtypes: nuclear size, nuclear shape, nuclear morphology, or nuclear texture.

7. The system of claim 5, a feature of the feature type architectural features is of one of the subtypes: an architectural feature based on a color of a group of superpixels in the ROI (AF-C); (ii) an architectural feature based on a cytological phenotype of nuclei in the ROI (AF-N); or (iii) a combined architectural feature (AF-CN) based on both a color of a group of superpixels in the ROI and a cytological phenotype of nuclei in the ROI.

8. The system of claim 5, a feature of the feature type architectural features is of one of the subtypes: nuclear arrangement, stromal cellularity, epithelial patterns in ducts, epithelial patterns in glands, cell cobblestoning, stromal density, or hyperplasticity.

9. The system of claim 1, wherein the information about the features comprises one or more of:

a total number of features types that were detected in the ROI and that correspond to the tissue condition indicated by the label;

a count of features of a particular feature type that were detected in the ROI;

a measured density of features of the particular feature type in the ROI; or a strength of the particular feature type in indicating the tissue condition.

10. The system of claim 1, wherein the explanatory information comprises a confidence score computed by the classifier in designating the label, wherein the confidence score is based on one or more of:

a total number of feature types that were detected in the ROI and that correspond to the tissue condition indicated by the label;

for a first feature type: (i) a strength of the first feature type in indicating the tissue condition, or (ii) a count of features of the first feature type that were detected in the ROI; or another total number of features types that were detected in the ROI but that correspond to a tissue condition different from the condition associated with the label.

11. The system of claim 1, wherein the instructions further program the processing unit to:

in response to the user interacting with the first UI element:

generate explanatory description using a standard pathology vocabulary and the stored explanatory information; and display the explanatory description in an overlay window, a side panel, or a page.

12. The system of claim 11, wherein the instructions further program the processing unit to:

highlight in the ROI, features of a particular feature type, that at least partially indicates the tissue condition indicated by the label, using a color designated to the feature type; and display the highlighted ROI in the overlay window, the side panel, or the page.

13. The system of claim 1, wherein:

the instructions further program the processing unit to:

repeat the identify, designate, and store operations for a plurality of different ROIs; and prior to the display operation, (i) compute a respective risk metric for each of the ROIs, the risk metric of an ROI being based on: (a) designated label of the ROI, or (b) a confidence score for the ROI, and (ii) sequencing the ROIs according to the respective risk metrics thereof; and to perform the display operation, the instructions program the processing unit to:

display in one panel: (i) at least a portion of the WSI with boundary of the ROI having the highest risk metric highlighted, (ii) the label designated to that ROI, and (iii) a user interface (UI) providing to the user access to the stored explanation for the designated label of that ROI; and display in another panel thumbnails of the sequence of ROIs.

14. The system of claim 1, wherein the instructions further program the processing unit to:

obtain the whole slide image (WSI); and identify the ROI in the WSI, wherein to identify the ROI, the instructions program the processing unit to: (i) mark in the WSI, superpixels of at least two types, one type corresponding to hematoxylin stained tissue and another type corresponding to eosin stained tissue; and (ii) mark segments of pixels of a first type to define an enclosed region as the ROI.

15. The system of claim 14, wherein the instructions further program the processing unit to:

identify a plurality of ROIs in the WSI.

16. The system of claim 1, wherein the instructions further program the processing unit to:

update a training dataset for the classifier wherein, to update the training dataset, the instructions program the processing unit to:

receive from the user via the one or more additional UI elements feedback for the label designated to the ROI, the feedback indicating correctness of the designated label; and store a portion of the WSI associated with the ROI and the designated label in a training dataset.

17. The system of claim 1, wherein the classifier is selected from a group consisting of: a decision tree, a random forest, a support vector machine, an artificial neural network, and a logistic regression based classifier.

18. A system for distributing cases among a group of pathologists, the system comprising:
a first processor; and
a first memory in electrical communication with the first processor, and comprising instructions that, when executed by a processing unit that comprises the first processor or a second processor, and that is in electronic communication with a memory module that comprises the first memory or a second memory, program the processing unit to:
for each one of a plurality of cases, process a corresponding whole slide image (WSI) of a tissue wherein, to process the WSI, the instructions program the processing unit to:
identify one or more regions of interest (ROIs) in the WSI, each ROI having designated thereto a respective diagnostic label indicating a condition of a tissue in the ROI;
for each ROI, compute a respective confidence score for the respective designation;
compute for the WSI: (i) a severity score based on the respective diagnostic labels designated to the one or more ROIs in the WSI; and (ii) a confidence level based on the respective confidence scores for the one or more ROIs;
store as explanatory information, the severity score, the confidence level, and the respective confidence scores;
if the severity score is at or above a specified threshold severity score, transmit the WSI to a rush pathologist in the group of pathologists;
otherwise, if the confidence level is at or below a specified threshold confidence level, transmit the WSI to a subspecialist in the group of pathologists; and
otherwise, transmit the case to a generalist pathologist in the group of pathologists.

19. The system of claim 18, wherein to transmit the case to a general pathologist, the instructions program the processing unit to:
select the general pathologists from a pool of general pathologists within the group of pathologists such that upon transmitting the case to the selected general pathologist maintains a balanced workload for the pool.

20. The system of claim 18, wherein the instructions further program the processing unit to:
designate the respective diagnostic label to at least one ROI in at least one WSI wherein, to designate the respective diagnostic label to a particular ROI, the instructions program the processing unit to:
operate as a classifier, trained to classify an image, using features of a plurality of feature types that are identified in the image, into one of a plurality of classes of tissue conditions, to: (i) classify the ROI into a class within the plurality of classes; and (ii) designate to the ROI a label indicating a tissue condition associated with the class.

21. The system of claim 18, wherein:
for at least one ROI in at least one WSI, the respective diagnostic label was provided by a prior reviewer; and the group of pathologists represents a group of subsequent reviewers.

22. The system of claim 18, wherein the instructions further program the processing unit to:
in response to a user requesting, via a UI element, an explanation for the transmission of a particular WSI:
generate an explanatory description using a standard pathology vocabulary and the stored explanatory information; and
display the explanatory description.

23. The system of claim 22, wherein the instructions further program the processing unit to:
select from the particular WSI, an ROI for which the designated label indicates a severe condition or the confidence score is at or below a specified threshold confidence score;
highlight in the ROI, features of a particular feature type, that at least partially indicates the tissue condition indicated by the label designated to the ROI, using a color designated to the feature type; and
display the highlighted ROI along with the explanatory description.

24. The system of claim 18, wherein the explanatory information comprises, for a first ROI in a first WSI, one or more of:
a total number of features types that were detected in the first ROI and that correspond to the tissue condition indicated by the label designated to the first ROI;
a count of features of a particular feature type that were detected in the first ROI;
a measured density of features of the particular feature type in the first ROI; or
a strength of the particular feature type in indicating a corresponding tissue condition.

25. The system of claim 18, wherein the confidence score for a first ROI in a first WSI is based on one or more of:
a total number of feature types that were detected in the first ROI and that correspond to the tissue condition indicated by the label designated to the first ROI;
for a first feature type: (i) a strength of the first feature type in indicating a corresponding tissue condition, or (ii) a count of features of the first feature type that were detected in the ROI; or
another total number of features types that were detected in the first ROI but that correspond to a tissue condition different from the condition associated with the label designated to the first ROI.

26. A system for ground truth labeling of images used for training a classifier, the system comprising:
a first processor; and
a first memory in electrical communication with the first processor, and comprising instructions that, when executed by a processing unit that comprises the first processor or a second processor, and that is in electronic communication with a memory module that comprises the first memory or a second memory, program the processing unit to:
obtain a whole slide image (WSI) of a tissue;
identify one or more regions of interest (ROIs) in the WSI, wherein identification of an ROI comprises: (i) marking in the WSI, superpixels of at least two types, one type corresponding to hematoxylin stained tissue and another type corresponding to eosin stained tissue; and (ii) marking segments of pixels of a first type to define an enclosed region as the ROI;

display, in a sequence, one or more ROIs; and
for each ROI:
    display one or more UI elements, a first UI element providing or affirming a respective ground-truth label to be assigned to the ROI; and
    in response to the user interacting using the first UI element, designate the respective ground-truth label to the ROI and storing the ROI in a training corpus.

27. The system of claim 26, wherein:
the first UI element indicates the user's agreement with a provided suggestion; and
the instructions further program the processing unit to, for each ROI in at least a subset of the one or more ROIs:
    identify features of a plurality of feature types, wherein at least one feature type is at least partially indicative of a pathological condition of the tissue within the ROI;
    operate as a classifier, trained to classify an image using features of a plurality of feature types into one of a plurality of classes of tissue conditions, to:
        (i) classify the ROI into a class within the plurality of classes;
        (ii) designate to the ROI a suggested label indicating a tissue condition associated with the class; and
        (iii) store explanatory information about the designation of the suggested label, the explanatory information comprising information about the identified features; and
    display the suggested label as the provided suggestion.

28. The system of claim 27, wherein the instructions further program the processing unit to, in response to a user requesting, via a UI element, an explanation for the suggested label for a particular ROI:
    generate an explanatory description using a standard pathology vocabulary and the stored explanatory information; and
    display the explanatory description.

29. The system of claim 28, wherein the instructions further program the processing unit to:
    highlight in the particular ROI, features of a particular feature type, that at least partially indicates the tissue condition indicated by the label designated to the ROI, using a color designated to the feature type; and
    display the highlighted ROI along with the explanatory description.

30. The system of claim 28, wherein the explanatory information comprises, for the particular ROI, one or more of:
    a total number of features types that were detected in the particular ROI and that correspond to the tissue condition indicated by the suggested label designated to the particular ROI;
    a count of features of a particular feature type that were detected in the particular ROI;
    a measured density of features of the particular feature type in the particular ROI; or
    a strength of the particular feature type in indicating a corresponding tissue condition.

31. The system of claim 28, wherein the confidence score for the particular ROI is based on one or more of:
    a total number of feature types that were detected in the particular ROI and that correspond to the tissue condition indicated by the suggested label designated to the particular ROI;
    for a first feature type: (i) a strength of the first feature type in indicating a corresponding tissue condition, or (ii) a count of features of the first feature type that were detected in the particular ROI; or
    another total number of features types that were detected in the particular ROI but that correspond to a tissue condition different from the condition associated with the suggested label designated to the particular ROI.

* * * * *

UNITED STATES PATENT AND TRADEMARK OFFICE
CERTIFICATE OF CORRECTION

| | |
|---|---|
| PATENT NO. | : 11,842,488 B2 |
| APPLICATION NO. | : 17/843309 |
| DATED | : December 12, 2023 |
| INVENTOR(S) | : Akif Burak Tosun et al. |

It is certified that error appears in the above-identified patent and that said Letters Patent is hereby corrected as shown below:

In the Specification

In the "CROSS-REFERENCE TO RELATED APPLICATIONS" at Column 1, Line 7, please replace "Mar. 16, 2019," with --"Mar. 16, 2020,"--.

Signed and Sealed this
Tenth Day of September, 2024

Katherine Kelly Vidal
*Director of the United States Patent and Trademark Office*